United States Patent
Kumar et al.

(10) Patent No.: US 9,290,777 B2
(45) Date of Patent: Mar. 22, 2016

(54) PUTATIVE CYTOKININ RECEPTOR AND METHODS FOR USE THEREOF

(75) Inventors: Prakash Pallathadka Kumar, Singapore (SG); Mandar Radhakisan Godge, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 1414 days.

(21) Appl. No.: 12/525,968

(22) PCT Filed: Feb. 5, 2008

(86) PCT No.: PCT/SG2008/000039
§ 371 (c)(1),
(2), (4) Date: Sep. 23, 2010

(87) PCT Pub. No.: WO2008/097197
PCT Pub. Date: Aug. 14, 2008

(65) Prior Publication Data
US 2011/0023187 A1     Jan. 27, 2011

Related U.S. Application Data

(60) Provisional application No. 60/888,136, filed on Feb. 5, 2007.

(51) Int. Cl.
*C12N 15/82*     (2006.01)
*C12N 15/87*     (2006.01)
*C07K 14/415*    (2006.01)

(52) U.S. Cl.
CPC .......... *C12N 15/8295* (2013.01); *C07K 14/415* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 5,558,071 A * | 9/1996 | Ward et al. | 123/598 |
| 5,780,296 A | 7/1998 | Holloman et al. | |
| 6,255,113 B1 | 7/2001 | Zarling et al. | |
| 6,579,851 B2 * | 6/2003 | Goeke et al. | 514/11.7 |
| 6,686,515 B1 | 2/2004 | Lassner et al. | |
| 7,847,156 B2 * | 12/2010 | Inze | C07K 14/415 800/287 |
| 8,461,129 B2 * | 6/2013 | Bolduc et al. | 514/54 |
| 2006/0021088 A1 * | 1/2006 | Inze et al. | 800/281 |
| 2011/0028412 A1 * | 2/2011 | Cappello et al. | 514/25 |
| 2013/0041094 A1 * | 2/2013 | Drager et al. | 514/394 |
| 2013/0084243 A1 * | 4/2013 | Goetsch et al. | 424/1.49 |
| 2013/0096073 A1 * | 4/2013 | Sidelman | 514/21.6 |

FOREIGN PATENT DOCUMENTS

| | | |
|---|---|---|
| EP | 1033405 A2 | 9/2000 |
| WO | 9206205 A1 | 4/1992 |
| WO | 9748814 | 12/1997 |
| WO | 9925821 A1 | 5/1999 |
| WO | 9925840 A1 | 5/1999 |
| WO | 9925854 A1 | 5/1999 |
| WO | 9925855 A1 | 5/1999 |
| WO | 9932619 A1 | 7/1999 |
| WO | 9949029 A1 | 9/1999 |
| WO | 9953050 A1 | 10/1999 |
| WO | 0170949 A1 | 9/2001 |
| WO | 2004035798 A2 | 4/2004 |

OTHER PUBLICATIONS

AtGenExpress Visualization Tool, Accessed at: http://jsp.weigelworld.org/expviz/expviz.jsp?experiment=development&normalization=absolute&probesetcsv=At4g13940&action=Run, on Aug. 19, 2013.*
Shmid et al, A gene expression map of *Arabidopsis thaliana* development, Nat. Genet. (2005) 37:501-506.*
Tanaka et al, Morphological changes and hypomethylation of DNA in transgenic tobacco expressing antisense RNA of the S-adenosyl-L-homocysteine hydrolase gene, Plant Molecular Biology (1997) 35:981-986.*
Rocha et al, The *Arabidopsis* Homology-Dependent Gene Silencing1 gene codes for an S-adenosyl-L-homocystein hydrolase required for DNA methylation-dependent gene silencing, Plant Cell (2005) 17:404-417.*
Li et al, Down-regulation of S-adenosyl-L-homocysteine hydrolase reveals a role of cytokinin in promoting transmethylation reactions, Planta (2008) 228:125-136.*
Thomas et al, Size contraints for targeting post-transcriptional gene silencing and for RNA-directed methylation of *Nicotiana benthamiana* using a potato virus X factor, Plant. J. (2001) 25:417-425.*

(Continued)

*Primary Examiner* — Shubo (Joe) Zhou
*Assistant Examiner* — Mykola Kovalenko
(74) *Attorney, Agent, or Firm* — Cantor Colburn LLP

(57) ABSTRACT

A method of modulating the expression of at least one trait in a plant, the method comprising the step of modulating the expression of at least one polypeptide by the plant, wherein the polypeptide is selected from the group consisting of: i) a polypeptide which comprises the amino acid sequence according to SEQ ID NO:1; ii) a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant; iii) a polypeptide which comprises an amino acid sequence with at least 70% sequence identity to the amino acid sequence according to SEQ ID NO:1 and which is capable of modulating cytokinin signaling in the plant; and iv) a polypeptide which consists of an amino acid sequence according to SEQ ID NO:1, wherein the modulation of the expression of the polypeptide modulates the expression of at least one trait in the plant.

8 Claims, 13 Drawing Sheets

(56) References Cited

OTHER PUBLICATIONS

Senthil-Kumar et al, A systematic study to determine the extent of gene silencing in *Nicotiana benthamiana* and other *Solanaceae* species when heterologous gene sequences are used for virus-induced gene silencing, New Phytologist (2007) 176:782-791.*

GenBank Accession No. AY256916, *Arabidopsis thaliana* S-adenosyl-L-homocystein hydrolase, first submitted Mar. 17, 2003, first updated on Sep. 1, 2007.*

International Search Report; International Application No. PCT/SG2008/000039; International Filing Date: Feb. 5, 2008; Date of Mailing: May 16, 2008; 5 Pages.

European Search Report; International Application No. PCT/SG08/000039; Mailing Date: Dec. 23, 2009; 5 Pages.

Written Opinion of the International Searching Authority; International Application No. PCT/SG2008/000039; International Filing Date: Feb. 5, 2008; Date of Mailing: May 16, 2008; 5 Pages.

Rocha et al.; "The *Arabidopsis* Homology-Dependent Gene SILENCING1 Gene Codes for an S-Adenosyl-L-Homocysteine Hydrolase Required for DNA Methylation-Dependent Gene Silencing"; The Plant Cell, vol. 17; Feb. 2005; pp. 404-417.

Rupp et al.; "Increased Steady State mRNA Levels of the STM and KNAT1 Homeobox Genes in Cytokinin Overproducing *Arabidopsis thaliana* Indicate a Role for Cytokinins in the Shoot Apical Meristem" The Plant Journal, vol. 18, Issue 5; 1999; pp. 557-563.

Shu et al.; "S-Adenosylhomocysteine Hydrolase is Localized at the Front of Chemotaxing Cells, Suggesting a Role for Transmethylation During Migration"; Proc. Natl. Acad. Sci. USA; vol. 103, Issue 52; Dec. 26, 2006; pp. 19788-19793.

Taniguchi et al.; "Expression of *Arabidopsis* Response Regulator Homologs is Induced by Cytokinins and Nitrate"; FEBS Letters, vol. 429; 1998; p. 259-262.

To et al.; "Type-A *Arabidopsis* Response Regulators Are Partially Redundant Negative Regulators of Cytokinin Signaling"; The Plant Cell, vol. 16; Mar. 2004; pp. 658-671.

Vergunst, A. et al.; "Site-Specific Integration of *Agrobacterium* T-DNA in *Arabidopsis thaliana* Mediated by Cre Recombinase"; Nucleic Acids Research; vol. 26, Issue 11; 1998; pp. 2729-2734.

Vergunst et al.; "Cre/lox-mediated Site-Specific Integration of *Agrobacterium* T-DNA in *Arabidopsis thaliana* by Transient Expression of Cre"; Plant Molecular Biology, vol. 38; 1998; pp. 393-406.

Waterhouse, P.M. et al.; "Virus Resistance and Gene Silencing in Plants Can Be Induced by Simultaneous Expression of Sense and Antisense RNA"; Proc. Natl. Acad. Sci. USA, vol. 95; Nov. 1998; pp. 13959-13964.

Yang et al.; "Investigation of Cytokinin-Deficient Phenotypes in *Arabidopsis* by Ectopic Expression of Orchid DSCKX1"; FEBS Letters, vol. 555; 2003; pp. 291-296.

Yu et al.; "Floral Homeotic Genes are Targets of Gibberellin Signaling in Flower Development"; Proc. Natl. Acad. Sci. USA; vol. 101, Issue 20; May 18, 2004; pp. 7827-7832.

Zhang et al.; "A Putative Nucleoporin 96 Is Required for Both Basal Defense and Constitutive Resistance Responses Mediated by Suppressor of npr1-1, constitutive 1"; The Plant Cell, vol. 17; Apr. 2005; pp. 1306-1316.

User Bulletin: ABI Prism 7700 Sequence Distribution System; "Sequence Detection System (SDS) Software Version 1.9.1 Update"; Nov. 5, 2002; 16 Pages.

Altschul, S.F.; "A Protein Alignment Scoring System Sensitive at All Evolutionary Distances"; J. Mol. Evol., vol. 36; 1993; pp. 290-300.

Altschul et al.; "Basic Local Alignment Search Tool"; J. Mol. Biol., vol. 215; 1990; p. 403-410.

Bernstein et al.; "Role for a Bidentate Ribonuclease in the Initiation Step of RNA Interference"; Nature, vol. 409; Jan. 18, 2001; pp. 363-366.

Brandstatter et al.; "Two Genes with Similarity to Bacterial Response Regulators Are Rapidly and Specifically Induced by Cytokinin in *Arabidopsis*"; The Plant Cell, vol. 10; Jun. 1998; pp. 1009-1020.

Clough, S.J. et al.; "Floral Dip: A Simplified Method for *Agrobacterium*-mediated Transformation of *Arabidopsis thaliana*"; The Plant Journal; vol. 16; 1999; pp. 735-743.

Cytokinins; Date Accessed: Nov. 5, 2009; http://www.plant-hormones.info/cytokinins.htm; 2 Pages.

DAgostino et al.; Plant Physiology, vol. 124; Dec. 2000; pp. 1706-1717.

Database GenBank, Accession No. AY042866; Accessed: Oct. 6, 2008; 2 Pages.

Database GenBank, Accession No. AY081468; Accessed: Oct. 6, 2008; 2 Pages.

Database GenBank, Accession No. AY090284; Accessed: Oct. 6, 2008; 2 Pages.

Database GenBank, Accession No. AY256916; Date Accessed: Mar. 12, 2009; 2 Pages.

Database GenPept, Accession No. AAC14714; Date Accessed: Oct. 6, 2008; 2 Pages.

Database GenPept, Accession No. AAG40389; Date Accessed: Oct. 6, 2008; 3 Pages.

Database GenPept, Accession No. AAK68806; Date Accessed: Oct. 6, 2008; 2 Pages.

Devereux et al.; "A Comprehensive Set of Sequence Analysis Programs for the VAX"; Nucleic Acids Research; vol. 12, No. 1; 1984; pp. 387-395.

Elbashir et al.; "Duplexes of 21-Nucleotide RNAs Mediate RNA Interference in Cultured Mammalian Cells"; Nature, vol. 411; 2001; pp. 494-498.

Fire et al.; "Potent and Specific Genetic Interference by Double-Stranded RNA in *Caenorhabditis elegans*"; Nature, vol. 391; 1998; pp. 806-811.

Forler et al.; "An Efficient Protein Complex Purification Method for Functional Proteomics in Higher Eukaryotes"; Nature; vol. 21; Jan. 2003; pp. 89-92.

Hamilton et al.; "A Species of Small Antisense RNA in Post-transcriptional Gene Silencing in Plants"; Science, New Series; vol. 286, No. 5441; Oct. 29, 1999; pp. 950-952.

Hammond et al.; "An RNA-directed Nuclease Mediates Post-Transcriptional Gene Silencing in *Drosophila* Cells"; Nature, vol. 404; 2000; pp. 293-296.

Hammond et al.; "Post-Transcriptional Gene Silencing by Double-Stranded RNA"; Nature Reviews, Genetics; vol. 2; Feb. 2000; pp. 110-119.

Hiei et al.; "Efficient Transformation of Rice (*Oryza sativa* L.) Mediated by *Agrobacterium* and Sequence Analysis of the Boundaries of the T-DNA"; The Plant Journal; vol. 6, Issue 2; 1994; pp. 271-282.

Higuchi et al.; "In Planta Functions of the *Arabidopsis* Cytokinin Receptor Family"; Proc. Natl. Acad. Sci. USA; vol. 101, Issue 23; Jun. 8, 2004; pp. 8821-8826.

Hutchinson et al.; "The *Arabidopsis* Histidine Phosphotransfer Proteins Are Redundant Positive Regulators of Cytokinin Signaling"; The Plant Cell; vol. 18; Nov., 2006; pp. 3073-3087.

Hwang et al.; "Two-Component Circuitry in *Arabidopsis* Cytokinin Signal Transduction"; Nature, vol. 413; Sep. 27, 2001; pp. 383-389.

Imamura et al.; "Response Regulators Implicated in His-to-Asp Phosphotransfer Signaling in *Arabidopsis*"; Proc. Natl. Acad. Sci. USA; vol. 95; Mar. 1998; pp. 2691-2696.

Inoue et al; "Identification of CRE1 as a Cytokinin Receptor from *Arabidopsis*"; Nature, vol. 409; Feb. 22, 2001; pp. 1060-1063.

Kiba et al.; "Differential Expression of Genes for Response Regulators in Response to Cytokinins and Nitrate in *Arabidopsis thaliana*": Plant Cell Physiol.; vol. 40, Issue 7; 1999; pp. 767-771.

Koncz, C. et al.; The Promoter of TL-DNA Gene 5 Controls the Tissue-Specific Expression of Chimaeric Genes Carried by a Novel Type of *Agrobacterium* Binary Vector; Mol. Gen. Genet., vol. 204; 1986; pp. 383-396.

Kozak; "Structural Features in Eukaryotic mRNAs That Modulate the Initiation of Translation"; The Journal of Biological Chemistry, vol. 266; Oct. 1991; pp. 19867-19870.

Lieber et al.; "Selection of Efficient Cleavage Sites in Target RNAs by Using a Ribozyme Expression Library"; Molelcular and Cellular Biology, vol. 15; Jan. 1995; pp. 540-551.

(56) References Cited

OTHER PUBLICATIONS

Lukowitz, W. et al.; "Positional Cloning in *Arabidopsis*: Why It Feels Good to Have a Genome Initiative Working for You"; Plant Physiology; vol. 123; Jul. 2000; pp. 795-805.

McCormick, S. et al.; "Leaf Disc Transformation of Cultivated Tomato (L. *esculentum*) Using *Agrobacterium tumefaciens*"; Plant Cell Reports; vol. 5; 1986; pp. 81-84.

Napoli et al.; "Introduction of a Chimeric Chalcone Synthase Gene into Petunia Results in Reversible Co-Suppression of Homologous Genes in trans"; The Plant Cell; vol. 2; Apr. 1990; pp. 279-289.

Needleman et al.; "A General Method Applicable to the Search for Similarities in the Amino Acid Sequence of Two Proteins"; J. Mol. Biol., vol. 48; 1970; pp. 443-453.

Napoli et al.; "The Petunia Paradox: Added Copies of Genes Have Puzzling Effects in Plants"; J. NIH Ris., vol. 3; Dec. 1991; pp. 49-54.

Database GenBank, Accession No. NP 193130; Version No. 193.130.1; Accessed: Jun. 9, 2006; 2 Pages.

European Examination Report; European Application No. 08705428.4; Date of Mailing: Oct. 26, 2010; 8 Pages.

Celia Hooper; "The Petunia Paradox: Added Copies of Genes Have Puzzling Effects in Plants"; The Journal of NIH Research, vol. 3; Dec. 1991; pp. 49-54.

Ishimoto, M. et al. ; "Expression of a rice feed back-insensitive alpha subunit of anthranilate synthase enhances tryptophan content in transgenic soybean seeds"; Breeding Research; Sep. 21, 2004; vol. 6; Supplement No. 2; p. 214 (cited in JP Office Action of Oct. 15, 2012).

Japan Office Action dated Oct. 15, 2012; Japan Application No. 2009-548206; 13 Pages.

Entrez Nucleotide and Entrez Protein FAQs, Entrez Sequences Help [Internet]. Bethesda (MD), National Center for Biotechnology Information (US), downloaded Jul. 22, 2015 from http://www.ncbi.nlm.nih.gov/books/NBK49541/, 7 pages.

NCBI Accession AY256916 revision history, downloaded May 18, 2015 from http://www.ncbi.nlm.nih.gov/nuccore/AY256916.1?report=girevhist, 1 page.

NCBI Sample GENBANK Record, downloaded Jul. 27, 2015 from http://www.ncbi.nlm.nih.gov/Sitemap/samplerecord.html, 17 pages.

\* cited by examiner

Figure 6A

```
HOG2                          MALLVEKTSSGREYKVKDMSQADFGRIEIELAEVEMPGLVSCVAEFGPSQPLKGARTTGSLHM
HOG1 (SEQ ID:1)               MALIVEKTSGGREYKVKDMSQADFGRLELELAEVEMPGLMACRTEFGPAQPFKGARITGSLHM
Petunia hybrida (SEQ ID:13)   MALLVEKTTSGREYKVKDMSQADFGRIEIELAEVEMPGLMACRTEFGPSQPFKGAKTTGSLHM
Nicotiana tabacum (SEQ ID:3)  MALLVEKTISGREYKVKDMSQADFGRLEIELAEVEMPGLMACRTEFGPSQPFKGAKITGSLHM
Orzya sativa (SEQ ID:5)       MALSVEKTSSGREYKVKDLSQADFGRLEIELAEVEMPGLMACRAEFGPSQPFKGARISGSLHM
Triticum aestivum (SEQ ID:7)  MALSVEKTSSGREYKVKDLFQADFGRLELELAEVEMPGLMACRTEFGPSQPFKGARISG LHM
Homo sapiens (SEQ ID:26)      -------MSDKLPYKVADIGLAAWGRKALDIAENEMPGLMRMRERYSASKPLKGARIAGCLHM
                                     ****::* :****:**:***:*:*

SAHH 1st SIGNATURE
HOG2                          TIQTAVLIETLTALGAEVRWCSCNIFSTQDHAAAAIARDSAAVFAWKGETLQEYWWCTERALD
HOG1 (SEQ ID:1)               TIQTAVLIETLTALGAEVRWCSCNIFSTQDHAAAAIARDSAAVFAWKGETLQEYWWCTERALD
Petunia hybrida (SEQ ID:13)   TIQTAVLIETLTALGAEVRWCSCNIFSTQDHAAAAIARDSAAVFAWKGETLQEYWWCTERALD
Nicotiana tabacum (SEQ ID:3)  TIQTAVLIETLTALGAEVRWCSCNIFSTQDHAAAAIARDSAAVFAWKGETLQEYWWCTERALD
Orzya sativa (SEQ ID:5)       TIQTAVLIETLTALGAEVRWCSCNIFSTQDHAAAAIARDSAAVFAWKGETLEEYWWCTERCLD
Triticum aestivum (SEQ ID:7)  TIQTAVLIETLTALGAEVRWCSCNIFSSQDHAAAAIARDSAAVFAWKGETLEEYWWCTERCLD
Homo sapiens (SEQ ID:26)      TVETAVLIETLVTLGAEVQWSSCNIFSTQDHAAAAIAKAGIPVYAWKGETDEEYLWCIEQTLY
                              ******************** :********************* .*****

HOG2                          WGPCGGPDLIVDDGGDATLLIHECVKAEEIFAKNGTFPDPTSTDNPEFQIVLSIIKDGLQVDP
HOG1 (SEQ ID:1)               WGPGGGPDLIVDDGGDATLLIHEGVKAEEIFEKTGQVPDPTSTDNPEFQIVLSIIKEGLQVDP
Petunia hybrida (SEQ ID:13)   WGPCCGPDLIVDDCGDATLLIHECVKAEEEYAKDGTVPDPTSTDNVEFQLVLGIIKESLKTDP
Nicotiana tabacum (SEQ ID:3)  WGPCGGPDLIVDDCGDATLLIHECVKAEEEYAKNGTIPDPNSTDNAEFQLVLTIIKESLKTDP
Orzya sativa (SEQ ID:5)       WGVGGGPDLIVDDGGDATLLIHEGVKAEEEFEKSGKVPDPESTDNAEFKIVLTIIRDGLKSDP
Triticum aestivum (SEQ ID:7)  WGVCGGPDLIVDDCGDATLLIHECVKAEEEFEKSGKVPDPESTDNPEFKIVLTIIRDGLKTDA
Homo sapiens (SEQ ID:26)      FK DGPLNMILDDGGDLTNLIHT

:**.**** ************.*********** : * .*** **** *::.:** *

HOG2                          KKYHKMKERLVGVSEETTTGVKRLYQMQETGALLFPAINVNDSVTKSKFDNLYGCRHSLPDGL
HOG1 (SEQ ID:1)               KKYHKMKGRLVGVSEETTTGVKRLYQMQESGALLFPAINVNDSVTKSKFDNLYGCRHSLPDGL
Petunia hybrida (SEQ ID:13)   TKHTKMKERLVGVSEETTTGVKRLTRCKLMELCFSQLPNVNDSVTKSKFDNLYGCRHSLPDGL
Nicotiana tabacum (SEQ ID:3)  LKYTKMKERLVGVSEETTTGVKRLYQMQANGTLLFPAINVNDSVTKSKFDNLYGCRHSLPDGL
Orzya sativa (SEQ ID:5)       SKYRKMKERLVGVSEETTTGVKRLYQMQETGALLFPATNVNDSVTKSKFDNLYGCRHSLPDGL
Triticum aestivum (SEQ ID:7)  SKYRKMKERLVGVSEETTTGVKRLYQMQESGTLLFPAINVNDSVTKSKFDNLYGCRHSLPDGL
Homo sapiens (SEQ ID:26)      -KYPQLLPGIRGISEETTTGVHNLYKMMANGTLKVPAINVNDSVTKSKFDNLYGCRESLTDGT

*::.*: *..:: *** *:************** : :       ************

SAHH 2nd SIGNATURE
HOG2                          MRATDVMIAGKVAVICGYGDVGKGCAAAMKTAGARVIVTEIDPICALQA MEGLQVLTLEDVV
HOG1 (SEQ ID:1)               MRATDVMIAGKVAVICGYGDVGKGCAAAMKTAGARVIVTEIDPICALQAMMEGLQVLTLEDVV
Petunia hybrida (SEQ ID:13)   MRATDVMIAGKVAVVAGYGDVGKGCAMSLKQAGARVIVTEIDPICALQALMEGLQVLTLEDVV
Nicotiana tabacum (SEQ ID:3)  MRATDVMIAGKVALVAGYGDVGKGCAAALKQAGARVIVTEIDPICALQATMEGLQVLTLEDVV
Orzya sativa (SEQ ID:5)       MRATDVMIAGKVAVVCGYGDVGKGCAAALKQAGARVIVTEIDPICALQALMEGLQVLTLEDVV
Triticum aestivum (SEQ ID:7)  MRATDVMIAGKVAVVCGYGDVGKGCAAALKQAGARVIVTEIDPICALQALMEGIQILTLEDVV
Homo sapiens (SEQ ID:26)      KRATDVMIAGKVAVVAGYGDVGKGCAQALRGFGARVIITEIDPINALQAAMEGYEVTTMDEAC

********************.*:.*********  ::* .***************

HOG2                          SEADIFCTTTGNKDIIMVDHMRKMKNNAIVCNIGHFDNEIDMLSLETYPGVKRITIKPQTDRW
HOG1 (SEQ ID:1)               SEADIFVTTTGNKDIIMVDHMRKMKNNAIVCNIGHFDNEIDMQGLETFPGVKRITIKPQTDRW
Petunia hybrida (SEQ ID:13)   ADADIFVTTTGNKDIIMVDHMRKMKNNAIVCNIGHFDNEIDMLGLETFPGVKRITIKPQTDRW
Nicotiana tabacum (SEQ ID:3)  SDVDIFVTTTGNKDIIMVDHMRKMKNNAIVCNIGHFDNEIDMLSLETYPGVKRITIKPQTDRW
Orzya sativa (SEQ ID:5)       SEADIFVTTTGNKDIIMVDHMRKMKNNAIVCNIGHFDNEIDMLSLETYPGVKRITIKPQTDRW
Triticum aestivum (SEQ ID:7)  SEADIFVTTTGNKDIIMVDHMRKMKNNAIVCNIGHFDNEIDMNGLETYPGVKRITIKPQTDRW
Homo sapiens (SEQ ID:26)      QEGNIFVTTTGCIDIILGRHFEQMKDDAIVCNIGHFDVEIDVKWLNEN-AVEKVNIKPQVDRY

*:***:*:***:**:: **** ***********..*:**************** **

HOG2                          VFPDTNSGIIVLAEGRLMNLGCATGHPSFVMSCSFTNQVIAQLELWNEKSSGKYEKKVYVLPK
HOG1 (SEQ ID:1)               VFPDTKSGIIVLAEGRLMNLGCATGHPSFVMSCSFTNQVIAQLELWNEKSSGKYEKKVYVLPK
Petunia hybrida (SEQ ID:13)   VFPDTNSGIIVLAEGRLMNLGCATGHPSVVMSCSFTNQVIAQLELWNEKSSGKYEKKVYVLPK
Nicotiana tabacum (SEQ ID:3)  VFPDTNSGIIVLAEGRLMNLGCATGHPSFVMSCSFTNQVIAQLELWNEKSSGKYEKKVYVLPK
Orzya sativa (SEQ ID:5)       VFPETNTGIIVLAEGRLMNLGCATGHPSFVMSCSFTNQVIAQLELWKEKSTGKYEKKVYVLPK
Triticum aestivum (SEQ ID:7)  VFPETKTGIIVLAEGRLMNLGCATGHPSFVMSCSFTNQVIAQLELWNEKASGKYEKKVYVLPK
Homo sapiens (SEQ ID:26)      RLKNGRR-IILLAEGRLVNLGCAMGHPSFVMSNSFTNQVMAQIELWTHP--DKYPVGVHFLPK

```
HOG2                         HLDEKVAALHLGKLGARLTKLTKDQSDYVSIPVEGPYKPVHYRY
HOG1 (SEQ ID:1)              HLDEKVAALHLGKLGAKLTKLTKDQSDYVSIPIEGPYKPPHYRY
Petunia hybrida (SEQ ID:13)  HLDEKVAALHLGKLGAKLTKLSKDQADYINVPVEGPYKPVHYRY
Nicotiana tabacum (SEQ ID:3) HLDEKVAALHLGKLGAKLTKLSKDQADYISVPVEGPYKPAHYRY
Orzya sativa (SEQ ID:5)      HLDEKVAALHLGKLGARLTKLSKSQADYISVPVEGPYKPAHYRY
Triticum aestivum (SEQ ID:7) HLDEKVAALHLGKLGARLTKLTKSQSDYISIPIEGPYKLRLYRY
Homo sapiens (SEQ ID:26)     KLDEAVAEAHLGKLNVKLTKLTEKQAQYLGMSCDGPFKPDHYRY

| | |
|---|---|
| SEQ ID:1 | MALIVEKTSGGREYKVKDMSQADFGRLELELAEVEMPGLMACRTEFGPAQPFKGARITGS |
| SEQ ID:5 | MALSVEKTSSGREYKVKDLSQADFGRLEIELAEVEMPGLMACRAEFGPSQPFKGARISGS |
| SEQ ID:13 | MALLVEKTTSGREYKVKDMSQADFGRLEIELAEVEMPGLMACRTEFGPSQPFKGAKITGS |
| | |
| SEQ ID:1 | LHMTIQTAVLIETLTALGAEVRWCSCNIFSTQDHAAAAIARDSAAVFAWKGETLQEYWWC |
| SEQ ID:5 | LHMTIQTAVLIETLTALGAEVRWCSCNIFSTQDHAAAAIARDSAAVFAWKGETLEEYWWC |
| SEQ ID:13 | LHMTIQTAVLIETLTALGAEVRWCSCNIFSTQDHAAAAIARDSAAVFAWKGETLQEYWWC |
| | |
| SEQ ID:1 | TERALDWGPGGGPDLIVDDGGDATLLIHEGVKAEEIFEKTGQVPDPTSTDNPEFQIVLSI |
| SEQ ID:5 | TERCLDWGVGGGPDLIVDDGGDATLLIHEGVKAEEEFEKSGKVPDPESTDNAEFKIVLTI |
| SEQ ID:13 | TERALDWGPGGGPDLIVDDGGDATLLIHEGVKAEEEYAKDGTVPDPTSTDNVEFQLVLGI |
| | |
| SEQ ID:1 | IKEGLQVDPKKYHKMKGRLVGVSEETTTGVKRLYQMQESGALLFPAINVNDSVTKSKFDN |
| SEQ ID:5 | IRDGLKSDPSKYRKMKERLVGVSEETTTGVKRLYQMQETGALLFPAINVNDSVTKSKFDN |
| SEQ ID:13 | IKESLKTDPTKHTKMKERLVGVSEETTTGVKRLTRCKLMELCFSQLPNVNDSVTKSKFDN |
| | |
| SEQ ID:1 | LYGCRHSLPDGLMRATDVMIAGKVAVICGYGDVGKGCAAAMKTAGARVIVTEIDPICALQ |
| SEQ ID:5 | LYGCRHSLPDGLMRATDVMIAGKVAVVCGYGDVGKGCAAALKQAGARVIVTEIDPICALQ |
| SEQ ID:13 | LYGCRHSLPDGLMRATDVMIAGKVAVVAGYGDVGKGCAMSLKQAGARVIVTEIDPICALQ |
| | |
| SEQ ID:1 | AMMEGLQVLTLEDVVSEADIFVTTTGNKDIIMVDHMRKMKNNAIVCNIGHFDNEIDMQGL |
| SEQ ID:5 | ALMEGLQVLTLEDVVSEADIFVTTTGNKDIIMVDHMRKMKNNAIVCNIGHFDNEIDMLGL |
| SEQ ID:13 | ALMEGLQVLTLEDVVADADIFVTTTGNKDIIMVDHMRKMKNNAIVCNIGHFDNEIDMLGL |
| | |
| SEQ ID:1 | ETFPGVKRITIKPQTDRWVFPDTKSGIIVLAEGRLMNLGCATGHPSFVMSCSFTNQVIAQ |
| SEQ ID:5 | ETYPGVKRITIKPQTDRWVFPETNTGIIVLAEGRLMNLGCATGHPSFVMSCSFTNQVIAQ |
| SEQ ID:13 | ETYPGVKRITIKPQTDRWVFPDTNSGIIVLAEGRLMNLGCATGHPSVVMSCSFTNQVIAQ |
| | |
| SEQ ID:1 | LELWNEKSSGKYEKKVYVLPKHLDEKVAALHLGKLGAKLTKLTKDQSDYVSIPIEGPYKP |
| SEQ ID:5 | LELWKEKSTGKYEKKVYVLPKHLDEKVAALHLGKLGARLTKLSKSQADYISVPVEGPYKP |
| SEQ ID:13 | LELWNEKSSGKYEKKVYVLPKHLDEKVAALHLGKLGAKLTKLSKDQADYINVPVEGPYKP |
| | |
| SEQ ID:1 | PHYRY |
| SEQ ID:5 | AHYRY |
| SEQ ID:13 | VHYRY | b

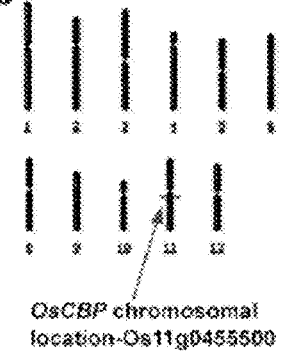

OsCBP chromosomal
location-Os11g0455500

PUTATIVE CYTOKININ RECEPTOR AND METHODS FOR USE THEREOF

TECHNICAL FIELD

The present invention relates to the modulation of the expression of traits in plants, such as plant height, plant biomass, apical bud development, branching, fertility, flowering, leaf area, senescence, seed germination, seed yield, seed weight, stem development, grain yield, tiller number, floral meristem development and root development. The present invention also relates to methods and materials for the modulation of the expression of the traits in plants.

BACKGROUND

Traditional plant breeding techniques are known to result in improvements in agricultural crops. These techniques such as selective breeding and hybridization involve the crossing of genes derived from plants with different genetic backgrounds to generate progeny of various characteristics. The progeny is selected to obtain the plants that express the desired traits and the deleterious traits are eliminated via multiple backcrossings or selfings to eventually yield progeny with the desired characteristics. Although traditional breeding methods have proven to be useful in enhancing or improving the characteristics of various crops, these methods involve the crossing of hundreds or thousands of genes in which only a few genes are selected for their improved characteristics or traits. Furthermore, these methods take many years of crossing, selecting a number of lines from a large population of progeny and backcrossing it for several generations to obtain the desired trait. Some undesirable traits may also be manifested in the plants because it is usually difficult to select for one trait without affecting others using traditional breeding methods.

Another disadvantage in traditional plant selection is that breeding is restricted to plants that are sexually compatible, and therefore traditional breeding methods are usually limited by the lack of genetic diversity in the germplasm of a particular species. Moreover, traditional breeding methods have proven to be rather ineffective for improving many polygenic traits such as increased disease resistance.

Although there have been considerable advances in crop yields in recent years, there remains a need to achieve significant improvements in major food crops to meet global demand. Recent advances in plant biotechnology involving the expression of single transgene in crops have resulted in the successful commercial introduction of new plant traits such as herbicide resistance, insect resistance and virus resistance. However, the list of single gene traits of significant value is relatively small, and therefore single transgene expression in crops is not practical for crop improvement.

In recent years, there have been attempts to isolate certain genes in various plant species which are known to chemically modify the DNA sequence in the plant so that the effects in plant morphology could be characterized. One known method involves the isolation of the S-adenosyl-L-homocysteine hydrolase (SAHH) gene, a key enzyme which is known to regulate the methylation of DNA. Although certain morphological changes were observed in the plant, none of the phenotypic traits proved to have a significant advantage in improving crop yield in different plants. Due to the complexity of the interaction between the SAHH gene and the downstream molecules, the mechanisms involving the DNA methylation and gene expression are poorly understood and existing methods for crop improvement are therefore limited.

Thus, there is a need to provide new methods that overcome, or at least ameliorate, one or more of the disadvantages described above. There is a need for new methods for producing plants having traits that are useful for crop improvement and other commercial and scientific uses.

SUMMARY

The present inventors have identified a polypeptide comprising the amino acid sequence according to SEQ ID NO: 1, which is involved in the cytokinin-signaling pathway in plants. Cytokinins are phytohormones (or plant hormones) that are exerted in responsive plant cells to provide specific biochemical and physiological effects. Phytohormones are first recognized by specific receptors which initiate the transduction of the hormonal signal to stimulate cellular response important in plant growth and development. While hormone receptors are well studied in many eukaryotes ranging from flowering plants to man, there have been a lack of a detailed understanding of phytohormone receptors. Phytohormone binding proteins have been suspected to provide candidates for such receptors.

The present inventors have identified a significant increase in plant biomass and crop yield, in both monocotyledonous and dicotyledonous species, when the expression of the polypeptide comprising the amino acid sequence according to SEQ ID NO: 1 was decreased. In contrast, the increased expression of the polypeptide comprising the amino acid sequence according to SEQ ID NO: 1, provided early flowering in some plants. Therefore, the expression of the polypeptide comprising the amino acid sequence according to SEQ ID NO: 1 can be manipulated to obtain the desired traits which are important for crop improvement and other commercial and scientific uses.

Thus, according to a first aspect of the invention, there is provided a method of modulating the expression of at least one trait in a plant, the method comprising the step of modulating the expression of at least one polypeptide by the plant, wherein the polypeptide is selected from the group consisting of:

i) a polypeptide which comprises the amino acid sequence according to SEQ ID NO: 1;

ii) a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant;

iii) a polypeptide which comprises an amino acid sequence with at least 70% sequence identity to the amino acid sequence according to SEQ ID NO: 1 and which is capable of modulating cytokinin signaling in the plant; and iv) a polypeptide which consists of an amino acid sequence according to SEQ ID NO: 1, wherein the modulation of the expression of the polypeptide modulates the expression of at least one trait in the plant.

In one embodiment, the expression of the polypeptide by the plant is modulated by introducing at least one polynucleotide which modulates the expression of the polypeptide into one or more cells of the plant.

In another embodiment, there is provided a method as defined above wherein the step of modulating the expression of the polypeptide comprises decreasing the expression of the polypeptide. The step of decreasing the expression of the polypeptide by the plant may comprise introducing to one or more cells of the plant a polynucleotide which decreases the expression of the polypeptide. In one embodiment, the polynucleotide is selected from the group consisting of:
  i) an antisense polynucleotide which comprises the nucleic acid sequence according to SEQ ID NO: 15;
  ii) an antisense polynucleotide which comprises at least 15 contiguous nucleic acid residues selected from the nucleic acid sequence according to SEQ ID NO: 15;
  iii) an antisense polynucleotide which comprises at least 15 contiguous nucleic acid residues from a polynucleotide which is complementary to a nucleic acid sequence which encodes a polypeptide which comprises an amino acid sequence with at least 70% sequence identity to the amino acid sequence according to SEQ ID NO: 1;
  iv) an RNA interference polynucleotide which comprises a nucleic acid sequence comprising at least 9 contiguous nucleic acid residues selected from a nucleic acid sequence which is complementary to a polynucleotide consisting of the nucleic acid sequence according to SEQ ID NO: 15; and
  v) an antisense polynucleotide which consists of the nucleic acid sequence according to SEQ ID NO: 15.

In one embodiment, the polypeptide comprises an amino acid sequence which has at least 80% sequence identity to the amino acid sequence according to SEQ ID NO: 1 and which is capable of modulating cytokinin signaling in the plant. In another embodiment, the polypeptide comprises an amino acid sequence which has at least 85% sequence identity to the amino acid sequence according to SEQ ID NO: 1 and which is capable of modulating cytokinin signaling in the plant. In yet another embodiment, the polypeptide comprises an amino acid sequence which has at least 90% sequence identity to the amino acid sequence according to SEQ ID NO: 1 and which is capable of modulating cytokinin signaling in the plant. In yet a further embodiment, the polypeptide comprises an amino acid sequence which has at least 95% sequence identity to the amino acid sequence according to SEQ ID NO: 1 and which is capable of modulating cytokinin signaling in the plant.

In one embodiment, there is provided a method as defined above wherein the step of modulating the expression of the polypeptide comprises increasing the expression of the polypeptide. The step of increasing the expression of the polypeptide by the plant may comprise introducing to one or more cells of the plant a polynucleotide which increases the expression of the polypeptide. In one embodiment, the polynucleotide is selected from the group consisting of:
  i) a polynucleotide which comprises a nucleic acid sequence which encodes a polypeptide of SEQ ID NO: 1,
  ii) a polynucleotide which encodes a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant; and
  iii) a polynucleotide which encodes a polypeptide which comprises an amino acid sequence with at least 70% sequence identity to the amino acid sequence according to SEQ ID NO: 1 and which is capable of modulating cytokinin signaling in the plant.

In certain embodiments, the polypeptide encoded by the polynucleotide in part ii) comprises an intracellular signaling domain. In certain embodiments, the polypeptide encoded by the polynucleotide in part ii) comprises an extracellular cytokinin binding domain.

In one embodiment, the at least one trait in a plant is selected from the group consisting of any one or more of plant height, plant biomass, apical bud development, branching, fertility, flowering, leaf area, senescence, seed germination, seed yield, seed weight, stem development, grain yield, tiller number, floral meristem development and root development.

In one embodiment, the decreased expression of the polypeptide as defined above leads to changes in the expression of traits in the plant including, but not limited to any one or more of increased branching, increased seed yield, increased plant biomass, increased grain yield, increased number of tillers, increased leaf area, delayed seed germination, decreased apical dominance, and delayed flowering, or combinations thereof in the plant when compared to a plant of the same type in which the expression of the polypeptide has not been modulated.

In another embodiment, the increase in expression of the polypeptide modulates at least one trait selected from the group consisting of any one or more of early flowering, dwarfism, decreased number of leaves, early senescence, early seed germination, delayed and reduced formation of rosette leaves, increased seedling root growth, or combinations thereof in the plant, relative to a plant of the same type in which the expression of the polypeptide has not been modulated.

Increase in plant biomass may be useful in increasing the yield and quality in leafy vegetables. Increased branching and biomass accumulation may also be useful in production of fodder grass and various cereal crops. Increase in plant biomass may result in an abundance of cellulosic ethanol (such as bioethanol), which can be used as a source of biofuel.

The increase in plant biomass is also expected to facilitate more efficient administration of plant fertilizers. Therefore, the increase in plant biomass may prevent environmental problems such as fertilizer runoffs that may lead to a range of environmental problems such as algae bloom.

Furthermore, the increased expression of the polypeptide may lead to early flowering in plants such as sugarcane. This may be useful for commercial cultivars as it can help plant breeders in conventional plant breeding practices. Similarly, the dwarfism phenotype as a result of the increased expression of the polypeptide may also be desirable in the generation of ornamental plants.

In a second aspect, there is provided an isolated polynucleotide selected from the group consisting of:
  i) an antisense polynucleotide which comprises the nucleic acid sequence according to SEQ ID NO: 15,
  ii) an antisense polynucleotide which comprises at least 15 contiguous nucleic acid residues selected from the nucleic acid sequence according to SEQ ID NO: 15; and
  iii) an antisense polynucleotide which comprises at least 15 contiguous nucleic acid residues from a polynucleotide which is complementary to a nucleic acid sequence which encodes a polypeptide which comprises an amino acid sequence with at least 70% sequence identity to the amino acid sequence according to SEQ ID NO: 1;
  iv) an RNA interfering polynucleotide comprising a nucleic acid sequence which comprises at least 9 contiguous nucleic acid residues selected from the nucleic acid sequence according to SEQ ID NO: 15; and v) an antisense polynucleotide which consists of the nucleic acid sequence according to SEQ ID NO: 15;

wherein the polynucleotide is capable of decreasing the expression of a polypeptide which modulates at least one trait in a plant, or vi) a polynucleotide which is complementary to any one of i) to v), or vii) a polynucleotide which hybridizes under stringent conditions to any one of i) to v).

According to a third aspect, there is provided an isolated polynucleotide selected from the group consisting of:
 i) a polynucleotide which comprises a nucleic acid sequence which encodes a polypeptide of SEQ ID NO: 1;
 ii) a polynucleotide which encodes a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant;
 iii) a polynucleotide which encodes a polypeptide which comprises an amino acid sequence with at least 70% sequence identity to the amino acid sequence according to SEQ ID NO: 1 and which is capable of modulating cytokinin signaling in the plant; and
 iv) a polynucleotide which consists of a nucleic acid sequence which encodes a polypeptide of SEQ ID NO: 1;

wherein the polynucleotide is capable of increasing the expression of a polypeptide which modulates at least one trait in a plant, or
 v) a polynucleotide which is complementary to any one of i) to iv); or
 vi) a polynucleotide which hybridizes under stringent conditions to any one of i) to iv).

According to a fourth aspect, there is provided a vector comprising a polynucleotide according to the second or the third aspect.

According to a fifth aspect, there is provided a host cell transformed with a polynucleotide according to the second or the third aspect, or a vector according to the fourth aspect.

According to a sixth aspect, there is provided a plant comprising a host cell according to the fifth aspect.

According to a seventh aspect, there is provided a method of producing a transgenic plant comprising the steps of:
 a) providing a polynucleotide that modulates the expression of a polypeptide, wherein the polypeptide is selected from the group consisting of:
  i) a polypeptide which comprises the amino acid sequence according to SEQ ID NO: 1;
  ii) a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant;
  iii) a polypeptide which comprises an amino acid sequence with at least 70% sequence identity to the amino acid sequence according to SEQ ID NO: 1 and which is capable of modulating cytokinin signaling in the plant; and
  iv) a polypeptide which consists of an amino acid sequence according to SEQ ID NO: 1;
 b) transforming a plant, plant part or plant cell with the polynucleotide of step (a), and
 c) growing the transformed plant, plant part or plant cell to produce the transgenic plant.

In one embodiment, the polynucleotide in step (a) of the seventh aspect comprises an isolated polynucleotide selected from the group consisting of:
 i) an antisense polynucleotide which comprises the nucleic acid sequence according to SEQ ID NO: 15,
 ii) an antisense polynucleotide which comprises at least 15 contiguous nucleic acid residues selected from the nucleic acid sequence according to SEQ ID NO: 15; and
 iii) an antisense polynucleotide which comprises at least 15 contiguous nucleic acid residues from a polynucleotide which is complementary to a nucleic acid sequence which encodes a polypeptide which comprises an amino acid sequence with at least 70% sequence identity to the amino acid sequence according to SEQ ID NO: 1;
 iv) an RNA interfering polynucleotide comprising a nucleic acid sequence which comprises at least 9 contiguous nucleic acid residues selected from the nucleic acid sequence according to SEQ ID NO: 15; and
 v) an antisense polynucleotide which consists of the nucleic acid sequence according to SEQ ID NO: 15;

wherein the polynucleotide is capable of modulating the expression of a polypeptide which modulates at least one trait in a plant, or
 vi) a polynucleotide which is complementary to any one of i) to v), or
 vii) a polynucleotide which hybridizes under stringent conditions to any one of i) to v).

In another embodiment, the polynucleotide in step (a) of the seventh aspect comprises an isolated polynucleotide selected from the group consisting of:
 i) a polynucleotide which comprises a nucleic acid sequence which encodes a polypeptide of SEQ ID NO: 1,
 ii) a polynucleotide which encodes a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant;
 iii) a polynucleotide which encodes a polypeptide which comprises an amino acid sequence with at least 70% sequence identity to the amino acid sequence according to SEQ ID NO: 1 and which is capable of modulating cytokinin signaling in the plant; and
 iv) a polynucleotide which consists of a nucleic acid sequence which encodes a polypeptide of SEQ ID NO: 1, wherein the polynucleotide is capable of increasing the expression of a polypeptide which modulates at least one trait in a plant, or v) a polynucleotide which is complementary to any one of i) to iv), or vi) a polynucleotide which hybridizes under stringent conditions to any one of i) to iv).

In one embodiment of the method according to the seventh aspect, the growing in step (c) is by culturing the transformed plant, plant part or plant cell under conditions which may permit growth of the transformed plant, plant part or plant cell. In certain embodiments, the plant part is selected from the group consisting of any one or more of root, stem, leaf, bud, flower, shoot, seed and branch.

In one embodiment, there is provided a plant according to the sixth aspect, wherein the plant is a monocotyledonous plant. In another embodiment, there is provided a plant according to the sixth aspect, wherein the plant is a dicotyledonous plant.

In certain embodiments, the plant is selected from the group consisting of any one or more of oat, barley, wheat, rye, corn, rice, sorghum, millet, amaranth, reed grass, sweet grass, cane, bamboo, fodder grass, diamond grass and turf grass.

According to an eighth aspect, there is provided a transgenic plant when produced by the method according to the seventh aspect, wherein the plant is selected from the group consisting of any one or more of oat, barley, wheat, rye, corn, rice, sorghum, millet, amaranth, reed grass, sweet grass, cane, bamboo, fodder grass, diamond grass and turf grass.

In one embodiment, the transgenic plant is capable of producing fertile plants.

According to a ninth aspect, there is provided a part or a seed of a plant as defined above. The part may be selected from the group consisting of any one or more of root, stem, leaf, bud, flower, shoot, seed and branch.

According to a tenth aspect, there is provided a plant or propagating material thereof regenerated from a plant as defined above, or a part or a seed as defined above.

According to an eleventh aspect, there is provided use of a plant transformed with a polynucleotide as defined above for plant biomass production. In certain embodiments, the plant is selected from the group consisting of any one or more of oat, barley, wheat, rye, corn, rice, sorghum, millet, amaranth, reed grass, sweet grass, cane, bamboo, fodder grass, diamond grass and turf grass.

According to a twelfth aspect, there is provided use according to the eleventh aspect, wherein the plant biomass production is for biofuel production.

According to a thirteenth aspect, there is provided an isolated polypeptide selected from the group consisting of:

i) a polypeptide which comprises the amino acid sequence according to SEQ ID NO: 1;

ii) a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in a plant;

iii) a polypeptide which comprises an amino acid sequence with at least 70% sequence identity to the amino acid sequence according to SEQ ID NO: 1 and which is capable of modulating cytokinin signaling in a plant; and iv) a polypeptide which consists of an amino acid sequence according to SEQ ID NO: 1, wherein the modulation of the expression of the polypeptide modulates the expression of at least one trait in the plant.

DEFINITIONS

The following words and terms used herein shall have the meaning indicated:

The term "contiguous" as used herein refers to a continuous or an unbroken series of amino acid residues or nucleic acid residues present in a polypeptide or polynucleotide, respectively. For example, "contiguous amino acid residues" will be understood to include a contiguous amino acid sequence of at least about 4, about, 5, about 6, about 7, about 8, about 9, about 10, about 12, about 15, about 20, about 25, about 30, about 40, about 50, about 75, about 100, about 150, about 200, about 250, about 300, about 350 or about 400, about 450, or about 485 amino acids or so. Similarly, "contiguous nucleic acid residues" will be understood to include a contiguous nucleic acid sequence of at least about 12, about, 15, about 18, about 21, about 24, about 27, about 30, about 36, about 45, about 60, about 75, about 90, about 120, about 150, about 225, about 300, about 450, about 600, about 750, about 900, about 1050, about 1200, about 1350, about 1450, about 1550, about 1650, or about 1775 nucleotides or so.

The term "cytokinin signaling" refers to the molecules that propagate an extracellular signal through the cell membrane to become an intracellular signal. This signal can then stimulate a cellular response. The polypeptide molecules involved in cytokinin signaling processes are typically receptor and non-receptor protein kinases, receptor and non-receptor protein phosphatases, and transcription factors. The cytokinin signaling activity can be measured by measuring the cytokinin levels expressed in plants or by measuring the binding activity between the cytokinin and the polypeptide molecules involved in the cytokinin signaling processes.

The term "hybridization" when used with reference to nucleic acids refers to the process in which two single-stranded polynucleotides bind non-covalently to form a stable double-stranded polynucleotide. The term "hybridization" may also refer to triple-stranded hybridization. The resulting double- or triple-stranded polynucleotide is a "hybrid". The proportion of the population of polynucleotides that forms stable hybrids is referred to herein as the "degree of hybridization." Hybridization and the strength of hybridization (i.e., the strength of the association between the nucleic acids) is dependent on factors such as the degree of complementary between the nucleic acids, stringency of the conditions involved, the thermal melting point (Tm) of the formed hybrid, and the G:C ratio within the nucleic acids as discussed in detail further below.

The term "primer" as used herein refers to a polymer of nucleotides capable of acting as a point of initiation of DNA synthesis when annealed to a nucleic acid template under conditions in which synthesis of a primer extension product is initiated, i.e., in the presence of four different nucleotide triphosphates and a polymerase in an appropriate buffer (which typically includes a pH buffer and cofactors) and at a suitable temperature. The primers used in the amplification steps of the invention may be fully complementary or substantially complementary to the target sequences.

The terms "trait" and "phenotype" are used interchangeably and encompass any characteristic, especially one that distinguishes one plant from another. Exemplary traits include any one or more of plant height, plant biomass, degree of apical bud development, degree of branching, plant, seed or pollen fertility, number or onset of flowering, leaf area, onset of senescence, onset of seed germination, seed yield, total or individual seed weight, degree of stem development, grain yield, tiller number, degree of floral meristem development and degree of root development.

The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (DNA or RNA) into a target cell or integration of the transgene into a chromosome of a target cell by way of human intervention, such as by the methods described herein.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically+/−4% of the stated value, more typically+/−3% of the stated value, more typically, +/−2% of the stated value, even more typically+/−1% of the stated value, and even more typically+/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

In the context of ranges describing amino acid residues in a polypeptide or nucleic acid residues in a polynucleotide it is to be understood that the description of a range includes the first and last numerical values of the range. Additionally in this context, the description of a range is not intended to encompass individual amino acid or nucleic acid residues which fall within the range. For example, the description of a range, for instance "from amino acid 1 to amino acid 7", should be considered to refer to an amino acid sequence which spans and includes the amino acids at positions 1, 2, 3, 4, 5, 6, and 7, but which does not to refer to any one or more individual amino acids which lie within that range, for example, amino acid 1 only, amino acid 2 only, amino acids 1 and 2, or so on.

DETAILED DISCLOSURE OF EMBODIMENTS

Exemplary, non-limiting embodiments of a new method for modulating the expression of a trait in a plant, as well as materials for use in and produced by the new method, will now be disclosed.

The present invention is based on the identification that the polypeptide comprising the amino acid sequence according to SEQ ID NO: 1 is involved in the cytokinin-signaling pathway in plants.

Cytokinins are a class of plant hormones that regulate plant growth and development in a variety of ways. They are active in promoting cell division, cell growth and differentiation and other growth regulatory functions in a plant. Cytokinins are believed to play an important role in all phases of plant development from cell division and enlargement to the formation of flowers and fruits. For example, cytokinins are capable of promoting the elongation of buds and the growth of leaves, and of inhibiting senility, accumulation of amino acids and opening of the stoma.

The basic structure of a cytokinin comprises a 6-amino purine, of which the amino group is modified with a substituent usually carrying 5 carbon atoms. The naturally occurring active cytokinins in higher plants are mainly zeatin and isopentenyl adenine derived from biosynthetic precursors. Elevated cytokinin levels are associated with the development of seeds in higher plants, as these have been demonstrated to coincide with maximal mitotic activity in the endosperm of developing maize kernels and other cereal grains.

The basic molecular mechanisms of cytokinin biosynthesis and signal transduction became clear only recently. Three members of the cytokinin receptor family, which are sensor histidine kinases, have been identified and have functions that are similar to the bacterial two-component signal transduction pathways involving phosphorelay mechanisms. These three cytokinin receptors, AHK2, AHK3 and CRE1/AHK4, show a high degree of sequence identity, but each has distinguishing characteristics and is required for normal cytokinin perception and plant growth. While mutational analysis has been performed on these three receptors, mutations in any one of the three receptors have not resulted in significant alteration of the plant phenotypes. In contrast, mutations in all three receptors (i.e., a triple mutant) resulted in dwarfed and sterile plants. These phenotypes were not seen in the antisense mutants of the present invention as described below.

In the *Arabidopsis* cytokinin signaling pathway, histidine protein kinases (AHKs) serve as cytokinin receptors and transmit signals from AHKs to nuclear response regulators (ARRs) via histidine phosphotransfer proteins (AHPs). The AHPs shuttle from the cytoplasm to the nucleus in a cytokinin-dependent manner and send signals to ARRs in the nucleus, which can activate or repress transcription of genes involved in plant growth and development within the plant cell.

Disclosed herein is an isolated polypeptide, HOG1 (comprising the amino acid sequence set forth in SEQ ID NO: 1), purified from the *Arabidopsis thaliana* plant, which binds to cytokinins with high affinity. Furthermore, the present inventors have identified that the modulation of the expression of the polypeptide according to SEQ ID NO: 1 modulates the cytokinin signaling pathway in both monocotyledonous and dicotyledonous plants, resulting in the expression of different traits in plants, despite lacking the histidine kinase domain. In some embodiments, the disclosed polypeptide also lacks SAHH activity.

In certain embodiments, the disclosed polypeptide comprises a transmembrane domain.

Thus, the present invention provides a method of modulating the expression of at least one trait in a plant, comprising the step of modulating the expression of at least one polypeptide by the plant, wherein the polypeptide is selected from the group consisting of:

i) a polypeptide which comprises the amino acid sequence according to SEQ ID NO: 1;

ii) a polypeptide which comprises an amino acid sequence which is selected from the group consisting of any one or more of from amino acid 1 to amino acid 7, from amino acid 9 to amino acid 230, from amino acid 1 to amino acid 58, from amino acid 77 to amino acid 485, from amino acid 59 to amino acid 76, from amino acid 150 to amino acid 191, from amino acid 231 to amino acid 405, and from amino acid 406 to amino acid 438 of SEQ ID NO: 1, or at equivalent positions in a homologue thereof, and which is capable of modulating cytokinin signaling in the plant;

iii) a polypeptide which comprises an amino acid sequence with at least 70% sequence identity to the amino acid sequence according to SEQ ID NO: 1 and which is capable of modulating cytokinin signaling in the plant; and iv) a polypeptide which consists of an amino acid sequence according to SEQ ID NO: 1, wherein the modulation of the expression of the polypeptide modulates the expression of at least one trait in the plant.

The signaling pathway of any cytokinin may be modulated using the method of the present invention. There are more than 200 natural and synthetic cytokinins that are known to-date (Arteca, Plant Growth Substances: Principles and Applications, New York: Chapman & Hall (1996); Salisbury and Ross, *Plant Physiology* pp. 357-407, 531-548 (1992)). Exemplary naturally occurring cytokinins include zeatin, kinetin, isopentenyladenine and 6-Benzylaminopurine while phenylureas such as diphenylurea represent an exemplary class of synthetic cytokinins. Conjugated forms of cytokinins which can be produced in a number of ways are also known and included within the scope of the invention. For example, glucosides can be formed by the attachment of carbon 1 of glucose to the hydroxyl group on the side chain of zeatin or the carbon 1 can attach to the N atom of the C—N bond at either position 7 or 9 on the adenine ring.

The disclosed method may furthermore be applied to any plant in which the modulation of one or more traits is desired. The term "plant" as used herein also encompasses whole plants, ancestors and progeny of the plants and plant parts, including seeds, shoots, stems, leaves, roots (including tubers), flowers, and tissues and organs, wherein each of the aforementioned comprise the polynucleotide or polypeptide of the invention. The term "plant" also encompasses plant cells, suspension cultures, callus tissue, embryos, meristematic regions, gametophytes, sporophytes, pollen, and microspores, again wherein each of the aforementioned comprise the polynucleotide of interest.

Plants that are particularly useful in the methods of the invention include all monocotyledonous and dicotyledonous plants such as food crops, grasses, fodder or forage legumes, ornamental plants, trees, or shrubs as well as plants used for cellulosic biomass for ethanol (biofuel) production selected from the list comprising *Acer* spp., *Actinidia* spp., *Agropyron* spp., *Allium* spp., *Amaranthus* spp., *Ananas comosus*, *Annona* spp., *Apium* spp., *Arabidopsis thaliana*, *Arachis* spp, *Artocarpus* spp., *Asparagus officinalis*, *Avena sativa*, *Averrhoa carambola*, *Benincasa hispida*, *Bertholletia excelsea*, *Beta vulgaris*, *Brassica* spp., *Cadaba farinosa*, *Camellia sinensis*, *Canna indica*, *Capsicum* spp., *Carica papaya*, *Carissa macrocarpa*, *Carthamus tinctorius*, *Carya* spp., *Castanea* spp., *chrysanthemum*, *Cichorium endivia*, *Cinnamomum* spp., *Citnillus lanatus*, *Citrus* spp., *Cocos* spp., *Coffea* spp., *Cola* spp., *Colocasia esculenta*, *Corylus* spp., *Crataegus* spp., *Cucumis* spp., *Cucurbita* spp., *Cynara* spp., *Daucus carota*, *Desmodium* spp., *Dimocarpus longan*, *Dioscorea* spp., *Diospyros* spp., *Echinochloa* spp., *Eleusine coracana*, *Eriobotrya japonica*, *Eugenia uniflora*, *Fagopyrum* spp., *Fagus* spp., *Ficus carica*, *Fortunella* spp., *Fragaria* spp., *Ginkgo biloba*, *Glycine* spp., *Gossypium hirsutum*, *Helianthus* spp., *Hibiscus* spp., *Hordeum* spp., *Ipomoea batatas*, *Juglans* spp., *Lactuca sativa*, *Lathyrus* spp., *Lemna* spp., *Lens culinaris*, *Linum usitatissimum*, *Litchi chinensis*, *Lolium perenne*, *Lotus* spp., *Luffa acutangula*, *Lupinus* spp., *Macrotyloma* spp., *Malpighia emarginata*, *Malus* spp., *Mammea americana*, *Mangifera indica*, *Manihot* spp., *Manilkara zapota*, *Medicago sativa*, *Melilotus* spp., *Mentha* spp., *Momordica* spp., *Morus nigra*, *Musa* spp., *Nicotiana* spp., *Olea* spp., *Opuntia* spp., *Ornithopus* spp., *Oryza* spp., *Panicum miliaceum*, *Passiflora edulis*, *Pastinaca sativa*, *Persea* spp., *Petroselinum crispum*, *Petunia hybrida*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Rubus* spp., *Saccharum* spp., *Sambucus* spp., *Secale cereale*, *Sesamum* spp., *Solanum* spp., *Sorghum bicolor*, *Spinacia* spp., *Syzygium* spp., *Tamarindus indica*, *Theobroma cacao*, *Trifolium* spp., *Triücosecale rimpaui*, *Triticum* spp., *Vaccinium* spp., *Vicia* spp., *Vigna* spp., *Vitis* spp., *Zea mays*, *Zizania palustris*, *Ziziphus* spp., amongst others.

In one embodiment, the plant is a grain crop such as rice, wheat, maize, soybean, millet, barley, rye, oats, or sorghum. In another embodiment, the plant is a grass such as reed grass, sweet grass, cane, bamboo, fodder grass, diamond grass and turf grass. In yet another embodiment, the plant is a vegetable such as *Brassica alboglabra*, artichoke, asparagus, broccoli, Brussels sprouts, cabbage, canola, carrot, cauliflower, celery, collard greens, flax, kale, and lentil, or other plants having commercial or scientific value (such as *Arabidopsis thaliana*, *Petunia hybrida*, *chrysanthemum* etc.).

As discussed below in Examples 1 and 2, the disclosed methods have been demonstrated in both monocotyledonous and dicotyledonous plants. Hence, because the sequence of the polypeptide of SEQ ID NO: 1 is highly conserved amongst plant species, it is expected that the disclosed methods would be applicable to both monocotyledonous and dicotyledonous plants. For instance, as the disclosed methods have been demonstrated in rice (*Oryza sativa*) as described in Example 2 below, it would be expected to be applicable to other monocotyledonous plants, such as wheat (*Triticum aestivum*) (SEQ ID NO: 7) which has a 95% amino acid sequence identity to rice (SEQ ID NO: 5). Similarly, as the disclosed methods have been demonstrated on *Arabidopsis thaliana* as described in Example 1 below, it would be expected to be applicable to other dicotyledonous plants, such as *Petunia hybrida* (SEQ ID NO: 13) which has a 88% amino acid sequence identity to *Arabidopsis thaliana* (SEQ ID NO: 1), and *chrysanthemum* (SEQ ID NO: 9) which has a 92% amino acid sequence identity to *Arabidopsis thaliana* (SEQ ID NO: 1).

The term "expression" as used herein may refer to the expression of a trait, a gene, or a gene product, including the encoded polypeptide, in a plant.

Plant traits that may be modulated by the disclosed method include, but are not limited to, plant height, plant biomass, apical bud development, branching, fertility, flowering, leaf area, senescence, seed germination, seed yield, seed weight, stem development, grain yield, tiller number, floral meristem development and root development. According to one embodiment, the expression of a trait in a plant may be modulated to exhibit increased branching, increased seed yield, increased plant biomass, increased grain yield, increased number of tillers, increased leaf area, delayed seed germination, decreased apical dominance, delayed flowering, or combinations thereof, relative to a plant of the same type in which the expression of the polypeptide has not been modulated. In another embodiment, the expression of a trait in a plant may be modulated to exhibit early flowering, dwarfism, decreased number of leaves, early senescence, early seed germination, delayed and reduced formation of rosette leaves, increased seedling root growth, or combinations thereof, relative to a plant of the same type in which the expression of the polypeptide has not been modulated.

In particular, seed yield and plant biomass were significantly increased by about 2 to about 5 folds for plants in which the expression of the polypeptide according to SEQ ID NO: 1 has been decreased relative to that of a plant of the same type without the decreased expression of the polypeptide. Depending on the type of plant, the modulation in the expression of the polypeptide according to SEQ ID NO: 1, and the extent of the modulation, the seed yield and plant biomass may respectively be expected to increase by about 2 folds, about 2.5 folds, about 3 folds, about 3.5 folds, about 4 folds, about 4.5 folds or about 5 folds.

Similarly, grain yield and number of tillers were increased by about 2 to about 4 folds for plants in which the expression of the polypeptide according to SEQ ID NO: 1 has been decreased relative to that of a plant of the same type without the decreased expression of the polypeptide. Depending on the type of plant, the modulation in the expression of the polypeptide according to SEQ ID NO: 1, and the extent of the modulation, the grain yield and number of tiller may respectively be expected to increase by about 2 folds, about 2.5 folds, about 3 folds, about 3.5 folds, or about 4 folds.

In particular embodiments, leaf area was also significantly increased by about 2 to about 6 folds for plants in which the expression of the polypeptide according to SEQ ID NO: 1 has been decreased relative to that of a plant of the same type without the decreased expression of the polypeptide. Depending on the type of plant, the modulation in the expression of the polypeptide according to SEQ ID NO: 1, and the extent of the modulation, the leaf area may be expected to increase by about 2 folds, about 2.5 folds, about 3 folds, about 3.5 folds, about 4 folds, about 4.5 folds, about 5 folds, about 5.5 folds, or about 6 folds.

For plants in which the expression of the polypeptide according to SEQ ID NO: 1 has been increased, flowering was advanced by about 5 to about 15 days relative to a plant of the same type without the increased expression of the polypeptide. As discussed above, the modulation in flowering time would depend on the type of plant, the modulation in the expression of the polypeptide according to SEQ ID NO: 1, and the extent of the modulation, but would typically be advanced by about 4 days, about 5 days, about 6 days, about 7 days, about 8 days, about 9 days, about 10 days, about 11 days, about 12 days, about 13 days, about 14 days, or about 15 days.

In certain embodiments, the fertility of the plants is not modulated and the transformed plants are capable of producing fertile plants.

Expression of a trait may be determined using various methods known in the art. Leaf area, for example, may be determined by measuring the total leaf area as leaf area ratio (LAR), leaf area index (LAI) or specific leaf area (SLA) using the following equations, respectively:

$$LAR(m^2g^{-1} \text{ or } m^2kg^{-1}) = (\text{total leaf area})/(\text{total dry weight})$$

$$LAI = \frac{(\text{total leaf area of the crop})}{(\text{total ground area upon which it stands})}$$

$$SLA(m^2g^{-1}) = (\text{leaf area})/(\text{leaf dry mass})$$

Alternatively, leaf area may be measured using computer based image analysis.

The seed yield may also be measured in several ways, for example as an increase or decrease of thousand kernel weight, as an increase or decrease of the number of filled seeds, as total seed weight, as seed size, or as harvest index.

Differences in plant height can be measured by direct measurements and comparison with the heights of the unmodified control plants.

Plant biomass can be determined by weighing the freshly harvested plants (fresh weight or wet weight) or the constant dry weight. Dry weight can be determined after drying the harvested plant or plant parts of interest (e.g., leaves, seed) in a drying oven set at about 80° C. for 2 days to 7 days until constant weight is recorded (dry weight). Similarly, seed or grain weight and total seed or grain yield per plant or per unit area of cultivation (e.g., per square meter, acre or hectare) can be determined.

Changes in apical bud development and branching as well as fertility, flowering, and senescence can be estimated by comparing the development of the modified plants (e.g., genetically modified as described in this disclosure) with the appearance of the unmodified plants at the same stage of growth.

Tiller number (or number of branches) per plant can be determined by counting a representative sample of plants grown until all tillers have developed (e.g., in rice cultivars it may take about 2 months before tillering reaches maximum number). These can be compared to the tiller number per plant of the unmodified plants.

Floral meristem development and root development can be examined at both macroscopic level (for example by visual observations at comparable stages of development) as well as by microscopy (for example by light or electron microscopy) for differences in cell arrangement etc.

Expression of a gene may be determined, for example, by measuring the production of messenger RNA (mRNA) transcript levels. Expression of a polypeptide gene product may be determined, for example, by immunoassay using an antibody(ies) that bind with the polypeptide.

The term "modulate" refers to a change in the expression of a trait, a gene, or a gene product, including the encoded polypeptide, in a plant. Typically, the change is relative to a plant of the same type in which the expression of the trait, gene or polypeptide has not been modulated. For example, when used with reference to the expression of a trait, the term "modulate" may refer to increased or decreased plant height, increased or decreased plant biomass, increased or decreased apical bud development, increased or decreased branching, increased or decreased fertility, increased or decreased flowering, increased or decreased leaf area, early or delayed senescence, early or delayed seed germination, increased or decreased number of seeds, increased or decreased seed yield, increased or decreased seed weight, early or delayed stem development, increased or decreased stem development, increased or decreased grain yield, increased or decreased tiller number, increased or decreased floral meristem development, early or delayed floral meristem development, increased or decreased root development, early or delayed root development, and the like, in a plant in which the expression of the polypeptide has been modulated using the disclosed method relative to a plant of the same type in which the expression of the polypeptide has not been modulated. In one embodiment, the modulated trait may be increased branching, increased seed yield, increased plant biomass, increased grain yield, increased number of tillers, increased leaf area, delayed seed germination, decreased apical dominance, delayed flowering, or combinations thereof, in a plant in which the expression of the polypeptide has been modulated using the disclosed method relative to a plant of the same type in which the expression of the polypeptide has not been modulated. In other embodiments, the modulated trait may be early flowering, dwarfism, decreased number of leaves, early senescence, early seed germination, delayed and reduced formation of rosette leaves, increased seedling root growth, or combinations thereof, in a plant in which the expression of the polypeptide has been modulated using the disclosed method relative to a plant of the same type in which the expression of the polypeptide has not been modulated.

By "development", it is meant the process by which the plant or plant part grows, via cell growth and differentiation, to reach maturity.

When used with reference to the expression of a gene or gene product, the term "modulate" typically refers to an increase or a decrease in the level of expression. In some embodiments, the decrease in the level of expression of the gene or gene product includes complete inhibition of the expression of the gene or gene product. In certain embodiments, the decrease in the level of expression of the gene or gene product is not a complete inhibition of the expression of the gene or gene product.

In some embodiments, when the level of expression of the HOG1 polypeptide (SEQ ID NO: 1) is increased by about 3- to about 20-folds when compared to the wild type, the level of cytokinin is decreased by about 20 to about 85 percent, about 30 to about 75 percent, about 40 to about 65 percent, or about 50 to about 55 percent. This decrease in cytokinin level may result in modulation of the expression of traits such as advanced seed germination by about 4 to 5 about days, growth retardation, and delayed formation and expansion of new rosette leaves. In other embodiments, when the level of expression of the HOG1 polypeptide (SEQ ID NO: 1) is decreased by about 2- to about 10-folds when compared to the wild type, the level of cytokinin is increased by about 20 to about 85 percent, about 30 to about 75 percent, about 40 to about 65 percent, or about 50 to about 55 percent. This increase in cytokinin level may result in modulation of the expression of traits such as delayed seed germination by about 5 days. As can be seen from the Examples below, the expression of traits is related to the level of expression of the cytokinin. Methods for increasing or decreasing the level of expression of the gene or gene product are also discussed further below.

Alternatively, the term "modulate" may refer to a change in the biological or functional properties of a gene or a gene product, including the encoded polypeptide, in the plant. For example, modulation may cause a change in the binding affinity of the encoded polypeptide. In certain embodiments, modulation does not cause a change in the nucleic acid sequence of the gene or the amino acid sequence of the encoded polypeptide.

Typically, the expression of one or more traits in a plant is modulated by modulating the expression of a polypeptide comprising the amino acid sequence according to SEQ ID NO: 1. "Polypeptide", "peptide" and "protein" are used interchangeably herein to refer to a polymer of amino acid residues (dipeptide or greater) according to SEQ ID NO: 1 linked through peptide bonds or modified peptide bonds, and to variants and synthetic analogues of the same. Thus, these terms include amino acid polymers according to SEQ ID NO: 1 in which one or more amino acid residues is a synthetic non-naturally occurring amino acid, such as a chemical analogue of a corresponding naturally occurring amino acid, as well as to naturally-occurring amino acid polymers. Polypeptides of the present invention include, but are not limited to, naturally purified products, products of chemical synthetic procedures, and products produced by recombinant techniques from a prokaryotic or eukaryotic host, including, for example, bacterial, yeast, higher plant, insect and mammalian cells. The polypeptides of the invention may comprise non-peptidic components, such as carbohydrate groups. Carbohydrates and other non-peptidic substituents may be added to a polypeptide by the cell in which the polypeptide is produced, and will vary with the type of cell. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell. Polypeptides are defined herein, in terms of their amino acid backbone structures; substituents such as carbohydrate groups are generally not specified, but may be present nonetheless. In addition, polypeptides of the invention may also include an initial modified methionine residue, in some cases as a result of host-mediated processes. Proteins may be present as monomeric or as multimeric proteins e.g. as dimers (homo or heterodimers) or trimers.

Typically, the polypeptide the expression of which is to be modulated in the present invention includes within its scope a variant or fragment thereof, wherein the variant or fragment has biological activity which is functionally the same as the polypeptide defined in SEQ ID NO:1. In certain embodiments, the biological activity is cytokinin binding and receptor activity. Receptor activity involves the propagation of an extracellular signal through the cell membrane to become an intracellular signal which can initiate one or more cellular responses upon binding of the cytokinin to the receptor. Methods for identifying cytokinin binding and receptor activity are well known in the art and are described in Examples 1 and 2 below.

The fragments may contain single or multiple amino acid deletions from either terminus of the polypeptide or from internal stretches of the primary amino acid sequence. The fragments preferably comprise at least n consecutive amino acids from the parent sequence and, depending on the particular sequence, n is preferably 7 or more (for example, 7, 8, 9, 10, 12, 15, 17, 20, 30, 40, 50, 60, 70, 80, 90, 100, 150, 200, 300, 400 or more).

In one embodiment, n is 7.
In one embodiment, n is 18.
In one embodiment, n is 33.
In one embodiment, n is 42.
In one embodiment, n is 58.
In one embodiment, n is 175.
In one embodiment, n is 222.
In one embodiment, n is 409.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. Additionally, several fragments may be comprised within a single larger polypeptide.

The invention also includes functional equivalents of a polypeptide comprising an amino acid sequence according to SEQ ID NO: 1. The polypeptide fragments and functional equivalents of the invention retain the biological activity of the parent polypeptide, i.e. the cytokinin binding and receptor activity. Methods for identifying cytokinin binding and receptor activity are well known in the art and are described in Examples 1 and 2 below.

The functionally-equivalent polypeptides of the invention include polypeptides that are homologous to a polypeptide as set forth in SEQ ID NO: 1. Two polypeptides are said to be "homologous" if the sequence of one of the polypeptides has a high enough degree of identity to the sequence of the other polypeptide. The phrases "percent identity", "% identity", "protein identity", "sequence identity" etc. as applied to polypeptide sequences, refer to the percentage of identical residue matches between at least two polypeptide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity may be determined using one or more computer algorithms or programs known in the art or described herein. Degrees of identity can be readily calculated by persons skilled in the art (see for example: Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Methods of measuring protein sequence identity are well known in the art and it will be understood by those of skill in the art that in the present context, sequence identity is calculated on the basis of amino acid identity (sometimes referred to as "hard homology"). For example, the UWGCG Package provides the BESTFIT program which can be used to calculate sequence identity (for example used on its default settings) (Devereux et al. (1984) Nucleic Acids Research 12, p 387-395). The PILEUP and BLAST (Basic Local Alignment Search Tool) algorithms can be used to calculate sequence identity or line up sequences (typically on their default settings), for example as described in Altschul S. F. (1993) J Mol Evol 36:290-300 and in Altschul, S, F et al. (1990) J Mol Biol 215:403.

Software for performing BLAST analyses is available from several sources, including the National Center for Biotechnology Information (NCBI), Bethesda, Md., and on the internet at, for example, the NCBI website. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased.

Thus, sequence identity, as referred to herein, can for instance be determined using BLAST version 2.1.3 (or other versions thereof) using the default parameters specified by the NCBI (the National Center for Biotechnology Information) [Blosum 62 matrix; gap open penalty=11 and gap extension penalty=1].

In certain embodiments, the default settings of the aforementioned algorithms/programs are used.

Typically, greater than 50% identity between two polypeptides is considered to be an indication of functional equivalence, provided that the activity of the reference polypeptide is retained. More preferred polypeptides have degrees of identity of greater than 61%, 62%, 63%, 64%, 65%, 66%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 1.

Using the program BLAST available from the NCBI, it was shown that the *Arabidopsis thaliana* HOG1 polypeptide of the invention (SEQ ID NO: 1) generally shares about 80 to 95% amino acid sequence identity to its homologue in rice (i.e., the OsCBP) (SEQ ID NO: 5), wheat (SEQ ID NO: 7), *chrysanthemum* (SEQ ID NO: 9) and *Petunia hybrida* (i.e., the PETCBP) (SEQ ID NO: 13). More specifically, the *Arabidopsis thaliana* HOG1 polypeptide (SEQ ID NO: 1) shares about 90% amino acid sequence identity with its homologue in rice (SEQ ID NO: 5), about 91% amino acid sequence identity with its homologue in wheat (SEQ ID NO: 7), about 92% amino acid sequence identity with its homologue in *chrysanthemum* (SEQ ID NO: 9), about 88% amino acid sequence identity with its homologue in *Petunia hybrida* (SEQ ID NO: 13), about 99% amino acid sequence identity with its homologue in *Brassica alboglabra* (SEQ ID NO: 11), about 90% amino acid sequence identity with its homologue in *Solanum tuberosum* (SEQ ID NO: 29) and about 89% amino acid sequence identity with its homologue in *Lycopersicon esculentum* (SEQ ID NO: 27).

Functionally-equivalent polypeptides according to the invention are intended to include polypeptides wherein at one or more positions there have been amino acid insertions, deletions, or substitutions, either conservative or non-conservative, provided that such changes result in a protein which retains the cytokinin binding and receptor activity of the parent polypeptide. Each of these types of changes may occur alone, or in combination with the others, one or more times in a given sequence. Such variants may for example be made using the methods of protein engineering and site-directed mutagenesis.

Fusion proteins may also be engineered to improve characteristics of the HOG1 protein, and its homologues, or variant or fragment thereof. For example, a region of additional amino acids, particularly charged amino acids, may be added to the N-terminus of the HOG1 protein, and its homologues, or variant or fragment thereof, to improve stability during purification from a host cell. Alternatively, peptide moieties may be added to the polypeptide to facilitate purification. Such regions may be removed prior to final preparation of the polypeptide. The addition of peptide moieties to facilitate handling of polypeptides are routine techniques well known to those of skill in the art.

The polypeptides of the invention may be prepared by a variety of methods, such as by purification from a plant and by recombinant methods. Polypeptides of the invention, particularly short peptide fragments, may also be produced by chemical synthesis such as by conventional liquid or solid phase synthesis techniques (see for example the methods described in Solid Phase Peptide Synthesis, 2nd ed., 1984 The Pierce Chemical Co., Rockford, Ill.). Alternatively, peptides can be produced by digestion of a polypeptide of the invention with proteinases such as endoLys-C, endoArg-C, endoGlu-C and *staphylococcus* V8-protease.

Purification of the polypeptides of the invention may be effected by any one, or a combination of, techniques such as size exclusion chromatography, ion-exchange chromatography and reverse-phase high performance liquid chromatography. In vitro detection of the polypeptides or variants or fragments thereof of the present invention may be achieved using a variety of techniques including ELISA (enzyme linked immunosorbent assay), Western blotting, immunoprecipitation, immunofluorescence, thin layer chromatography, reverse-phase high performance liquid chromatography, amino-acid analysis after acid hydrolysis and by fast atom bombardment (FAB) mass spectrometric analysis. Such techniques are commonly used by those of skill in the art.

Using methods that are known in the art, the polypeptide of the invention (SEQ ID NO: 1) was shown to comprise two conserved signatures of SAHH. In the second SAHH signature, three conserved glycine residues representing the dinucleotide-binding domain were identified. As cytokinins are nucleotide derivatives, it is predicted that these residues may form the cytokinin-binding domain. Putative transmembrane domains were also identified at amino acid positions 1 to 7 (at the N-terminal), positions 150 to 191 and positions 59 to 76 of SEQ ID NO: 1.

Other putative cytokinin binding domains were identified at amino acid positions 9 to 230 (at the N-terminal), positions 77 to 485 and positions 406 to 438 (at the C-terminal). A putative NAD$^+$-binding domain was identified at amino acid positions 231 to 405. An N-terminal intracellular domain was identified at amino acid positions 1-58.

In certain embodiments, the expression of the polypeptide in the plant is modulated by introducing to one or more cells of the plant a polynucleotide which modulates the expression of the polypeptide. The polynucleotide of the present invention may be in the form of RNA, such as mRNA, or in the form of DNA, including, for instance, cDNA and genomic DNA that may be obtained by cloning or that may be produced synthetically. The DNA may be double-stranded or single-stranded. Single-stranded DNA or RNA may be the coding strand, also known as the sense strand, or it may be the non-coding strand, also referred to as the anti-sense strand as discussed further below.

The polynucleotide suitable for use in the disclosed method may comprise nucleotides, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide may comprise sugars and phosphate groups, as may typically be found in RNA or DNA, or modified or substituted sugar or phosphate groups. The polynucleotide may also comprise modified nucleotides, such as methylated nucleotides and nucleotide analogs. The sequence of nucleotides may be interrupted by non-nucleotide components. Thus, the terms nucleoside, nucleotide, deoxynucleoside and deoxynucleotide generally include analogs having some structural features in common with a naturally occurring nucleoside or nucleotide such that when incorporated into a polynucleotide sequence, they allow hybridization with a naturally occurring polynucleotide sequence in solution. Typically, these analogs are derived from naturally occurring nucleosides and nucleotides by replacing and/or modifying the base, the ribose or the phosphodiester moiety. The changes may be tailor made to stabilize or destabilize hybrid formation or enhance the specificity of hybridization with a complementary polynucleotide sequence as desired.

The polynucleotide of the invention also includes within its scope a variant or fragment of the polynucleotide sequence, wherein said variant or fragment encodes a polypeptide having a biological activity which is functionally the same as the polypeptide (or fragment thereof) encoded by the polynucleotide of the invention, in particular the polynucleotide sequence defined in SEQ ID NO: 2 wherein said variant can be located and isolated using standard techniques in molecular biology, without undue trial and experimentation.

The degree of homology between two polynucleotide sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443-453) using, for instance, the default settings of GAP creation penalty of 5 and GAP width penalty of 0.3. Homologues of polynucleotide molecules are polynucleotide molecules that encode polypeptides having substantially the same functions and similar properties in different species, wherein the encoded polypeptides may share, within at least regions, at least 50% amino acid identity, and over the whole encoded amino acid sequences, at least about 30% amino acid identity, at least about 40% amino acid identity, at least about 50% amino acid identity, at least about 60% amino acid identity, at least about 70% amino acid identity, at least about 80% amino acid identity, at least about 90% amino acid identity or at least about 95% identity. Exemplary levels of sequence identity of the HOG1 polypeptide (SEQ ID NO: 1) with its homologues in rice (SEQ ID NO: 5), wheat (SEQ ID NO: 7), *chrysanthemum* (SEQ ID NO: 9) and *Petunia hybrida* (SEQ ID NO: 13) have been described above. The corresponding polynucleotide homologues may share significantly less than 50% identity due to degeneracy in the genetic code, and differences in preferred codon usage amongst different plant genera and species. For example, using CLUSTAL W (1.83), the polynucleotide encoding the HOG1 polypeptide (SEQ ID NO: 1) of the invention was shown to have 82% sequence identity with its homologue in rice (SEQ ID NO: 6), 83% sequence identity with its homologue in wheat (SEQ ID NO: 8), 82% sequence identity with its homologue in *chrysanthemum* (SEQ ID NO: 10), 78% sequence identity with its homologue in *Petunia hybrida* (SEQ ID NO: 14), 98% sequence identity with its homologue in *Brassica alboglabra* (SEQ ID NO: 12), 79% sequence identity with its homologue in *Lycopersicon esculentum* (SEQ ID NO: 28), 80% sequence identity with its homologue in *Solanum tuberosum* (SEQ ID NO: 30) and 78% sequence identity with the polynucleotide encoding the SAHH1 polypeptide of *Nicotiana tabacum* cv. *Xanthi* (SEQ ID NO: 4).

The polynucleotide molecule may also include within its scope a variant capable of hybridizing to the polynucleotide molecules of the invention, in particular the polynucleotide sequences defined in SEQ ID NOS: 4, 6, 8, 10, 12, 14, and 15 under conditions of low stringency, more preferably, medium stringency and still more preferably, high stringency. Low stringency hybridization conditions may correspond to hybridization performed at 50° C. in 2×SSC.

Suitable experimental conditions for determining whether a given polynucleotide molecule hybridizes to a specified polynucleotide may involve presoaking of a filter containing a relevant sample of the polynucleotide to be examined in 5×SSC for 10 min, and prehybridization of the filter in a solution of 5×SSC, 5×Denhardt's solution, 0.5% SDS and 100 μg/ml of denatured sonicated salmon sperm DNA, followed by hybridization in the same solution containing a concentration of 10 ng/ml of a $^{32}$P-dCTP-labeled probe for 12 hours at approximately 45° C., in accordance with the hybridization methods as described in Sambrook et al. (1989; Molecular Cloning, A Laboratory Manual, 2nd edition, Cold Spring Harbour, New York).

The filter is then washed twice for 30 minutes in 2×SSC, 0.5% SDS at least 55° C. (low stringency), at least 60° C. (medium stringency), at least 65° C. (medium/high stringency), at least 70° C. (high stringency), or at least 75° C. (very high stringency). Hybridization may be detected by exposure of the filter to an x-ray film.

Further, there are numerous conditions and factors, well known to those skilled in the art, which may be employed to alter the stringency of hybridization. For instance, the length and nature (DNA, RNA, base composition) of the polynucleotide to be hybridized to a specified polynucleotide; concentration of salts and other components, such as the presence or absence of formamide, dextran sulfate, polyethylene glycol etc; and altering the temperature of the hybridization and/or washing steps.

Further, it is also possible to theoretically predict whether or not two given polynucleotide sequences will hybridize under certain specified conditions.

Accordingly, as an alternative to the empirical method described above, the determination as to whether a variant polynucleotide sequence will hybridize to the polynucleotide molecule defined in accordance with the second or third aspect, or more specifically, the polynucleotide of SEQ ID NO: 2 or 15, can be based on a theoretical calculation of the $T_m$ (melting temperature) at which two heterologous polynucleotide sequences with known sequences will hybridize under specified conditions, such as salt concentration and temperature.

In determining the melting temperature for heterologous polynucleotide sequences ($T_{m(hetero)}$) it is necessary first to determine the melting temperature ($T_{m(homo)}$) for homologous polynucleotide sequences. The melting temperature ($T_{m(homo)}$) between two fully complementary polynucleotide strands (homoduplex formation) may be determined in accordance with the following formula, as outlined in Current Protocols in Molecular Biology, John Wiley and Sons, 1995, as:

$$T_{m(homo)}=81.5°\ C.+16.6(\log M)+0.41(\%\ GC)-0.61(\%\ form)-500/L$$

M=denotes the molarity of monovalent cations,
% GC=% guanine (G) and cytosine (C) of total number of bases in the sequence,
% form=% formamide in the hybridization buffer, and
L=the length of the polynucleotide sequence.

$T_m$ determined by the above formula is the $T_m$ of a homoduplex formation ($T_{m(homo)}$) between two fully complementary polynucleotide sequences. In order to adapt the $T_m$ value to that of two heterologous polynucleotide sequences, it is assumed that a 1% difference in nucleotide sequence between two heterologous sequences equals a 1° C. decrease in $T_m$. Therefore, the $T_{m(hetero)}$ for the heteroduplex formation is obtained through subtracting the homology % difference between the analogous sequence in question and the nucleotide probe described above from the $T_{m(homo)}$.

Typically the polynucleotide molecule defined in SEQ ID NO: 2 or 15 also includes within its scope a polynucleotide molecule which is an oligonucleotide fragment thereof. Typically, the oligonucleotide fragment is between about 15 to about 1775 nucleotides in length. More typically, the oligonucleotide fragment is between about 15 to about 1200 nucleotides in length. Even more typically, the oligonucleotide fragment is between about 15 to about 700 nucleotides in length. Even more typically still, the oligonucleotide fragment is between about 15 to about 200 nucleotides in length. Yet still more typically, the oligonucleotide fragment is between about 15 to about 75 nucleotides in length.

Typically, the oligonucleotide fragment is between about 15 to about 1775 nucleotides in length. More typically, the oligonucleotide fragment is between about 100 to about 1775 nucleotides in length. Even more typically, the oligonucleotide fragment is between about 500 to about 1775 nucleotides in length. Even more typically still, the oligonucleotide fragment is between about 1000 to about 1775 nucleotides in length. Yet still more typically, the oligonucleotide fragment is between about 1200 to about 1775 nucleotides in length.

The term "complementary" refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about to 100% of the nucleotides of the other strand. Alternatively, complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, and more preferably at least about 90% complementarity.

The polypeptide and polynucleotide molecules of the present invention are "isolated". The term "isolated" as used herein refers to substance that is substantially or essentially free from components that normally accompany it in its native state. For example, an "isolated polynucleotide", as used herein, refers to a polynucleotide, which has been purified from the sequences which flank it in a naturally occurring state. The "isolated" substance is either present in a preparation at a concentration higher than that substance found in nature or in its naturally occurring state or that the substance is present in a preparation that contains other materials with which the substance is not associated with in nature.

In certain embodiments, the polypeptide and polynucleotide molecules of the present invention are exogenous molecules. The term "exogenous" when used with reference to a polynucleotide or polypeptide molecule means that the polynucleotide or polypeptide is isolated and/or derived from a species other than the target cell species, into which the polynucleotide or polypeptide is to be introduced.

In one embodiment, a polynucleotide which decreases the expression of the polypeptide according to SEQ ID NO: 1 is introduced into the plant of interest. The polynucleotide may be an inhibitory polynucleotide, for example, an anti-sense polynucleotide (such as anti-sense RNA), an RNA interfering construct (such as siRNA) and a catalytic anti-sense nucleic acid construct (such as a ribozyme). The polynucleotides may be prepared using methods known to those skilled in the art, for example, by chemical synthesis, recombinant DNA procedures or, in the case of anti-sense RNA, by transcription in vitro or in vivo when linked to a promoter.

In certain embodiments, the polynucleotide is an anti-sense polynucleotide. An "antisense polynucleotide" is a polynucleotide sequence that is complementary to, and can therefore hybridize with, any one or all of the coding sequences of the present invention, including partial sequences thereof.

Full-length anti-sense molecules may be used for this purpose. Alternatively, double stranded oligonucleotides, sense and/or antisense oligonucleotides, or a combination thereof targeted to specific regions of the HOG1-encoded RNA may be utilized. The use of oligonucleotide molecules to decrease expression levels of a pre-determined gene is known in the art (see, for example, Hamilton, A. J. and Baulcombe, D. C. (1999), "A species of small antisense RNA in posttranscriptional gene silencing in plants", Science 286:950-952; Waterhouse P. M. et al (1998), "Virus resistance and gene silencing in plants can be induced by simultaneous expression of sense and antisense RNA", Proc. Natl. Acad. Sci. USA 95:13959-13964; and International patent publications WO 99/53050, WO 99/49029, WO 99/32619). Oligonucleotide molecules may be provided in situ by transforming plant cells with a DNA construct which, upon transcription, produces double stranded and/or anti-sense RNA sequences, which may be full-length or partial sequences. The gene silencing effect may be enhanced by over-producing both sense and/or anti-sense sequences (which may be full-length or partial) so that a high amount of double stranded RNA is produced.

As discussed above, sequences of anti-sense constructs may be derived from various regions of the HOG1 gene. For example, an anti-sense sequence may comprise at least 15, at least 20, or at least 25 contiguous nucleic acid residues from a polynucleotide which is complementary to a nucleic acid sequence which encodes a polypeptide which comprises an amino acid sequence with at least 70% sequence identity to the amino acid sequence according to SEQ ID NO: 1. The anti-sense sequence may comprise about 20, 25, 30, 35, 40, 50, 60, 70, 80, 90, 100, 200, 300, 400, 500, 600, 700, 800 or 850 contiguous nucleic acid residues. Any contiguous sequence comprising the desired number of residues may be used. The contiguous sequences can be designed using any method and algorithm known in the art. As an example, where anti-sense polynucleotides comprising 15 contiguous nucleic acid residues are desired, a first polynucleotide may comprise 15 contiguous nucleic acid residues beginning at position 301 of a polynucleotide sequence and ending at position 315 of the polynucleotide sequence, a second polynucleotide may comprise 15 contiguous nucleic acid residues beginning at position 302 of a polynucleotide sequence and ending at position 316 of the polynucleotide sequence, a third polynucleotide may comprise 15 contiguous nucleic acid residues beginning at position 303 of a polynucleotide sequence and ending at position 317 of the polynucleotide sequence, and a fourth polynucleotide may comprise 15 contiguous nucleic acid residues beginning at position 304 of a polynucleotide sequence and ending at position 318 of the polynucleotide sequence. Additional polynucleotides comprising 15 contiguous nucleic acid residues may be obtained by sequentially identifying stretches of 15 contiguous nucleic acid residues along the polynucleotide chain. It would be obvious to a person skilled in the art that contiguous sequences of other lengths may be prepared using a similar strategy.

In one embodiment, a first anti-sense polynucleotide comprising 15 contiguous nucleic acid residues beginning at position 271 and ending at position 286 of the polynucleotide sequence of SEQ ID NO: 2 has the following nucleic acid sequence: CTC GGC GCG GAA GTC (SEQ ID NO: 16). Using the strategy outlined above, a second anti-sense polynucleotide comprising 15 contiguous nucleic acid residues beginning at position 272 and ending at position 287 of the polynucleotide sequence of SEQ ID NO: 2 has the following nucleic acid sequence: TCG GCG CGG AAG TCA (SEQ ID NO: 17). Third and fourth anti-sense polynucleotides have the following nucleic acid sequences, respectively: CGG CGC GGA AGT CAG (SEQ ID NO: 18) and GGC GCG GAA GTC AGA (SEQ ID NO: 19). Additional anti-sense polynucleotides comprising 15 contiguous nucleic acid residues may be obtained as described above.

In certain embodiments, the anti-sense polynucleotide comprises 15 contiguous nucleic acid residues. In particular embodiments, the anti-sense polynucleotide comprises at least 100 contiguous nucleic acid residues.

Anti-sense constructs may be designed to target and bind to regulatory regions of the nucleotide sequence, such as the promoter, or to coding (exon) or non-coding (intron) sequences. In one embodiment, anti-sense polynucleotides targeted at SEQ ID NO: 2 are used, which results in decreased expression of the polypeptide according to SEQ ID NO: 1. In one embodiment, anti-sense polynucleotides according to SEQ ID NO: 15 (a 850 bp fragment of SEQ ID NO: 2 spanning the two SAHH signature domains) are used. Anti-sense constructs of the invention may be generated which are at least substantially complementary across their length to the region of the HOG1 gene in question (SEQ ID NO: 2). The binding of an anti-sense construct to its complementary cellular sequence may interfere with transcription, RNA processing, transport, translation and/or mRNA stability. Suitable anti-sense polynucleotides may be prepared by methods well known to those of skill in the art. Typically, anti-sense polynucleotides will be synthesized on automated synthesizers. Suitable anti-sense polynucleotides may include modifications designed to improve their delivery into cells, their stability once inside a cell, and/or their binding to the appropriate target. For example, the anti-sense polynucleotide may be modified by the addition of one or more phosphorothioate linkages, or the inclusion of one or morpholine rings into the backbone.

Alternatively, RNAi constructs may be used to decrease the expression of the polynucleotides encoding the polypeptide comprising SEQ ID NO: 1 according to known methods in the art (for example Fire et al. (1998) Nature 391: 806-811; Hammond, et al. (2001) Nature Rev, Genet. 2: 110-1119; Hammond et al. (2000) Nature 404: 293-296; Bernstein et al. (2001) Nature 409: 363-366; Elbashir et al (2001) Nature 411: 494-498; WO 99/49029 and WO 01/70949, the disclosures of which are incorporated herein by reference). RNAi refers to a means of selective post-transcriptional gene silencing by destruction of specific mRNA by small interfering RNA molecules (siRNA). The siRNA is typically generated by cleavage of double stranded RNA, where one strand is identical to the message to be inactivated. Double-stranded RNA molecules may be synthesised in which one strand is identical to a specific region of the mRNA transcript and introduced directly. Alternatively, corresponding double stranded DNA may be employed, which, once presented intracellularly is converted into double stranded RNA. Methods for the synthesis of suitable siRNA molecules for use in RNAi and for achieving post-transcriptional gene silencing are known to those of skill in the art. The skilled addressee will appreciate that a range of suitable siRNA constructs capable of decreasing the expression of the polynucleotide comprising SEQ ID NO: 2 can be identified and generated based on knowledge of the sequence of the gene in question using routine procedures known to those skilled in the art without undue experimentation.

Those skilled in the art will also appreciate that there need not necessarily be 100% nucleotide sequence match between the target sequence and the siRNA sequence. The capacity for mismatch is dependent largely on the location of the mismatch within the sequences. In some instances, mismatches of 2 or 3 nucleotides may be acceptable but in other instances a single nucleotide mismatch is enough to negate the effectiveness of the siRNA. The suitability of a particular siRNA molecule may be determined using routine procedures known to those skilled in the art without undue experimentation. For example, an RNA interference polynucleotide which comprises a nucleic acid sequence comprising at least 9 contiguous nucleic acid residues selected from a nucleic acid sequence which is complementary to a polynucleotide consisting of the nucleic acid sequence according to SEQ ID NO: 2 may be used. In some embodiments, RNA interference polynucleotides which comprise a nucleic acid sequence comprising about 9, 10, 11, or 12 contiguous nucleic acid residues may be used. Any contiguous sequence comprising the desired number of residues may be used. The contiguous sequences can be designed using any method and algorithm known in the art. As an example, where RNA interference polynucleotides comprising 9 contiguous nucleic acid residues are desired, a first polynucleotide may comprise 9 contiguous nucleic acid residues beginning at position 61 of a polynucleotide sequence and ending at position 69 of the polynucleotide sequence, a second polynucleotide may comprise 9 contiguous nucleic acid residues beginning at position 62 of a polynucleotide sequence and ending at position 70 of the polynucleotide sequence, a third polynucleotide may comprise 9 contiguous nucleic acid residues beginning at position 63 of a polynucleotide sequence and ending at position 71 of the polynucleotide sequence, and a fourth polynucleotide may comprise 9 contiguous nucleic acid residues beginning at position 64 of a polynucleotide sequence and ending at position 72 of the polynucleotide sequence. Additional polynucleotides comprising 9 contiguous nucleic acid residues may be obtained by sequentially identifying stretches of 9 contiguous nucleic acid residues along the polynucleotide chain. It would be obvious to a person skilled in the art that contiguous sequences of other lengths may be prepared using a similar strategy.

In one embodiment, a first RNA interference polynucleotide comprising 9 contiguous nucleic acid residues beginning at position 42 and ending at position 50 of the polynucleotide sequence of SEQ ID NO: 2 has the following sequence: AGA TCC GAA (SEQ ID NO: 20). Using the strategy outlined above, a second RNA interference polynucleotide comprising 9 contiguous nucleic acid residues beginning at position 43 and ending at position 51 of the polynucleotide sequence of SEQ ID NO: 2 has the following sequence: GAT CCG AAA (SEQ ID NO: 21). Third and fourth RNA interference polynucleotides have the following sequences, respectively: ATC CGA AAA (SEQ ID NO: 22) and TCC GAA AAA (SEQ ID NO: 23). Additional RNA interference polynucleotides comprising 9 contiguous nucleic acid residues may be obtained as described above. Further information about the design and use of siRNA can also be found in "The siRNA User Guide".

A further means of decreasing the expression of the polynucleotides encoding the polypeptide comprising SEQ ID NO: 1 may be achieved by introducing catalytic anti-sense nucleic acid constructs, such as ribozymes, which are capable of cleaving RNA transcripts and thereby preventing the production of wild-type protein. Ribozymes are targeted to and anneal with a particular sequence by virtue of two regions of sequence complementarity to the target flanking the ribozyme catalytic site. After binding, the ribozyme cleaves the target in a site-specific manner. The design and testing of ribozymes which specifically recognize and cleave sequences of interest can be achieved by techniques well known to those in the art (for example Lieber and Strauss, (1995) Mol. Cell. Biol. 15:540-551, the disclosure of which is incorporated herein by reference).

In certain embodiments, the decrease in the expression of the polynucleotide encoding the polypeptide comprising SEQ ID NO: 1 is the result of cosuppression. Cosuppression refers to inhibition of an endogenous gene caused by the introduction of a transgene. Typically, cosuppression is observed in transgenic plants that have been transformed with one or more copies of a gene construct that are identical to or share nucleotide sequence homology with an endogenous gene. In some of these transformed plants, suppression may occur for both the introduced transgene as well as the endogenous homologue, for example as a result of the fortuitous production of anti-sense RNA, or due to anomalous chromosomal interactions between the introduced transgene and the endogenous homologue (Hooper, *The petunia paradox: added copies of genes have puzzling effects in plants*, J. NIH Res. 3:49-54, (1991). Hence, instead of resulting in an increased level of expression of the introduced transgene, cosuppression leads to a decrease in the level of expression of the polypeptide according to SEQ ID NO: 1.

As described in Example 2, FIGS. 9*c*, 11*a*, 11*b*, 11*d*, and 11*g*, and Table 8 below, some of the transgenic rice plants transformed with over-expression constructs exhibited traits that were seen in plants transformed with anti-sense constructs as a result of cosuppression. For example, these cosuppression plants exhibited branching from the above-ground nodes of the major tillers (which led to a significant overall increase in the number of panicles per plant), and 2- to over 3-fold increases in the average number of seeds and plant biomass when compared to the WT.

Polynucleotides which introduce a mutation comprising single or multiple nucleotide insertions, deletions or substitutions to decrease the expression of the polypeptide according to SEQ ID NO: 1 are also contemplated. The single or multiple nucleotide insertions, deletions or substitutions may be introduced via recombination of the target mutation site with an introduced targeting nucleotide sequence. Such an introduced nucleotide sequence may, for example, comprise a nucleotide sequence to be introduced into the genome flanked either side by nucleotide sequences homologous to target sequences contiguous in or located either side of a desired mutation insertion point. The nucleotide sequences homologous to the target sequences may be isogenic with the target sequences to thereby promote the frequency of homologous recombination.

Homologous nucleotide sequences that are not strictly isogenic to the target sequences may also be used. Although mismatches between the homologous nucleotide sequences and the target sequences can adversely affect the frequency of homologous recombination, isogenicity is not strictly required and substantial homology may be sufficient. For the purposes of the present invention, the level of homology between the homologous sequences and the target sequences may be at least about 90% identity, at least about 95% identity, at least about 99% identity or 100% identity.

The mutations may be introduced by chemical or physical mutagenic techniques, or using insertional mutation means such as transposons or T-DNA, and exogenous nucleic acid may be introduced by recombinant means employing, for example, chemical assisted cell permeation (using, for example, calcium, lithium, PEG), electroporation, microinjection, liposome-mediated transfection, microparticle bombardment (biolistics), *Agrobacterium*-mediated transformation, virus infection, protoplast fusion or any other appropriate means as are known in the art.

The decrease or increase in the expression of the polynucleotides encoding the polypeptide according to SEQ ID NO: 1 may be stable or transient (for example, only in specific developmental stages or tissue in one or two generations), depending on whether the plant has been stably or transiently transformed. "Stably transformed" refers to the introduction and integration of one or more transgenes into the genome of a cell. Stable transformation of a cell may be detected by techniques that are known in the art, for example, by Southern blot hybridization of genomic DNA of the cell with nucleic acid sequences which are capable of binding to one or more of the transgenes, or by the polymerase chain reaction of genomic DNA of the cell to amplify transgene sequences.

In contrast, the term "transiently transformed" refers to the introduction of one or more transgenes into a cell where the transgene does not integrate into the genome of the transformed cell. Transient transformation may be detected, for example, by detecting the presence of a polypeptide encoded by one or more of the transgenes using enzyme-linked immunosorbent assay (ELISA) or by detecting the activity of the protein (e.g., β-glucuronidase) encoded by the transgene. Thus, a stable transformant is distinguished from a transient transformant in that, whereas genomic DNA from the stable transformant contains one or more transgenes, genomic DNA from the transient transformant does not contain a transgene.

The polynucleotides of the invention may be administered in the form of a naked DNA plasmid or in a vector. Naked DNA plasmids may be introduced into the host cells by methods known in the art, for example, transfection, electroporation, microinjection, transduction, cell fusion, DEAE dextran, calcium phosphate precipitation, use of a gene gun, or use of a DNA vector transporter.

In some preferred embodiments, the polynucleotides of the invention may be administered in a vector. The vector may be a plasmid vector, a viral vector, or any other suitable vehicle (such as cosmids) adapted for the insertion of foreign sequences and introduction into eukaryotic cells. In certain embodiments, the vector is an expression vector capable of directing the transcription of the DNA sequence of an inhibitory polynucleotide molecule of the invention into RNA. Viral expression vectors include, for example, epstein-barr virus-, bovine papilloma virus-, adenovirus- and adeno-associated virus-based vectors. In one embodiment, the vector is episomal. The use of a suitable episomal vector provides a means of maintaining the inhibitory nucleic acid molecule in target cells in high copy number extra-chromosomally thereby eliminating potential effects of chromosomal integration.

Vectors may also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. For example, operative linkage of a coding region to a promoter enables transcription of the coding region from the promoter by an RNA polymerase that specifically recognizes, binds to and transcribes the coding region. In certain embodiments, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Alternatively, inducible promoters such as stress-inducible promoters (e.g., high-light-, drought-, salinity- or temperature-induced promoters) may be used. Exemplary inducible promoters include the ribulose bisphosphate carboxylase (RuBisCo) small subunit gene promoters or chlorophyll a/b binding protein (CAB) gene promoters for expression in photosynthetic tissue, various seed storage protein gene promoters for expression in seeds, and root-specific glutamine synthetase gene promoters for expression in the root system of the transformed plant.

The vector may be a binary vector. For example, an *Agrobacterium* binary vector system may be used, which comprises the selected coding region under control of a constitutive or inducible promoter as described above, and linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate). Commonly used binary vectors include pBIN19, pPVP and pGreen.

In some embodiments, it may also be helpful to remove, add or alter 5' untranslated portions of the clones to eliminate extra, potentially inappropriate alternative translation initiation (i.e., start) codons or other sequences that may interfere with or reduce expression, either at the level of transcription or translation. Alternatively, consensus ribosome binding sites (see, e.g., Kozak, J Biol. Chem., 266:19867-19870 (1991)) can be inserted immediately 5' of the start codon to enhance expression. The desirability of (or need for) such modification may be empirically determined, and selection of these and other common vector elements are conventional. Many such sequences can also be derived from commercially available vectors. (See, for example, Sambrook, J. et al., Molecular Cloning, Cold Spring Harbor Laboratory (1989), Sambrook, J. and Russell, D. W. (2001), *"Molecular Cloning: A Laboratory Manual"*, 3rd edition, Cold Spring Harbor Laboratory Press, and references cited therein and Ausubel et al. (eds) Current Protocols in Molecular Biology, John Wiley & Sons (2000)).

A vector of the invention may be introduced into target cells using any suitable method known in the art for introducing DNA into cells, including but not limited to microinjection, electroporation, calcium phosphate precipitation, liposome-mediated delivery, viral infection, protoplast fusion, and particle-mediated uptake. Optionally, a polynucleotide of the invention is co-administered with a recombinase, for example recA, to a target cell to thereby enhance the rate of homologous recombination. The target cell(s) may already comprise, or have been transformed to comprise suitable recombinase target sequences, if required. For example, a recombinase protein(s) can be loaded onto a targeting DNA as described in U.S. Pat. No. 6,255,113. To enhance the loading process, a polynucleotide of the invention may contain one or more recombinogenic nucleation sequences, or be coated with a recombinase protein by pre-incubating the polynucleotide with a recombinase, whereby the recombinase is non-covalently bound to the polynucleotide (See, for example, A. Vergunst et al (1998), Nucleic Acids Res. 26:2729 and A. Vergunst and P. Hooykaas (1998), Plant Molec. Biol. 38:393 406, International patent publications WO 99/25821, WO 99/25840, WO 99/25855, and WO 99/25854 and U.S. Pat. Nos. 5,780,296, 6,255,113, and 6,686,515).

Transgenic plants with one of the polynucleotides of the invention can be generated using standard plant transformation methods known to those skilled in the art including, but not limited to, *Agrobacterium*-mediated transformation, cation or polyethylene glycol treatment of protoplasts, electroporation, microparticle bombardment, agitation of cell suspensions in solution with microbeads or microparticles coated with the transforming DNA, direct DNA uptake, liposome-mediated DNA uptake, and the like, as also described in a wide range of publicly available texts, such as: "Methods for Plant Molecular Biology" (Weissbach & Weissbach, eds., 1988); Clough, S. J. and Bent, A. F. (1998) "Floral dip: a simplified method for *Agrobacterium*-mediated transformation of *Arabidopsis thaliana*" Plant J. 16, 735-743; "Methods in Plant Molecular Biology" (Schuler & Zielinski, eds., 1989); "Plant Molecular Biology Manual" (Gelvin, Schilperoort, Verma, eds., 1993); and "Methods in Plant Molecular Biology-A Laboratory Manual" (Maliga, Klessig, Cashmore, Gruissem & Varner, eds., 1994). See also Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), these references being incorporated herein by cross-reference.

The preferred method of transformation may depend upon the plant to be transformed. *Agrobacterium* vectors are often used to transform dicotyledonous species. For transformation of monocotyledonous species, biolistic bombardment with particles coated with transforming DNA and silicon fibers coated with transforming DNA are often useful for nuclear transformation. However, *Agrobacterium*-mediated transformation of monocotyledonous species, including wheat, are now known (see, for example, International patent publications WO 97/48814; see also Hiei, Y. et al (1994), Plant J. 6(2):271-282 and international patent publication WO 92/06205).

Any plant cells may be transformed using the methods and materials of the present invention to produce genetically modified plants, plant cells, plant tissue, seed, and the like. Plant cells which have been transformed may be grown into plants in accordance with conventional methods as are known in the art (See, for example, McCormick, S. et al (1986), Plant Cell Reports 5:81-84)). The resulting plants may be self-pollinated, pollinated with the same transformed strain or different strains or hybridized, and the resulting plant(s) having the desired traits associated with SEQ ID NO: 1 or a homologue thereof identified. Two or more generations may be grown to ensure that this phenotypic characteristic is stably maintained. Alternatively, in vegetatively propagated crops, mature mutant/transgenic plants may be propagated by cutting or by tissue culture techniques to produce identical plants. Selection of mutant/transgenic plants can be carried out and new varieties may be obtained and propagated vegetatively for commercial use.

Plant parts, including but not limited to roots, stems, leaves, buds, flowers, shoots, seeds, tubers, fruits and branches obtained from plants obtained by the methods of the present invention are also provided.

Plants or plant parts transformed by the methods of the invention may be visually identified based on the expression of the traits. More preferably, the transformed plants or plant parts are identified using molecular analysis using specific oligonucleotide probes and/or amplification of the target gene. DNA or RNA from the subject plant or plant part to be analyzed may be extracted by a number of suitable methods known to those skilled in the art, such as are described in a wide range of well known texts, including (but not limited to) Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), incorporated herein by cross-reference. See also the methods described in Lukowitz, W., Gillmor, C. S. and Scheble, W-R. (2000) "Positional Cloning in *Arabidopsis*: Why It Feels Good to Have a Genome Initiative Working for You" Plant Physiology 123, 795-805, and references cited therein.

The extracted DNA or RNA may be analyzed for the presence or absence of the transgene by any suitable method as known in the art, and which method/strategy is employed may depend on the specificity desired, and the availability of suitable sequences and/or enzymes. For example, extracted RNA may be analyzed using the TRIzol method, and treating the extracted RNA with RNase-free DNaseI before performing quantitative PCR.

Suitable primer pairs for amplifying portions of HOG1 include: PET1: 5'-A(AG) ATGCC(CT) GG(ACT) CT (ACT) ATG(GT)C(ACT)T-3' (SEQ ID NO: 24) and PET2: 5'-TC (AG) AACTTGCTCTTGGT(AG)AC(AG)-3' (SEQ ID NO: 25). Other suitable primers or primer pairs for analyzing the HOG1 gene or homologues thereof may be designed based on SEQ ID NO: 1.

The methods and reagents for use in a PCR amplification reaction are well known to those skilled in the art. Suitable protocols and reagents will largely depend on individual circumstances. Guidance may be obtained from a variety of sources, such as for example Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), incorporated herein by cross-reference. A person skilled in the art would also readily appreciate that various parameters of the PCR reaction may be altered without affecting the ability to amplify the desired product. For example the $Mg^{2+}$ concentration and temperatures employed may be varied. Similarly, the amount of genomic DNA used as a template may also be varied depending on the amount of DNA available.

Other methods of analysis include electrophoresis, such as agarose or polyacrylamide gel electrophoresis, a technique commonly used by those skilled in the art for separation of DNA fragments on the basis of size. The concentration of agarose or polyacrylamide in the gel in large part determines the resolution ability of the gel and the appropriate concentration of agarose or polyacrylamide will therefore depend on the size of the DNA fragments to be distinguished.

Detection and/or determination of the existence of the transgene or homologue thereof may be aided by computer analysis using any appropriate software. Suitable software packages for comparison of determined nucleotide sequences are well known in the art and are readily available.

ABBREVIATIONS

2iP—2-isopentenyladenine
AHK—*Arabidopsis* Histidine Kinase

AHP—Arabidosis Histidine Phosphotransfer proteins
AMM—asparagine minimal medium
ARR—*Arabidopsis* Response Regulators
AS—Anti-sense suppression
A—Adenosine
BA—Benzyladenine
BLAST—Basic Local Alignment Search Tool
CAB—chlorophyll a/b binding protein gene
CaMV—Cauliflower Mosaic Virus
CRE—cytokinin-response
cDNA—complementary deoxyribonucleic acid
DNA—deoxyribonucleic acid
ELISA—enzyme linked immunosorbent assay
ETR1, ERS2, ETR2 and EIN4—ethylene receptors
FAB—fast atom bombardment
G—Guanine
GFP—green fluorescent protein
HOG 1—Homology-dependent gene silencing 1
HSPs—high scoring sequence pair
ITC—Isothermal titration calorimetry
KD—dissociation constant
KNAT1—Knotted homolog of *Arabidopsis thaliana* 1
LAI—leaf area index
LAR—leaf area ratio
mRNA—messenger RNA
NCBI—National Center for Biotechnology Information
NOS—nopaline synthase
OCS—octopine synthase
OE—Overexpression
OsCBP—*Oryza sativa* Cytokinin Binding Protein
PCR—Polymerase chain reaction
PNAs—peptide nucleic acids
PETCBP—*Petunia hybrida* Cytokinin Binding Protein
RNA—ribonucleic acid
RNAi—RNA interference
RuBisCo—ribulose bisphosphate carboxylase
SAH—S-adenosylhomocysteine
SAM—S-adenosylmethionine
siRNA—small interfering RNA
SSC—1-2 X sodium chloride and sodium citrate
SAHH—S-adenosyl-L-homocysteine hydrolase
SLA—specific leaf area
STM—Shoot Meristemless transcription factor
T—thymine
TDNA—transferred DNA
Tm—thermal melting point
U—Uracil
WT—wild type
ZR—zeatin riboside

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

Endogenous cytokinins were quantified by the method of immunoassay with monoclonal antibody iPA and ZR using isopentenyl adenosine and zeatin riboside detection kits (Sigma). Values given represent the mean±SD of three replicates from three independent extractions. The cytokinins measured are isopentenyladenine (iP), isopentenyladenosine (iPA), zeatin (Z) and zeatin riboside (ZR). H) Spectrophotometric assay of S-adenosyl homocysteine hydrolase (SAHH) activity from the various lines and with the purified TAP-HOG1 protein. No significant differences in activity were observed in the crude protein extracts from the WT, OE and AS lines, while purified TAP-HOG1 protein lacks measurable SAHH activity.

Figure 4:
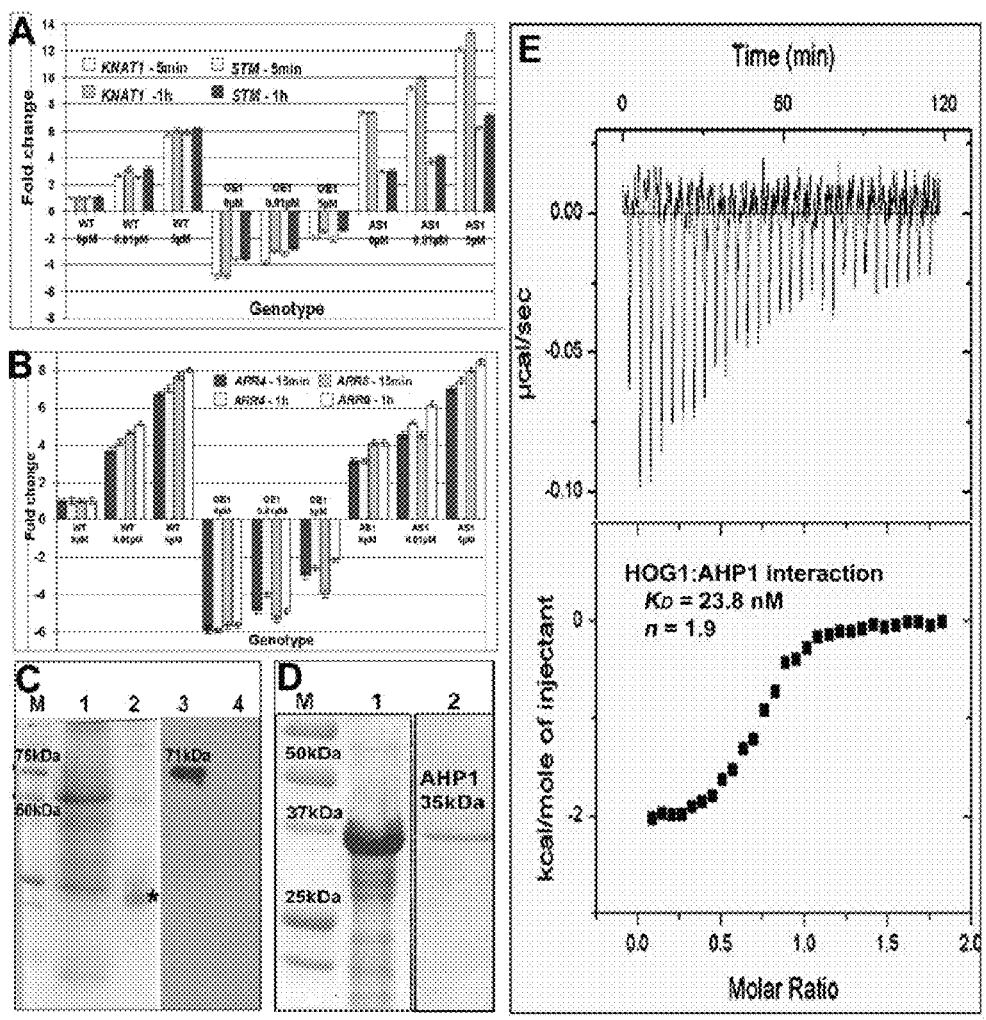

FIG. 4 shows the quantitative real-time PCR analysis of selected cytokinin responsive genes and HOG1-AHP1 interaction. Seedlings were harvested for RNA extraction before and after a pulse treatment with benzyladenine (BA) at 0 µM, 0.01 µM, 0.1 µM, 1 µM or 5 µM over several time intervals (5 min, 15 min, 30 min and 1 h) from three independent anti-sense suppression (AS1, AS8, AS21) and over-expression (OE1, OE12, OE18) lines. Application of BA caused a dose-dependent increase of KNAT1 and STM transcripts. A) The AS lines showed up-regulation of KNAT1 and STM (homeobox genes involved in meristem function), while OE lines showed down-regulation of these two genes in the absence of exogenous BA. With 5 µM BA after 1 h the expression of KNAT1 and STM showed less than a two fold change, which is insignificant from that of the WT. B) ARR4 and ARR6 (type-A response regulators induced by cytokinins) also show similar trend in the expression levels. C) Purification of TAP-HOG1 complex. Total protein extracted from 35S:TAP-HOG1 plants (lane 1) and after purification using affinity columns for ProtA and CBP tags resulted in the identification of an approximately 24 kDa band (asterisk) that was confirmed to be AHP1 by N-terminal sequencing (lane 2). Western blot of total protein probed with antibody for ProtA tag showed the presence of a 71 kDa band corresponding to TAP-HOG1. D) SDS-polyacrylamide gel electrophoresis of recombinant AHP1 purification. AHP1 was expressed with six-His and thioredoxin-tags in *E. coli*. Lane 1 has total cell lysate and purified AHP1 with the tags is in lane 2. E) TAP-HOG1 and AHP1 interaction was performed with ITC. The top panel of E) shows raw heat data corrected to baseline drift obtained from injections of 0.1 µM purified AHP1 into the sample cell containing 2 µM purified TAP-HOG1. The bottom panel shows the binding isotherm created by plotting the heat peak areas against the molar ratio of AHP1 added to HOG1. The TAP-HOG1 and AHP1 binding is endothermic with a KD value of 23.8 nM.

Figure 5:
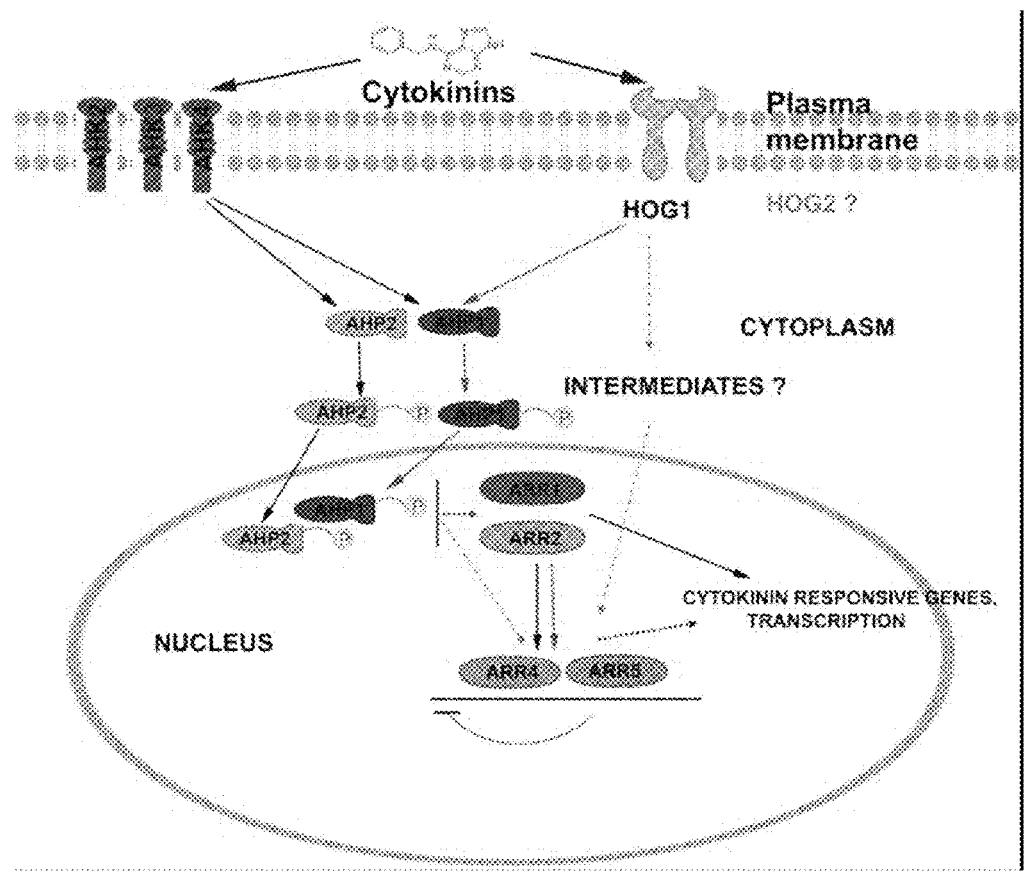

FIG. 5 is a schematic representation of the cytokinin signal transduction pathway via HOG1. Cytokinin signal is perceived by HOG1 at the plasma membrane. The HOG1 dimer initiates a signaling cascade through AHP1, which may interact with type-B ARRs (e.g. ARR1, ARR2) and type-A ARRs (e.g. ARR4, ARR5).

FIGS. 6A and 6B show the multiple sequence alignment of HOG1 with homologs. The deduced amino acid sequence of HOG1 (SEQ ID NO: 1) was aligned with SAHH sequence from *Petunia hybrida* (SEQ ID NO: 13), *Nicotiana tabacum* (SEQ ID NO: 3), *Oryza sativa* (SEQ ID NO: 5), *Triticum aestivum* (SEQ ID NO: 7), and *Homo sapiens* (SEQ ID NO: 26). The two conserved signatures of SAHH are in bold. In the $2^{nd}$ signature of SAHH, three conserved glycine residues representing the dinucleotide binding domain are underlined. The N-terminal stretch of 7 (position 1-7 of HOG1) amino acids and an additional stretch of 41 amino acids (position 150-191 of HOG1) as well as the helical transmembrane region in italics (position 59-76 of HOG1).

Figure 2:
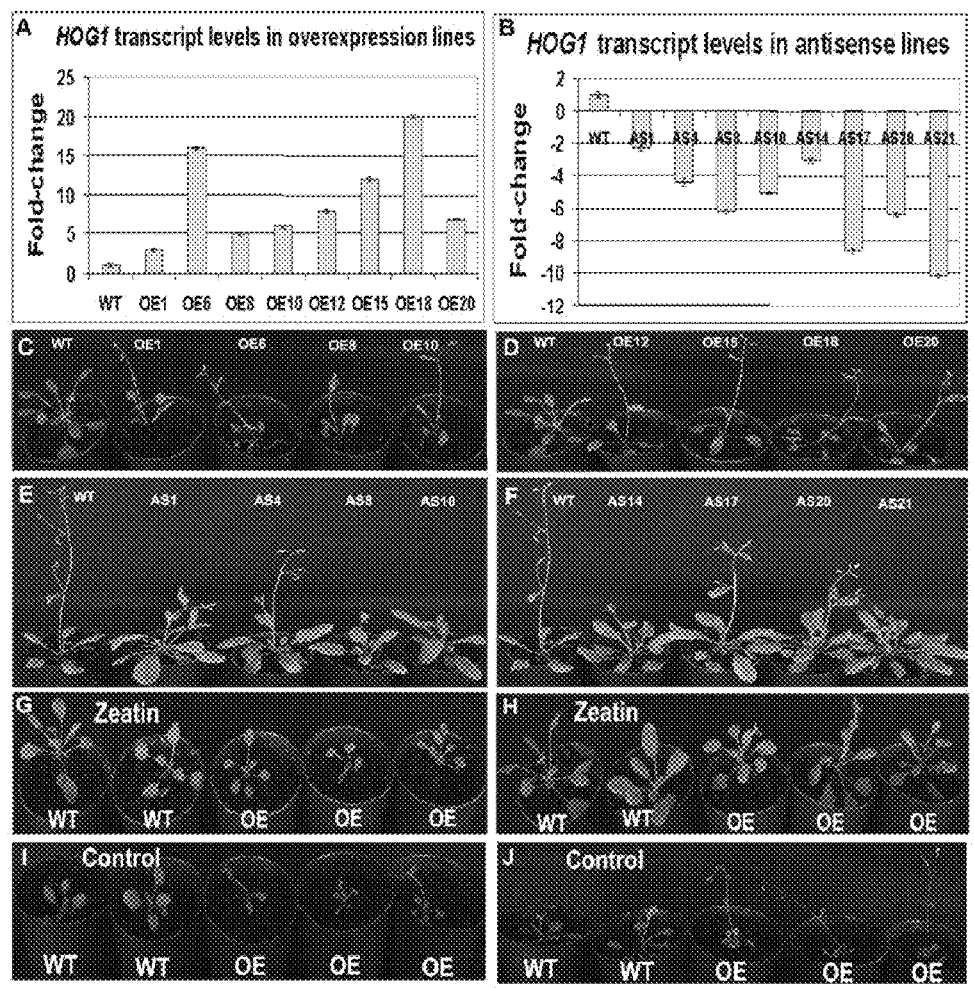
FIG. 2 shows the expression analysis of HOG1 in the over-expression and anti-sense suppression lines of *Arabidopsis* by quantitative real time PCR. A) Eight independent over-expression lines showed 3- to 20-fold increase in HOG1 transcript levels compared to the wild type. B) and C) Phenotypes of the over-expression lines used for real time PCR analysis were uniform despite the variations in transcript levels. D) HOG1 anti-sense suppression lines showed 2- to 10-fold decrease in the expression levels of the transcripts when compared to the wild type. E) and F) The flowering time phenotypes of the eight anti-sense lines used in the expression analysis were directly related to the level of suppression of HOG1 transcripts. G), H), I) and J) Three individual seedlings of OE line 6 and two WT plants were sprayed on alternate days with zeatin (0.01 µM) over a period of four weeks to see if the exogenously applied cytokinin can delay flowering in the OE lines to the same age as the WT. G) OE plants sprayed with zeatin showed delayed bolting compared to the control OE lines (no zeatin), while, I) the control OE lines bolt at 4 rosette leaf stage. H) OE plants sprayed with zeatin show bolting only after they have reached the 6 to 7 leaf stage, almost at the same age as the WT plants, showing rescue of the OE lines by the exogenously applied cytokinin. J) The control individuals (without zeatin spray) of the OE line have fully flowered and grown to their maximum capacity at this stage.
Figure 7:
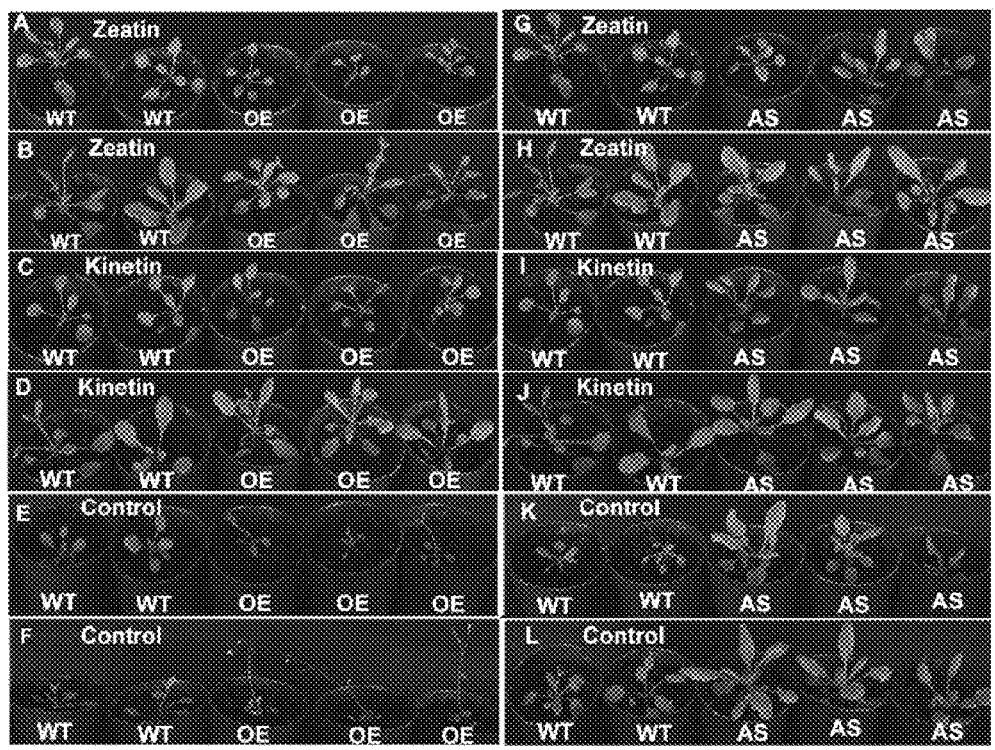

FIG. 7 shows the effect of exogenous application of cytokinins on wild type (WT), over-expression (OE) and anti-sense suppression (AS) lines of HOG1. Three individual seedlings of OE line 6 and AS line 12 were sprayed on alternate days with zeatin or kinetin (0.01 µM), over a period of four weeks. Two WT plants were similarly treated for comparison. A) and C) Three individuals of OE line 6 sprayed with zeatin and kinetin did not show any bolting when compared to the control OE lines at the 4 leaf stage of growth. E) The control OE lines bolt at 4 leaf stage. B) and D) Three individuals of OE line 6 sprayed with zeatin and kinetin respectively, show bolting only after they have reached the 6-7 leaf stage. This shows partial rescue of the OE lines by the exogenously applied cytokinins. F) The control individuals of the OE line 6 have matured at this stage. G), H), I), J), K) and L) The AS lines that received the cytokinin sprays did not show any significant difference in phenotype when compared with the control AS lines. This shows that over-expressing HOG1 leads to depletion of endogenous cytokinin content (as shown in Table 1) and hence, the phenotype. (Note that panels A, B, E and F are in the main FIG. 2 as panels G, H, I and J, and these are included here for ease of comparison only).

Figure 8:
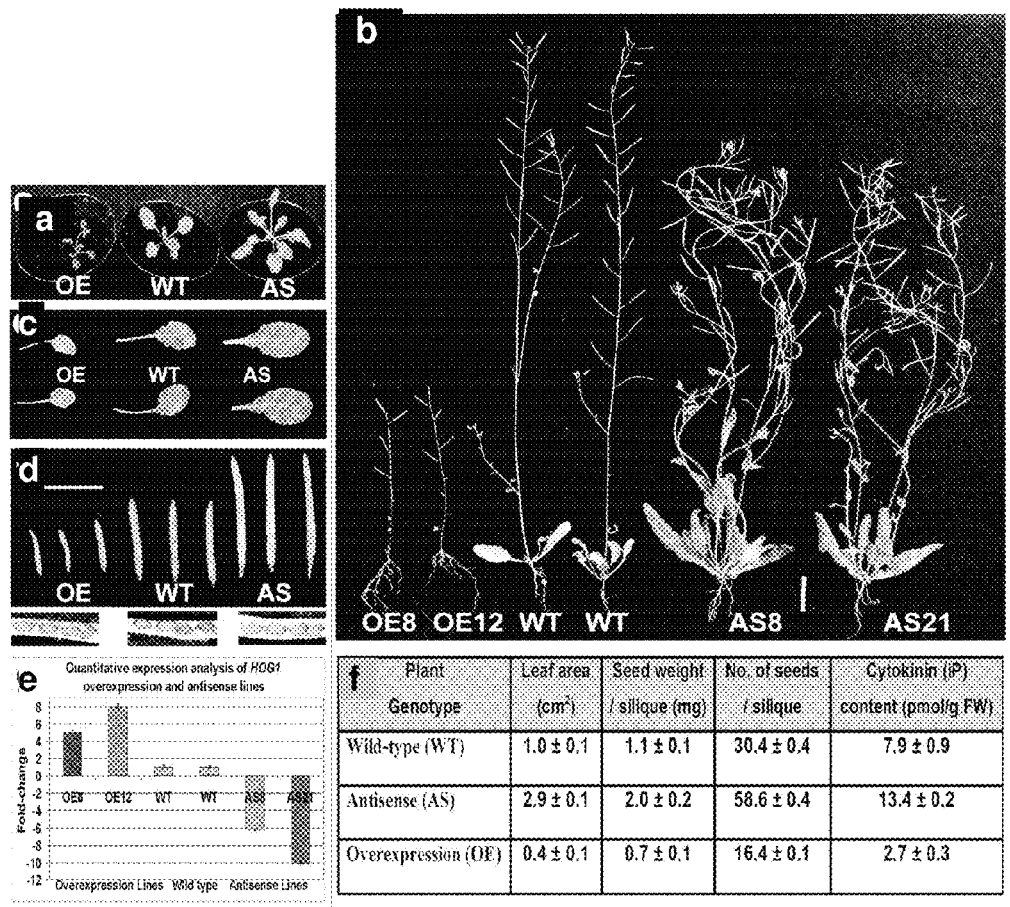

FIG. 8 shows transgenic *Arabidopsis* plants. (a) Seedlings of *Arabidopsis thaliana* with over-expression (OE) of HOG1 showed early bolting, but anti-sense suppression (AS) of HOG1 leads to delayed flowering compared to the wild type (WT) control at about 3 weeks. (b) Mature plants of two independent transgenic lines each of OE (OE8, OE12) and AS (AS8, AS21) compared to the wild type (WT) photographed at 30 days after germination. The inflorescences of AS lines were profusely branched and the biomass was significantly higher compared to the OE and WT plants. (c) The leaf area and (d) silique length as well as seeds (inset in panel f) of the AS lines were significantly higher than that of OE and WT. (e) Real-time quantitative PCR analysis of expression levels of HOG1 transcripts in the plants in (d). (f) Quantification of the leaf area, seed weight, number of seeds per silique and endogenous concentration of the cytokinin isopentenyl adenine showed that the values were the highest in AS followed by the WT and OE lines, respectively.

Figure 9:
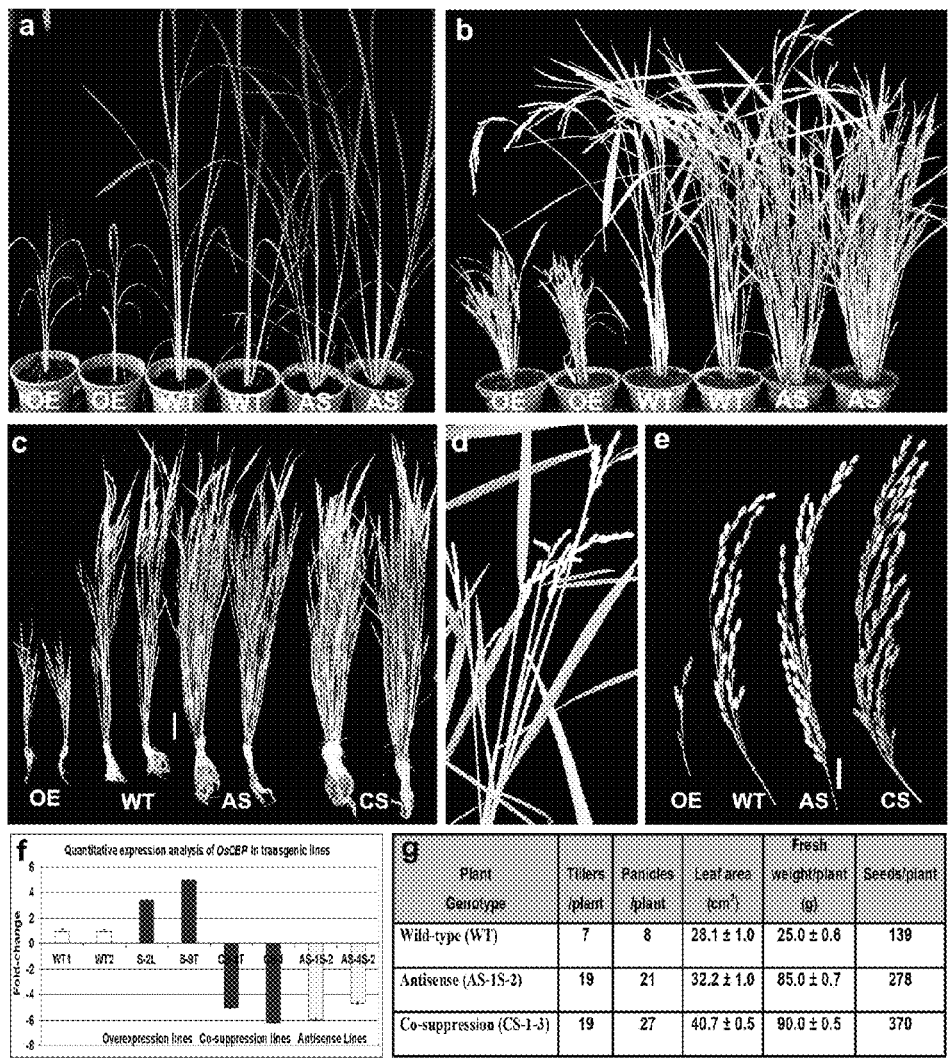

FIG. 9 shows transgenic rice (*Oryza sativa* ssp. *japonica* cv Nipponbare) plants harboring the *Arabidopsis* HOG1 cDNA in over-expression (OE) or anti-sense suppression (AS) leading to modified OsCBP levels. (a) Seedlings of OE and AS lines at the time of tiller initiation about four weeks after germination. (b) Mature plants of the OE and AS lines at about 90 days after germination. The AS lines exhibit profuse tillering and increase in biomass, while the OE plants remained dwarf compared to the WT. (c) The uprooted mature plants of OE, WT, AS and cosuppression (CS) showed that AS and CS plants had comparably higher tiller numbers per plant. (d) The CS plants showed branching from the above-ground nodes resulting in an overall increase in number of panicles per plant. (e) The panicles of OE lines were significantly smaller compared to that of the other lines. (f) Real-time quantitative PCR analysis of expression levels of OsCBP transcripts in the WT, introduced *Arabidopsis* HOG1 transcript levels in the OE lines (S-2L, S-9T), reduction in the endogenous OsCBP transcript levels in CS (CS-4T, CS-1) and AS (AS-1S-2, AS-4S-2) lines. (g) Quantification of the number of tillers, panicles, leaf area, fresh weight and total number of seeds per plant showed that the measured parameters were significantly higher in the AS and CS lines compared to the WT, which is consistent with the observations from *Arabidopsis*.

FIG. 10 shows: (a) multiple alignment of HOG1 (SEQ ID NO: 1), PETCBP (SEQ ID NO: 13) and OsCBP (SEQ ID NO: 5). PETCBP (SEQ ID NO: 13) and OsCBP (SEQ ID NO: 5) showed 88% identities. HOG1 (SEQ ID NO: 1) and OsCBP (SEQ ID NO: 5) showed 90% identity when compared to 88% identity for PETCBP (SEQ ID NO: 13) and HOG1 (SEQ ID NO: 1). (b) OsCBP genome blast shows its presence on chromosome 11 (Os11g0455500), indicating that it is a single copy in the rice genome.

Figure 11:
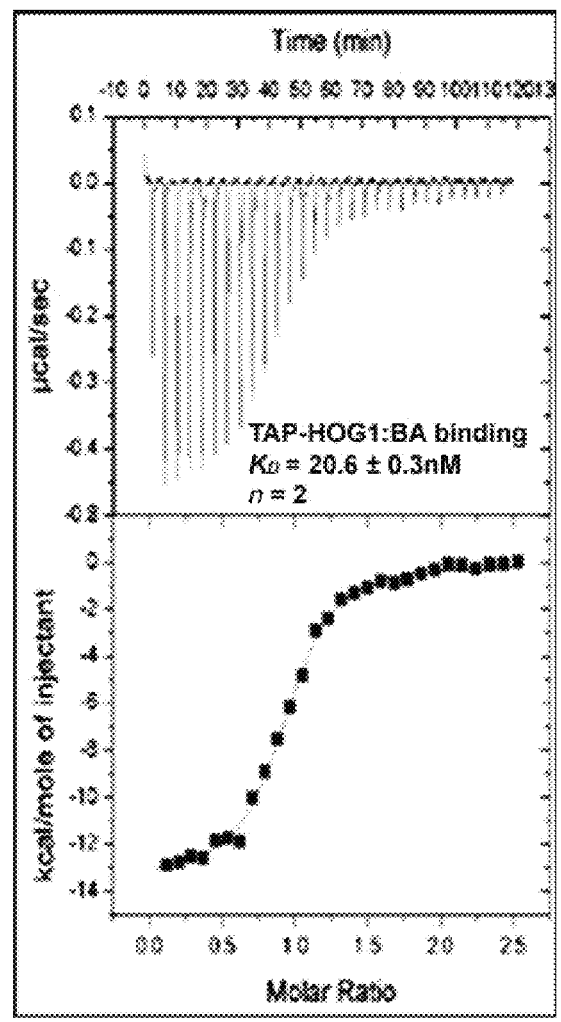

FIG. 11 shows the results of cytokinin binding assay performed with ITC. The top panel shows raw heat data corrected to baseline drift obtained from injections of 0.1 µM benzyladenine into the sample cell containing 2 µM purified TAP-HOG1. The bottom panel shows the binding isotherm created by plotting the heat peak areas against the molar ratio of benzyladenine added to HOG1.

Figure 12:
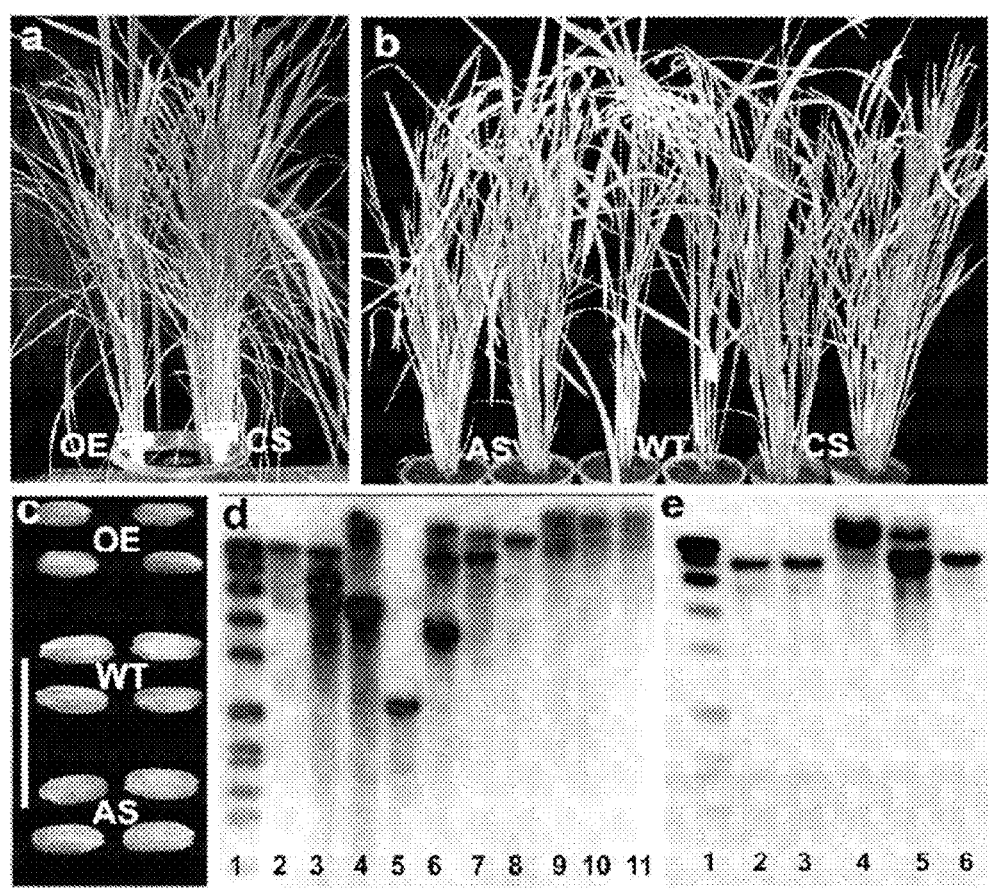

FIG. 12 shows the phenotypes of transgenic rice (*Oryza sativa* ssp. *japonica* cv *Nipponbare*) plants with over-expression (OE) of *Arabidopsis* HOG1 or anti-sense suppression (AS) of OsCBP induced by *Arabidopsis* HOG1. (a) OE line with co-suppression effect (on the right of panel, with the control on the left) shows increased number of tillers per plant. (b) AS, wild type (WT) and cosuppression (CS) lines at maturity. AS and CS lines exhibit more number of tillers (branching) per plant compared to the hybrid parent line (WT). (c) No significant difference in the seed size of WT and AS lines. Some reduction in seed size is observed in OE when compared to WT. (d) and (e) Southern blots of OE and AS lines at T1 generation. (d) 1st lane is the marker. Lanes 2 to 11 are independent OE lines. Lane 2 (OE line S1), lane 5 (OE line 4) and lane 8 (OE line 7) show single insertions. Lane 4 (OE line 3), lane 7 (OE line 6), Lane 9 (OE line 9), Lane 10 (OE line 10) and lane 11 (OE line 11) show double insertions whereas lane 3 (OE line 2) and lane 6 (OE line 5) show three insertions each. (e) Lane 2 (line AS1), lane 3 (line AS2), lane 4 (line AS3) and lane 6 (line AS5) show single insertions. Lane 5 (line AS4) shows double insertion. For each lane, genomic DNA (6 µg) extracted from leaves was digested with EcoRI enzyme was used. The probe used was DIG labeled, hygromycin phosphotransferase gene. Blots were washed at high stringency before signals were visualized.

BEST MODE

Non-limiting examples of the invention, including the best mode, and a comparative example will be further described in greater detail by reference to specific Examples, which should not be construed as in any way limiting the scope of the invention.

Example 1

The *Arabidopsis* Homology Dependent Gene Silencing1 (Hog1) is a Putative Cytokinin Receptor Materials and Methods
Plant Materials and Growth Conditions

*Arabidopsis thaliana* ecotype Columbia was used in this study. Plants were grown with 16 h light/8 h dark at 22° C. For seedling assays, seeds were surface-sterilized and stratified in the dark at 4° C. for 2 days and then exposed to white light (75 $\mu E \cdot m^{-2} \cdot s^{-1}$). Seedlings were grown at 22° C. on Murashige-Skoog (MS) medium with 3% sucrose and 0.9% agar. For germination experiment, seeds of specific batches were sown on MS medium without sucrose.

Plasmid Construction and Genetic Transformation of *Arabidopsis*

Full length *Arabidopsis thaliana* HOG1 cDNA (SEQ ID NO: 2) was amplified by 5' and 3' RACE strategy. The SMART™ RACE cDNA Amplification Kit (Clontech Laboratories) was used to identify the 5'- and 3'-cDNA (5'/3'-RACE) end sequences of cDNA. These PCR products were sequenced. The partial sequence and RACE PCR products were aligned together to obtain the full length cDNA sequence for *Arabidopsis thaliana* HOG1 (SEQ ID NO: 2).

pGreen 0229 binary vector (Yu et al. *Proc. Natl. Acad. Sci. USA* 101:7827-7832, 2004) was used for all the transgene constructs. For anti-sense suppression, an 850 bp fragment of HOG1 spanning the two SAHH signatures (SEQ ID NO: 15) was used. The complete open reading frame of HOG1 cDNA was used for the over-expression construct and for the GFP-HOG1 construct.

TAP-tagged HOG1 was prepared with Prot A and calmodulin binding peptide tags, with a TEV cleavage site between the two tags (Forler et al. *Nature* 21:89-92, 2003). The constructs were introduced into *Arabidopsis thaliana* by *Agrobacterium tumefaciens*-mediated vacuum infiltration method (Hiei et al. supra).

Real-Time PCR Analysis

Total RNA was extracted from seedlings with the TRIzol method (Invitrogen). Total RNA (0.5 µg) treated with RNase-free DNaseI was used for each quantitative PCR reaction performed with the One-Step RT kit (Qiagen) according to the manufacturer's instructions. Quantitative real-time PCR was performed using SYBR green. The Ct values were normalized against the Tubulin2 Ct value for calculation of fold-change according to the manufacturer's protocol.

Isothermal Titration Calorimetry (ITC)

Cytokinin binding affinity and thermodynamic analysis of the interaction between HOG1 and cytokinins was examined by ITC (MCSITC, Microcal, Northampton, USA). Three naturally occurring cytokinins (zeatin, benzyladenine and isopentenyl adenine) and thidiazuron (an urea-derived synthetic cytokinin) were used. Additionally, adenosine and NAD were used as control molecules to verify the binding specificity of HOG1 to cytokinins. Data were analyzed by MICROCAL ORIGIN version 2.9 using the best-fit, nonlinear least-squares method for one binding site. The binding stoichiometry (n), and association constant (KA) were calculated from the fitted curves. Subsequently, KD was calculated as 1/KA. Raw heat data were corrected to baseline drift obtained from injections of 0.1 µM purified AHP1 into the sample cell containing 2 µM purified TAP-HOG1. Binding isotherms were created by plotting the heat peak areas against the molar ratio of AHP1 added to HOG1.

Subcellular Localization of GFP-HOG1 Fusion Protein

Transgenic plants expressing individual 35S:GFP-HOG1 fusion constructs were selected according to their phenotype. Roots from 5-day seedlings were cut and mounted in half strength MS medium immediately before confocal laser scanning microscopy (Zeiss CLSM 510) with a 488 nm argon laser in combination with 505- to 530-nm bandpass filter set.

Cytokinin Response Assay of Callus

Seedling root segments were incubated for 4 days on callus induction medium (MS medium supplemented with 0.5 µg/ml 2,4-dichlorophenoxyacetic acid and 0.05 µg/ml kinetin). The resultant calluses were incubated on shoot induction medium (MS medium supplemented with 0.2 µg/ml indole-butyric acid and various concentrations of zeatin) for 30 days with subculturing to fresh medium at 10 day intervals according to the method of Inoue et al. (*Nature* 409:1060-1063, 2001).

Cytokinin Content and SAHH Enzyme Assay

Cytokinins were extracted from whole plants with 100% methanol and quantified using isopentenyl adenosine and zeatin riboside detection kits (Sigma) as described in Yang et al. (*FEBS* 555:291-296, 2003). The SAHH spectrophotometric assay was performed on crude protein extracts of bolting plants as described in Rocha et al. (*Plant Cell* 17:404-417, 2005).

Expression of Cytokinin Primary-Response Genes

For quantitative real-time PCR (qRT-PCR) analysis of cytokinin-inducible gene expression, seeds were germinated on MS medium with 3% (w/v) sucrose and grown for 6 days. Cytokinin treatment was carried out by incubating seedlings in the same MS+sucrose liquid medium (no agar) supplemented with 0, 0.01, 0.1, 1 or 5 µM [solubilized in 0.1% dimethylsulfoxide (DMSO) and diluted with the MS medium] for 5 min, 15 min, 30 min or 1 h. The control seedlings were incubated with DMSO (0.1%, the concentration used to dissolve cytokinins for the treatment) for the corresponding durations and used for expression analysis. Before RNA preparation, WT, OE and AS seedlings were pooled and stored in RNAlater solution (Qiagen, Valencia, Calif.). Total RNA was extracted using the Rneasy Plant Mini Kit (Qiagen). SYBRgreen RT-PCR reagents (Applied Biosystems) were used to synthesize double-stranded cDNA. The number of transcripts present in biological replicates each of WT, OE and AS seedlings, with or without BA and DMSO, was determined from three independent replicates. Fold induction of the transcripts was calculated according to the manufacturer's instructions (ABI Prism 7700 Sequence Detection System, User Bulletin #2).

TAP-HOG1 and AHP1 Interaction Studies

TAP-HOG1 protein complex was purified using the ProtA and CBP tags as described before in Forler et al. (supra). For ProtA pulldown, IgG Sepharose beads (Amersham Biosciences #17-0969-01) and for CBP pulldown Calmodulin affinity resin (Stratagene #214303-52) were used. The purified protein was subjected to SDS-PAGE and blotted to PVDF membranes for Western blot analysis using standard protocols. Furthermore, the HOG1-complex pulled down was subjected to SDS-PAGE electrophoresis, and N-terminal sequencing was done to identify the prominent bands obtained. Because AHP1 was the major putative interacting protein band, the cDNA for AHP1 was cloned from *Arabidopsis* and recombinant AHP1 was expressed in *E. coli* BL21 with a six-HIS tag and thioredoxin tag (in the expression vector PET32EK/LIC, Novagen). The recombinant AHP1 with the tags was purified using HIS-tag affinity column (BioRad). Protein interaction (HOG1-AHP1) studies were carried out by ITC (MCS-ITC, Microcal, Northampton, USA) as outlined above.

Results and Discussion

The present inventors used anti-sense suppression and over-expression strategies to analyze the involvement of HOG1 in cytokinin signaling and regulation of plant development.

The cDNA clone of HOG1 (SEQ ID NO: 2) exhibited significant sequence similarity to S-adenosyl-L-homocysteine hydrolase (SAHH) from several species of plants and animals. Comparison with isolated homologues from several plant species indicated that HOG1 is conserved in diverse plant species (FIG. 6). In particular, the homologue in *Petunia hybrida* (SEQ ID NO: 14) shared 78% sequence similarity with HOG1, the homologue in *Nicotiana tabacum* (SEQ ID NO: 4) shared 78% sequence similarity with HOG1, the homologue in *Oryza sativa* (SEQ ID NO: 6) shared 82% sequence similarity with HOG1, and the homologue in *Triticum aestivum* (SEQ ID NO: 4) shared 83% sequence similarity with HOG1.

To examine the cytokinin binding affinity of HOG1, TAP-HOG1 protein was purified from transgenic *Arabidopsis thaliana* (harboring 35S:TAP-HOG1), which was also used for protein-protein interaction studies. The tagged protein was functional because the transgenic plants showed the same phenotype as that of the HOG1 over-expression lines. The protein was purified using Protein A (Prot-A) and CBP (calmodulin binding peptide) tags. After purification, the protein retained the CBP portion of the TAP tag, resulting in a size of 60 kDa (FIG. 1A inset), whereas HOG1 alone without the CBP portion of the TAP tag should be 56 kDa.

(a) HOG1 Binds to Cytokinins with High Affinity

Cytokinin molecules bind to the purified protein efficiently as indicated by isothermal titration calorimetry (ITC) of purified TAP-HOG1 and various cytokinins. ITC, a biophysical technique used to study ligand-receptor binding kinetics yields important thermodynamic parameters of an interaction, including binding affinity (KA), and hence the dissociation constant (KD), as well as the binding stoichiometry (n).

Cytokinin molecules (zeatin, benzyladenine and isopentenyl adenine) and thidiazuron (a synthetic urea-derived molecule with cytokinin activity) were used for the binding studies. Adenine and NAD were used as controls to determine the binding specificity of HOG1.

Figure 1:
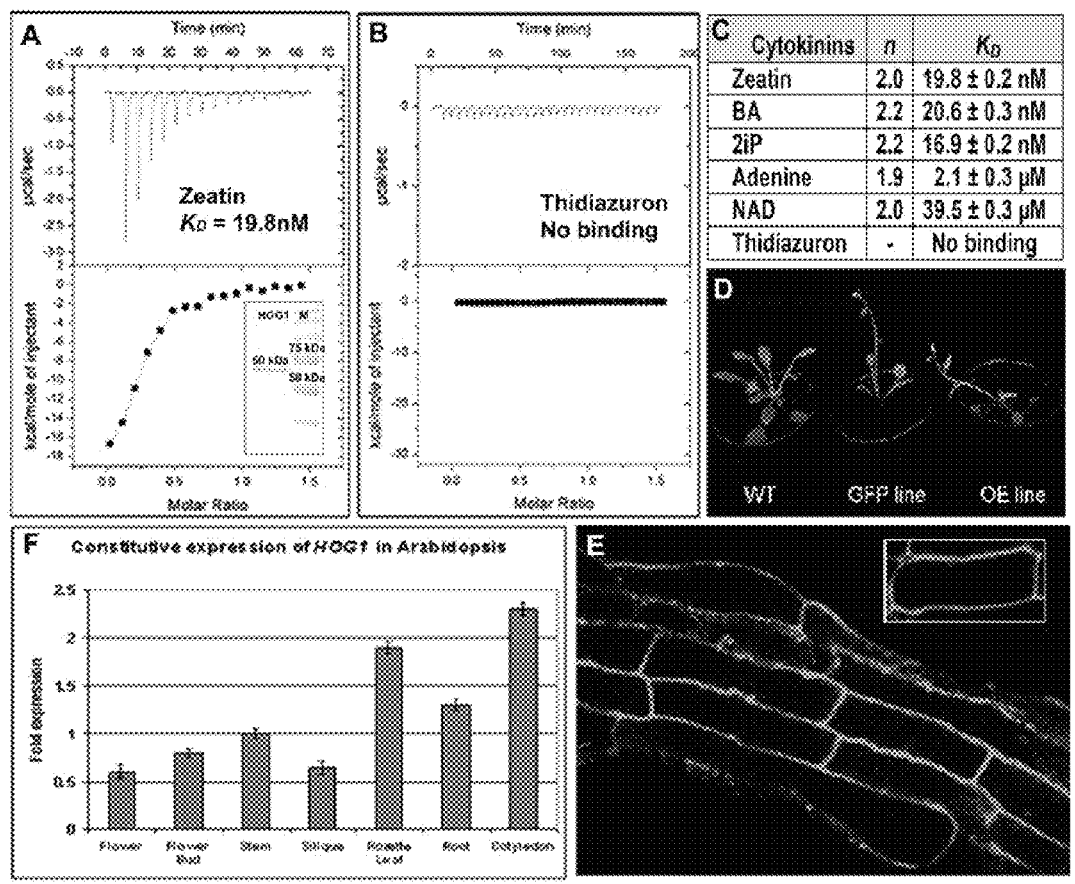
FIG. 1 shows the results of isothermal titration calorimetry, HOG1 localization and expression analysis. A) Cytokinin binding assay was performed with ITC. The top panel shows raw heat data corrected to baseline drift obtained from injections of 0.1 µM zeatin into the sample cell containing 2 µM purified TAP-HOG1. The bottom panel shows the binding isotherm created by plotting the heat peak areas against the molar ratio of zeatin added to HOG1. The inset shows purified TAP-HOG1 protein (60 kDa) from the transgenic plants. B) Assay with the urea-derived synthetic cytokinin, thidiazuron performed as with zeatin. C) The HOG1-cytokinin binding is endothermic with 2:1 stoichiometry. The KD values ranged from 16.9 nM to 20.6 nM for the three cytokinins tested, namely, zeatin, benzyladenine (BA) and 2-isopentenyladenine (2iP). KD values for adenine and NAD+ were 2.1 µM and 39.5 µM, respectively, showing the cytokinin specificity of HOG1. D) Transgenic lines expressing GFP-HOG1 fusion protein exhibited the same phenotype as 35S:HOG1 lines showing that the fusion protein retained its function. E) GFP-HOG1 fusion protein was localized in the plasma membrane. Live seedling root cell imaging was carried out using confocal laser scanning microscope (Zeiss CLSM 510) with 488 nm argon laser in combination with a 505- to 530-nm bandpass filter set. The inset shows, in a single cell, the protein is localized to the plasma membrane. F) Quantitative real-time PCR analysis of expression of HOG1 showed that the gene is constitutively expressed in all plant parts examined.

The binding stoichiometry, as determined by ITC, showed that two HOG1 monomers bind one cytokinin molecule (stoichiometry of 2:1) (FIG. 1A-1C), but does not bind thidiazuron (FIGS. 1B and 1C). This shows the specificity of HOG1 in binding cytokinins.

As can be seen from FIG. 1C, the dissociation constant (KD) ranged between 16.9 to 20.6 nM for the different cytokinins tested. Furthermore, the KD for adenine was 2.1 µM, which suggests a significantly lower affinity of HOG1 for adenine than for the cytokinin molecules. This is consistent with the fact that adenine elicits only weak cytokinin response when used at relatively high concentrations in some tissue cultures.

Since $NAD^+$ is the known cofactor for SAHH, KD value for HOG1 and $NAD^+$ complex by ITC was measured and found to be 39.5 µM (FIG. 1C), which further suggests that HOG1 is a cytokinin receptor and is not likely a functional SAHH enzyme.

(b) HOG1 is Localized on the Plasma Membrane

A domain search for the HOG1 protein was conducted using the PHDhtm web resource from Columbia University. The search showed that the HOG1 protein has a typical receptor-like structure. The HOG1 protein has a predicted transmembrane helix (spanning 18 amino acids from residues 59 to 76 of SEQ ID NO: 1), and the predicted cytokinin-binding domain (spanning 409 amino acids from residues 77 to 485 of SEQ ID NO: 1) resides outside the membrane. The protein also has a putative site inside the cytoplasm for interaction with downstream signaling intermediates, which comprises 58 amino acids at the N-terminal (from residues 1 to 58 of SEQ ID NO: 1).

To physically determine the sub-cellular localization of the HOG1 protein, transgenic *Arabidopsis* plants expressing green fluorescent protein (GFP)-HOG1 fusion were generated. Of the seven independent GFP lines isolated, three were selected for analysis. T3 generation transgenic plants expressing the GFP-HOG1 fusion protein showed the same phenotype as HOG1 over-expression lines (FIG. 1D), which indicates that the fusion protein had retained its function.

Confocal laser scanning microscopy of freshly cut roots from the selected lines and mounted in half strength MS medium showed that GFP-HOG1 is located on the plasma membrane (FIG. 1E), which suggests that HOG1 is a membrane receptor for cytokinins. As control, an earlier report for *Arabidopsis* was used, where 35S:GFP was shown to be fairly uniformly expressed in the cytoplasm and nucleus (Zhang Plant Cell 17:1306-1316, 2005). Based on the sequence analysis, a helical transmembrane region (spanning 18 amino acids) is present in HOG1 and other plant homologs, but not in the human and rat SAHH (FIG. 6), both of which are cytoplasmic proteins (Shu et al. *Proc. Natl. Acad. Sci. USA* 103:19788-19793). Moreover, active SAHH enzyme is expected to be a soluble protein, rather than remain plasma membrane bound, because the enzyme is closely associated with methylation reactions occurring in various cellular compartments. Hence, the present experimental results with GFP-HOG1 suggest that the HOG1 protein is a membrane receptor.

(c) HOG1 Over-Expression and Anti-Sense Suppression Plants Show Opposing Phenotypes Quantitative real-time PCR analysis indicated that HOG1 is constitutively expressed in *Arabidopsis*, with relatively higher levels in the leaves and inflorescence stem (FIG. 1F). This suggests that HOG1 may play a fundamental role in regulating plant development.

To examine the effect of modulating HOG1 expression levels on plant growth and development, various HOG1 over-expression and anti-sense suppression lines were generated. Various HOG1 over-expression lines showed a 3- to 20-fold increase in HOG1 transcript levels when compared to the wild type (FIG. 2A), while the anti-sense lines showed a 2- to 10-fold suppression (FIG. 2B).

Transgene expression affected all stages of plant development and exhibited consistent phenotypes in several independent transgenic lines (FIGS. 2C, 2D, 2E and 2F). Phenotypes were recorded for 28 independent transgenic over-expression lines and 21 anti-sense suppression lines to provide further support that the changes were caused by the introduced gene product. Seed germination occurred 4 to 5 days earlier in the over-expression lines compared to the wild type, and almost 5 days later in the anti-sense suppression lines compared to the wild type (Table 1). Nevertheless, significant growth retardation was observed soon after germination of the over-expression lines. The formation and expansion of new rosette leaves were also delayed and limited throughout vegetative growth in the over-expression lines.

TABLE 1

Seed germination, onset of flowering and senescence: Five independent lines were used for each observation. For each line the data are a mean from three independent replicates. The anti-sense lines showed late germination, late bolting and delayed senescence.

| Plant genotype | Seed germination (Number of days) | Onset of flowering/ Bolting (Number of rossette leaves) | Senescence (Number of days) |
|---|---|---|---|
| Wild-type (WT) *Arabidopsis* | | | |
| 1 | 8 | 8 | 40 |
| 2 | 7 | 8 | 40 |
| 3 | 8 | 8 | 38 |
| 4 | 9 | 7 | 40 |
| 5 | 8 | 8 | 40 |
| Mean ± SD | 8 ± 0.19 | 8 ± 0.15 | 40 ± 0.26 |
| Antisense lines | | | |
| AS1 | 13 | 14 | 55 |
| AS8 | 12 | 15 | 53 |
| AS14 | 13 | 14 | 54 |
| AS21 | 14 | 14 | 54 |
| AS19 | 13 | 15 | 53 |
| Mean ± SD | 13 ± 0.21 | 14 ± 0.11 | 54 ± 0.33 |
| Overexpression lines | | | |
| OE1 | 4 | 4 | 30 |
| OE8 | 4 | 3 | 32 |
| OE12 | 4 | 3 | 30 |
| OE18 | 5 | 4 | 28 |
| OE14 | 4 | 4 | 30 |
| Mean ± SD | 4 ± 0.13 | 4 ± 0.17 | 30 ± 0.28 |

The anti-sense suppression lines showed no retardation of shoot growth despite delayed seed germination. Early onset of flowering was observed in over-expression transgenic plants with bolting at 4 rosette leaf stage (FIG. 3A, Table 1), when compared to the wild type *Arabidopsis* and the anti-sense lines, which had at least 8 and 14 leaves, respectively, at the time of bolting (FIG. 3B, Table 1).

Figure 3:
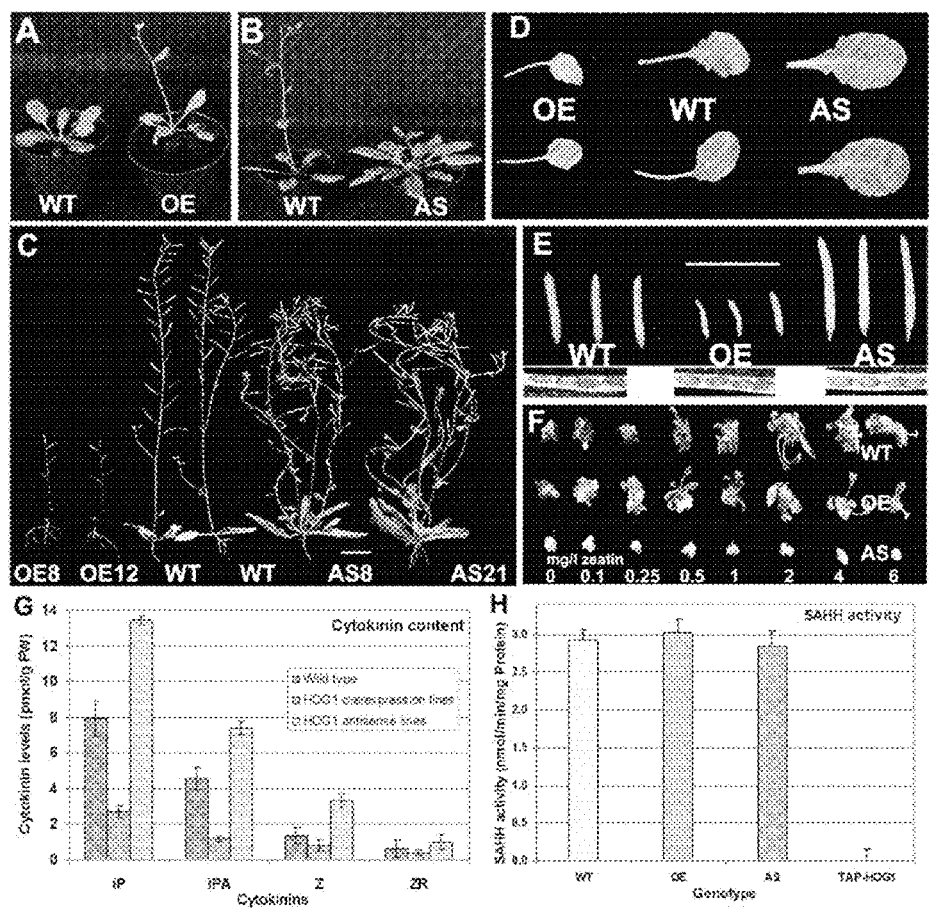
FIG. 3 shows the phenotypes of HOG1 over-expression (OE), anti-sense suppression (AS) and wild type (WT) plants. A) HOG1 OE lines show flowering when they had developed only four rosette leaves when the WT has not initiated flowering yet. B) AS lines of HOG1 show delayed flowering (14 leaves stage at the time of bolting) when the WT has well developed inflorescence. C) Comparison of phenotypes at maturity of the OE, WT and AS lines. An overall growth retardation of the OE lines and profuse branching phenotype of the AS lines at 30 days after germination when compared to the WT was seen. D) Increased rosette leaf size in the AS line compared to the WT and the OE lines. E) Silique size was increased in the AS lines compared to that of the WT, while it was significantly reduced in the OE lines (scale bar=1 cm). F) Response of calluses to various concentrations of exogenous cytokinin (zeatin) in the presence of the auxin indolebutyric acid (0.2 µg/ml). Callus from the AS lines exhibited a strong cytokinin-insensitive phenotype, i.e., weak stimulation of cell proliferation and lack of adventitious shoot induction after 3 weeks of culture. Callus from the OE line responded similarly to that of the WT, namely, both exhibited normal callus development and adventitious shoot induction, showing that HOG1 is a positive regulator of cytokinin. G) Quantification of cytokinin levels in the OE, WT and AS lines.

After initiation of flowering, the over-expression lines did not show any further increase in leaf biomass and no axillary inflorescence branches were formed even after 30 days of growth when senescence set in for these lines (FIG. 3C). In contrast, the anti-sense lines showed profuse development of axillary inflorescence branches and senescence was not evident in these lines during that period (FIG. 3C). The anti-sense lines also had the largest leaf area (2.94±0.15 $cm^2$ per leaf). The leaf area was significantly lower in the over-expression lines (0.38±0.06 $cm^2$) and the wild type plants (1.00±0.06 $cm^2$) (FIG. 3D, Tables 2 and 3). The overall plant stature, silique size and, as a result, the number and weight of seeds per silique (Tables 2 and 3) were significantly reduced in the over-expression lines, while the silique length in the anti-sense suppression lines was significantly higher than that of the wild type (FIG. 3E). There was a positive correlation between leaf area and seed weight per silique as well as leaf area and number of seeds per silique in the transgenic lines (Table 3).

TABLE 2

Leaf area, seed weight and number of seeds per silique: The data represent the mean ± SD from three independent replicates. Five independent lines were used in each case. The anti-sense lines had a three-fold increase in leaf biomass and a two-fold increase in seed yield compared to the wild type.

| Plant genotype | Leaf area ($cm^2$) | Seed weight per silique (mg) | Number of seeds per silique |
|---|---|---|---|
| Wild-type (WT) *Arabidopsis* | | | |
| 1 | 1.04 ± 0.02 | 1.13 ± 0.01 | 35 ± 0.01 |
| 2 | 1.01 ± 0.01 | 1.01 ± 0.02 | 30 ± 0.02 |

TABLE 2-continued

Leaf area, seed weight and number of seeds per silique: The data represent the mean ± SD from three independent replicates. Five independent lines were used in each case. The anti-sense lines had a three-fold increase in leaf biomass and a two-fold increase in seed yield compared to the wild type.

| Plant genotype | Leaf area (cm²) | Seed weight per silique (mg) | Number of seeds per silique |
|---|---|---|---|
| 3 | 0.90 ± 0.02 | 0.90 ± 0.02 | 26 ± 0.01 |
| 4 | 1.07 ± 0.02 | 1.18 ± 0.01 | 32 ± 0.01 |
| 5 | 0.98 ± 0.01 | 1.10 ± 0.01 | 29 ± 0.01 |
| Mean ± SD | 1.00 ± 0.07 | 1.06 ± 0.11 | 30.40 ± 0.36 |
| Antisense lines | | | |
| AS1 | 2.86 ± 0.01 | 1.79 ± 0.01 | 54 ± 0.02 |
| AS8 | 3.12 ± 0.01 | 2.40 ± 0.02 | 63 ± 0.02 |
| AS14 | 3.01 ± 0.02 | 1.96 ± 0.01 | 59 ± 0.02 |
| AS21 | 2.79 ± 0.02 | 1.96 ± 0.01 | 57 ± 0.01 |
| AS19 | 2.99 ± 0.02 | 2.00 ± 0.02 | 60 ± 0.01 |
| Mean ± SD | 2.95 ± 0.13 | 2.02 ± 0.22 | 58.60 ± 0.37 |
| Overexpression lines | | | |
| OE1 | 0.33 ± 0.02 | 0.68 ± 0.02 | 15 ± 0.01 |
| OE8 | 0.40 ± 0.02 | 0.72 ± 0.01 | 17 ± 0.01 |
| OE12 | 0.49 ± 0.02 | 0.81 ± 0.01 | 19 ± 0.02 |
| OE18 | 0.33 ± 0.02 | 0.70 ± 0.02 | 14 ± 0.02 |
| OE14 | 0.40 ± 0.01 | 0.83 ± 0.01 | 17 ± 0.02 |
| Mean ± SD | 0.39 ± 0.06 | 0.75 ± 0.07 | 16.40 ± 0.14 |

TABLE 3

Pearson's Correlation coefficient (r) of the parameters contributing to biomass and seed yield: Correlation coefficient was tested between: Leaf area (cm²) × Seed weight (mg) per silique (A); Leaf area (cm²) × Number of seeds per silique (B); and Seed weight per silique (mg) × Number of seeds per silique (C). After the correlation analysis, Student's t-test was performed. The t-test values are given in brackets. The 'r' values show positive correlation in all the tests. Based on this, it is predicted that anti-sense suppression of HOG1 leads to increase in the key parameters contributing towards leaf biomass and seed yield.

| Plant genotype | A | B | C |
|---|---|---|---|
| Wild type | 0.898 (t = 2.043) | 0.857 (t = 2.755) | 0.795 (t = 3.84) |
| HOG1 antisense lines | 0.763 (t = 2.043) | 0.847 (t = 2.755) | 0.912 (t = 3.84) |
| HOG1 overexpression lines | 0.769 (t = 2.078) | 0.979 (t = 2.878) | 0.767 (t = 2.269) |

The over-expression lines matured earlier when compared to wild type plants, the over-expression lines having matured earlier than the wild type plants by almost one week (FIG. 3A), while the anti-sense suppression lines matured later than the wild type by two weeks. Furthermore, senescence was delayed in the anti-sense suppression lines of HOG1 by two weeks when compared to the wild type *Arabidopsis* (FIG. 3C, Table 1).

To study the role of HOG1 as a cytokinin receptor, callus cultures of transgenic HOG1 plants were examined for their sensitivity to exogenous cytokinins similar to the study with CRE1 (Inoue et al. supra). Unlike shoot apical meristems in whole plants, callus cultures have the potential to respond to the exogenous cytokinins provided in the nutrient medium and are not dependent on long distance transport of the hormone as in the intact plants. Callus cultures from HOG1 over-expression lines and the wild type exhibited normal cell proliferation and adventitious shoot induction (FIG. 3F). In contrast, callus from the anti-sense HOG1 lines exhibited a strong cytokinin insensitive phenotype, namely, absence of cell proliferation and lack of adventitious shoot induction at all the concentrations of zeatin supplied (FIG. 3F). These data show that HOG1 functions as a positive regulator of cytokinin response.

(d) Contrasting Phenotypes of Transgenic Plants are Correlated with the Endogenous Cytokinin Levels The triple loss-of-function mutants of AHK-type cytokinin receptors caused an opposite phenotype (Higuchi et al. *Proc. Natl. Acad. Sci. USA* 101:8821-8826, 2004) to what was observed with the present anti-sense suppression of HOG1. This contradictory phenotype may be explained by the potential impediment to cytokinin translocation by the HOG1 protein in the over-expression lines.

The endogenous cytokinin content was determined for three independent lines each of the wild type, over-expression and anti-sense suppression lines. The concentrations of different cytokinins measured were reduced significantly in the over-expression lines compared with the wild type (FIG. 3G). Isopentenyl adenine is the predominant cytokinin of *Arabidopsis*, and its concentration was reduced by about 60% in the over-expression lines compared to that of the wild type (FIG. 3G). The higher availability of the protein in the over-expression lines may pose an impediment to the transport of cytokinins across the plasma membrane, especially because cytokinins have to be translocated from the roots to the shoot apical meristem. This will lead to an apparent loss-of-function phenotype, namely, reduced plant stature and lack of vegetative biomass, as observed (FIG. 3A).

In contrast, in the anti-sense lines, the concentration of isopentenyl adenine was increased by over 60% compared to the wild type, which corresponds to more than a four-fold increase over the over-expression lines (FIG. 3G). This resulted in the opposite phenotype of profuse branching and significant gain of biomass.

To test this experimentally, the effect of exogenous application of cytokinins on the phenotypes of the transgenic lines was studied. The over-expression lines receiving 0.01 µM zeatin or 0.01 µM kinetin spray on alternate days from the seedling stage showed bolting at the 6 to 7 leaf stage when compared to the untreated over-expression lines, which bolted at the 4 leaf stage (FIG. 2G, 2H, 2I, 2J and FIG. 7). The wild type *Arabidopsis* bolted at around the 8 leaf stage, indicating that the over-expression lines were 'partially rescued' by the exogenous application of cytokinins.

Furthermore, the anti-sense suppression lines showed no significant change in response to the exogenous application of cytokinins (FIG. 7), supporting the view that the impediment to cytokinin translocation is likely to be responsible for the contradictory phenotypes observed in our study.

(e) Purified HOG1 Lacks SAHH Enzyme Activity

No significant differences in SAHH activities in the crude protein extracts (FIG. 3H) from the wild type (2.92±0.15 nmol/min/mg protein), anti-sense (2.84±0.21 nmol/min/mg protein) and over-expression lines (3.02±0.19 nmol/min/mg protein) despite the earlier report that the hog1 point mutants had slightly lower SAHH activities in the crude protein extracts (Rocha et al. Plant Cell 17:404-417, 2005) compared to that of the wild type. More importantly, the present data showed that purified TAP-HOG1 protein lacks SAHH enzyme activity (FIG. 3H). These results suggest that the present HOG1 protein may be a cytokinin receptor.

Furthermore, it was highlighted in Rocha et al (supra) that the minor differences in SAHH activity measured in crude protein extracts of the point mutant (hog1-1) may be dependent on some other locus. Additionally, reduction of SAHH activity should lead to an increase in SAH levels and a decrease in the ratio of SAM:SAH. However, it was shown that the hog1-1 homozygote showed insignificant increase in SAH levels and the shift in SAM:SAH ratio was relatively small. The genome wide hypomethylation shown in these mutants was also in contrast with the hypomethylation of tobacco genome in suspension cultures induced by (S)-9-(2,3-dihydroxypropyl)adenine, which occurred only when the SAM:SAH ratio decreased by 300-folds relative to untreated material. These results suggested that the cytokinin binding proteins with sequence similarity to SAHH in plants may not be active SAHH enzymes but may instead be cytokinin receptors.

(f) HOG1 Affects the Expression of Cytokinin Primary Response Genes

Although the tissue culture response supports the view that HOG1 is a positive regulator of cytokinin response, it involved over six weeks of in vitro growth, during which other processes may have also contributed to the phenotype. Therefore, the expression of selected genes that are known to be directly induced by cytokinins at relatively short periods was also examined (FIG. 4A, 4B and Table 4). These genes included KNAT1 and STM (homeobox genes involved in meristem function, induced within 5 minutes after application of exogenous cytokinins) as well as ARR4, ARR5 and ARR6 (which are the type-A response regulators induced by cytokinins). Quantitative real-time PCR analysis was carried out using RNA from seedlings of wild type, HOG1 over-expression and HOG1 anti-sense suppression lines before and after a pulse treatment with cytokinin (benzyladenine, BA, at 0 μM, 0.01 μM, 0.1 μM, 1 μM or 5 μM). RNA extraction was carried out on tissues harvested over several time intervals (5 min, 15 min, 30 min and 1 h). Application of BA caused a dose-dependent increase of KNAT1 and STM transcripts, which was commensurate with the level of expression of HOG1 and the endogenous cytokinin concentrations in the lines (FIG. 4A, 4B, Table 4). The transcript levels of KNAT1 and STM were significantly up-regulated by 6- to 8-folds even without BA treatment in the HOG1 anti-sense suppression lines, whereas the untreated over-expression lines showed a 4- to 7-fold decrease of these transcripts when compared to the untreated wild type (FIG. 4A). However, within 1 h after application of 5 μM BA, the over-expression lines (e.g., OE1 and OE12) showed no significant difference in the levels of KNAT1 and STM transcripts compared to that of the untreated wild type plants (FIG. 4A, Table 4). This is consistent with the observation that this line has reduction in endogenous cytokinin levels.

TABLE 4

Quantitative real-time PCR analysis of selected cytokinin responsive genes: RNA from seedlings of wild type, HOG1 over-expression and anti-sense suppression lines before and after a pulse treatment with cytokinin (benzyladenine, BA, at 0 μM, 0.01 μM, 0.1 μM, 1 μM or 5 μM). RNA extraction was carried out using tissues harvested over several time intervals (5 min, 15 min, 30 min and 1 h) from three independent anti-sense suppression (AS1, AS8, AS21) and over-expression (OE1, OE12, OE18) lines. The genes analyzed include KNAT1, STM (homeobox genes involved in meristem function), ARR4, ARR5 and ARR6 (type-A response regulators induced by cytokinins). Application of BA caused a dose-dependent increase of KNAT1 and STM transcripts (arrows next to the fold change values indicate upregulation ↑ or down regulation ↓). ARR1, ARR2 (type-B response regulators), AHK2, AHK3, AHK4 (histidine kinase cytokinin receptors) were also analyzed. However, the data are not shown in this Table because thesegenes exhibited less than a two-fold change in expression.

| Gene | BA concentration | Time | Wild type | AS1 | AS8 | AS21 | OE1 | OE12 | OE18 |
|---|---|---|---|---|---|---|---|---|---|
| KNAT1 | 0 μM | 5 min | 1 | 6.12↑ | 7.36↑ | 8.69↑ | 4.91↓ | 5.01↓ | 7.20↓ |
| | | 15 min | 1 | 6.12↑ | 7.36↑ | 8.69↑ | 4.91↓ | 5.01↓ | 7.20↓ |
| | | 30 min | 1 | 6.12↑ | 7.36↑ | 8.69↑ | 4.91↓ | 5.01↓ | 7.20↓ |
| | | 1 h | 1 | 6.12↑ | 7.36↑ | 8.69↑ | 4.91↓ | 5.01↓ | 7.20↓ |
| | 0.01 μM | 5 min | 2.13↑ | 8.12↑ | 9.1↑ | 10.01↑ | 4.01↓ | 4.87↓ | 6.56↓ |
| | | 15 min | 2.67↑ | 8.57↑ | 9.21↑ | 10.39↑ | 3.86↓ | 4.56↓ | 6.32↓ |
| | | 30 min | 2.98↑ | 8.98↑ | 9.86↑ | 10.53↑ | 3.41↓ | 4.13↓ | 6.13↓ |
| | | 1 h | 3.15↑ | 9.20↑ | 9.98↑ | 11.99↑ | 3.01↓ | 3.06↓ | 5.98↓ |
| | 0.1 μM | 5 min | 3.36↑ | 9.14↑ | 10.12↑ | 11.11↑ | 3.56↓ | 3.91↓ | 5.89↓ |
| | | 15 min | 3.58↑ | 9.39↑ | 10.32↑ | 11.26↑ | 3.24↓ | 3.71↓ | 5.72↓ |
| | | 30 min | 3.89↑ | 9.69↑ | 10.57↑ | 11.48↑ | 3.12↓ | 3.59↓ | 5.36↓ |
| | | 1 h | 3.99↑ | 9.98↑ | 10.99↑ | 11.83↑ | 2.96↓ | 3.21↓ | 5.01↓ |
| | 1.0 μM | 5 min | 4.1↑ | 10.43↑ | 11.01↑ | 11.93↑ | 2.76↓ | 3.19↓ | 4.36↓ |
| | | 15 min | 4.31↑ | 10.68↑ | 11.43↑ | 12.02↑ | 2.51↓ | 3.01↓ | 4.21↓ |
| | | 30 min | 4.59↑ | 10.73↑ | 11.69↑ | 12.35↑ | 2.29↓ | 2.89↓ | 4.01↓ |
| | | 1 h | 4.87↑ | 11.01↑ | 11.93↑ | 12.76↑ | 2.01↓ | 2.16↓ | 3.92↓ |
| | 5.0 μM | 5 min | 5.52↑ | 10.98↑ | 11.98↑ | 12.43↑ | 2.19↓ | 2.87↓ | 3.45↓ |
| | | 15 min | 5.69↑ | 11.01↑ | 12.07↑ | 12.54↑ | 2.01↓ | 2.62↓ | 3.18↓ |
| | | 30 min | 5.89↑ | 11.23↑ | 12.48↑ | 12.87↑ | 1.83↓ | 2.49↓ | 3.01↓ |
| | | 1 h | 6.04↑ | 11.46↑ | 13.43↑ | 12.96↑ | 1.54↓ | 1.83↓ | 2.89↓ |
| ARR4 | 0 μM | 5 min | 1 | 3.12↑ | 5.36↑ | 7.69↑ | 5.91↓ | 6.01↓ | 8.2↓ |
| | | 15 min | 1 | 3.12↑ | 5.36↑ | 7.69↑ | 5.91↓ | 6.01↓ | 8.2↓ |
| | | 30 min | 1 | 3.12↑ | 5.36↑ | 7.69↑ | 5.91↓ | 6.01↓ | 8.2↓ |
| | | 1 h | 1 | 3.12↑ | 5.36↑ | 7.69↑ | 5.91↓ | 6.01↓ | 8.2↓ |
| | 0.01 μM | 5 min | 3.13↑ | 4.12↑ | 6.1↑ | 8.01↑ | 5.01↓ | 5.87↓ | 7.56↓ |
| | | 15 min | 3.67↑ | 4.57↑ | 6.41↑ | 8.39↑ | 4.66↓ | 5.56↓ | 7.32↓ |
| | | 30 min | 3.98↑ | 4.98↑ | 6.86↑ | 8.53↑ | 4.41↓ | 5.13↓ | 7.13↓ |
| | | 1 h | 4.15↑ | 5.2↑ | 6.98↑ | 8.99↑ | 4.01↓ | 4.06↓ | 6.98↓ |

TABLE 4-continued

Quantitative real-time PCR analysis of selected cytokinin responsive genes: RNA from seedlings of wild type, HOG1 over-expression and anti-sense suppression lines before and after a pulse treatment with cytokinin (benzyladenine, BA, at 0 μM, 0.01 μM, 0.1 μM, 1 μM or 5 μM). RNA extraction was carried out using tissues harvested over several time intervals (5 min, 15 min, 30 min and 1 h) from three independent anti-sense suppression (AS1, AS8, AS21) and over-expression (OE1, OE12, OE18) lines. The genes analyzed include KNAT1, STM (homeobox genes involved in meristem function), ARR4, ARR5 and ARR6 (type-A response regulators induced by cytokinins). Application of BA caused a dose-dependent increase of KNAT1 and STM transcripts (arrows next to the fold change values indicate upregulation ↑ or down regulation ↓). ARR1, ARR2 (type-B response regulators), AHK2, AHK3, AHK4 (histidine kinase cytokinin receptors) were also analyzed. However, the data are not shown in this Table because thesegenes exhibited less than a two-fold change in expression.

| Gene | BA concentration | Time | Wild type | AS1 | AS8 | AS21 | OE1 | OE12 | OE18 |
|---|---|---|---|---|---|---|---|---|---|
| | 0.1 μM | 5 min | 4.36↑ | 5.14↑ | 7.12↑ | 9.11↑ | 4.56↓ | 4.91↓ | 6.89↓ |
| | | 15 min | 4.58↑ | 5.39↑ | 7.32↑ | 9.26↑ | 4.24↓ | 4.71↓ | 4.72↓ |
| | | 30 min | 4.89↑ | 5.69↑ | 7.57↑ | 9.48↑ | 4.12↓ | 4.59↓ | 4.36↓ |
| | | 1 h | 4.99↑ | 5.98↑ | 7.99↑ | 9.83↑ | 3.96↓ | 4.21↓ | 4.01↓ |
| | 1.0 μM | 5 min | 5.1↑ | 6.43↑ | 8.01↑ | 9.93↑ | 3.76↓ | 4.19↓ | 3.36↓ |
| | | 15 min | 5.31↑ | 6.68↑ | 8.43↑ | 10.02↑ | 3.51↓ | 4.01↓ | 3.21↓ |
| | | 30 min | 5.59↑ | 6.73↑ | 8.69↑ | 10.35↑ | 3.29↓ | 3.89↓ | 3.01↓ |
| | | 1 h | 5.87↑ | 7.01↑ | 8.93↑ | 10.76↑ | 3.01↓ | 3.56↓ | 2.92↓ |
| | 5.0 μM | 5 min | 6.52↑ | 6.98↑ | 8.98↑ | 10.43↑ | 3.19↓ | 3.87↓ | 2.45↓ |
| | | 15 min | 6.69↑ | 7.01↑ | 9.07↑ | 10.54↑ | 3.01↓ | 3.62↓ | 2.18↓ |
| | | 30 min | 6.89↑ | 7.23↑ | 9.46↑ | 10.87↑ | 2.83↓ | 3.49↓ | 2.01↓ |
| | | 1 h | 7.04↑ | 7.46↑ | 9.63↑ | 10.96↑ | 2.54↓ | 2.13↓ | 1.89↓ |
| STM | 0 μM | 5 min | 1 | 3.01↑ | 5.24↑ | 6.56↑ | 3.56↓ | 5.21↓ | 6.59↓ |
| | | 15 min | 1 | 3.01↑ | 5.24↑ | 6.56↑ | 3.56↓ | 5.21↓ | 6.59↓ |
| | | 30 min | 1 | 3.01↑ | 5.24↑ | 6.56↑ | 3.56↓ | 5.21↓ | 6.59↓ |
| | | 1 h | 1 | 3.01↑ | 5.24↑ | 6.56↑ | 3.56↓ | 5.21↓ | 6.59↓ |
| | 0.01 μM | 5 min | 2.45↑ | 3.23↑ | 5.2↑ | 7.1↑ | 3.41↓ | 4.97↓ | 6.23↓ |
| | | 15 min | 2.54↑ | 3.67↑ | 5.58↑ | 7.48↑ | 3.23↓ | 4.65↓ | 6.02↓ |
| | | 30 min | 3.01↑ | 3.91↑ | 5.95↑ | 7.69↑ | 3.01↓ | 4.31↓ | 5.91↓ |
| | | 1 h | 3.2↑ | 4.1↑ | 6.06↑ | 8.05↑ | 2.81↓ | 3.96↓ | 5.82↓ |
| | 0.1 μM | 5 min | 3.56↑ | 4.24↑ | 6.22↑ | 8.21↑ | 3.2↓ | 3.81↓ | 5.79↓ |
| | | 15 min | 3.68↑ | 4.49↑ | 6.39↑ | 8.36↑ | 3.14↓ | 3.73↓ | 5.61↓ |
| | | 30 min | 3.85↑ | 4.79↑ | 6.63↑ | 8.58↑ | 2.92↓ | 3.49↓ | 5.34↓ |
| | | 1 h | 3.96↑ | 4.97↑ | 6.94↑ | 8.87↑ | 2.76↓ | 3.01↓ | 5.01↓ |
| | 1.0 μM | 5 min | 4.11↑ | 5.53↑ | 7.8↑ | 8.89↑ | 2.86↓ | 2.89↓ | 4.26↓ |
| | | 15 min | 4.36↑ | 5.78↑ | 7.93↑ | 9.02↑ | 2.61↓ | 2.56↓ | 4.11↓ |
| | | 30 min | 4.69↑ | 5.83↑ | 7.99↑ | 9.25↑ | 2.39↓ | 2.87↓ | 4.01↓ |
| | | 1 h | 4.97↑ | 6.21↑ | 8.07↑ | 9.66↑ | 2.11↓ | 2.62↓ | 3.82↓ |
| | 5.0 μM | 5 min | 5.62↑ | 6.01↑ | 8.46↑ | 9.33↑ | 2.29↓ | 2.49↓ | 3.35↓ |
| | | 15 min | 5.89↑ | 6.21↑ | 8.63↑ | 9.44↑ | 2.11↓ | 2.13↓ | 3.28↓ |
| | | 30 min | 5.99↑ | 6.43↑ | 8.73↑ | 9.67↑ | 1.93↓ | 2.01↓ | 3.01↓ |
| | | 1 h | 6.14↑ | 6.76↑ | 8.99↑ | 9.86↑ | 1.44↓ | 1.68↓ | 2.79↓ |
| ARR5 | 0 μM | 5 min | 1 | 4.11↑ | 6.34↑ | 7.63↑ | 4.66↓ | 6.31↓ | 7.49↓ |
| | | 15 min | 1 | 4.11↑ | 6.34↑ | 7.63↑ | 4.66↓ | 6.31↓ | 7.49↓ |
| | | 30 min | 1 | 4.11↑ | 6.34↑ | 7.63↑ | 4.66↓ | 6.31↓ | 7.49↓ |
| | | 1 h | 1 | 4.11↑ | 6.34↑ | 7.63↑ | 4.66↓ | 6.31↓ | 7.49↓ |
| | 0.01 μM | 5 min | 3.55↑ | 4.33↑ | 6.12↑ | 8.2↑ | 4.51↓ | 5.87↓ | 7.33↓ |
| | | 15 min | 3.64↑ | 4.77↑ | 6.68↑ | 8.58↑ | 4.33↓ | 5.55↓ | 7.03↓ |
| | | 30 min | 4.11↑ | 5.01↑ | 6.82↑ | 8.79↑ | 4.11↓ | 5.21↓ | 6.91↓ |
| | | 1 h | 4.3↑ | 5.11↑ | 7.16↑ | 9.15↑ | 3.91↓ | 4.96↓ | 6.63↓ |
| | 0.1 μM | 5 min | 4.66↑ | 5.34↑ | 7.32↑ | 9.31↑ | 4.1↓ | 4.71↓ | 6.69↓ |
| | | 15 min | 4.78↑ | 5.59↑ | 7.49↑ | 9.46↑ | 4.04↓ | 4.63↓ | 6.51↓ |
| | | 30 min | 4.95↑ | 5.89↑ | 7.73↑ | 9.68↑ | 3.9↓ | 4.4↓ | 6.23↓ |
| | | 1 h | 5.06↑ | 6.07↑ | 8.04↑ | 9.97↑ | 3.67↓ | 4.01↓ | 6.01↓ |
| | 1.0 μM | 5 min | 5.21↑ | 6.62↑ | 8.59↑ | 9.99↑ | 3.96↓ | 3.99↓ | 5.36↓ |
| | | 15 min | 5.46↑ | 6.88↑ | 8.93↑ | 10.12↑ | 3.71↓ | 3.46↓ | 5.21↓ |
| | | 30 min | 5.79↑ | 6.93↑ | 9.09↑ | 10.35↑ | 3.49↓ | 3.77↓ | 5.01↓ |
| | | 1 h | 6.07↑ | 7.31↑ | 9.17↑ | 10.76↑ | 3.21↓ | 3.52↓ | 4.72↓ |
| | 5.0 μM | 5 min | 6.72↑ | 7.01↑ | 9.56↑ | 10.43↑ | 3.19↓ | 3.59↓ | 4.25↓ |
| | | 15 min | 6.99↑ | 7.31↑ | 9.73↑ | 10.56↑ | 3.01↓ | 3.13↓ | 4.18↓ |
| | | 30 min | 7.09↑ | 7.53↑ | 9.83↑ | 10.71↑ | 2.83↓ | 3↓ | 4↓ |
| | | 1 h | 7.24↑ | 7.86↑ | 10.05↑ | 10.93↑ | 2.54↓ | 2.78↓ | 3.89↓ |
| ARR6 | 0 μM | 5 min | 1 | 4.12↑ | 6.36↑ | 8.63↑ | 5.66↓ | 7.01↓ | 9.2↓ |
| | | 15 min | 1 | 4.12↑ | 6.36↑ | 8.63↑ | 5.66↓ | 7.01↓ | 9.2↓ |
| | | 30 min | 1 | 4.12↑ | 6.36↑ | 8.63↑ | 5.66↓ | 7.01↓ | 9.2↓ |
| | | 1 h | 1 | 4.12↑ | 6.36↑ | 8.63↑ | 5.66↓ | 7.01↓ | 9.2↓ |
| | 0.01 μM | 5 min | 4.13↑ | 4.12↑ | 7.1↑ | 9.2↑ | 5.51↓ | 6.87↓ | 8.56↓ |
| | | 15 min | 4.67↑ | 4.57↑ | 7.41↑ | 9.58↑ | 5.33↓ | 6.56↓ | 8.32↓ |

TABLE 4-continued

Quantitative real-time PCR analysis of selected cytokinin responsive genes: RNA from seedlings of wild type, HOG1 over-expression and anti-sense suppression lines before and after a pulse treatment with cytokinin (benzyladenine, BA, at 0 µM, 0.01 µM, 0.1 µM, 1 µM or 5 µM). RNA extraction was carried out using tissues harvested over several time intervals (5 min, 15 min, 30 min and 1 h) from three independent anti-sense suppression (AS1, AS8, AS21) and over-expression (OE1, OE12, OE18) lines. The genes analyzed include KNAT1, STM (homeobox genes involved in meristem function), ARR4, ARR5 and ARR6 (type-A response regulators induced by cytokinins). Application of BA caused a dose-dependent increase of KNAT1 and STM transcripts (arrows next to the fold change values indicate upregulation ↑ or down regulation ↓). ARR1, ARR2 (type-B response regulators), AHK2, AHK3, AHK4 (histidine kinase cytokinin receptors) were also analyzed. However, the data are not shown in this Table because thesegenes exhibited less than a two-fold change in expression.

| Gene | BA concentration | Time | Wild type | AS1 | AS8 | AS21 | OE1 | OE12 | OE18 |
|------|------------------|------|-----------|-----|-----|------|-----|------|------|
| | | 30 min | 4.98↑ | 5.98↑ | 7.86↑ | 9.79↑ | 5.11↓ | 6.13↓ | 8.13↓ |
| | | 1 h | 5.15↑ | 6.2↑ | 7.98↑ | 10.15↑ | 4.91↓ | 5.06↓ | 7.98↓ |
| | 0.1 µM | 5 min | 5.36↑ | 6.14↑ | 8.12↑ | 10.31↑ | 5.1↓ | 5.91↓ | 7.89↓ |
| | | 15 min | 5.58↑ | 6.39↑ | 8.32↑ | 10.46↑ | 5.04↓ | 5.71↓ | 5.72↓ |
| | | 30 min | 5.89↑ | 6.69↑ | 8.57↑ | 10.68↑ | 4.9↓ | 5.59↓ | 5.36↓ |
| | | 1 h | 5.99↑ | 6.98↑ | 8.99↑ | 10.97↑ | 4.67↓ | 4.61↓ | 5.01↓ |
| | 1.0 µM | 5 min | 6.1↑ | 7.43↑ | 9.01↑ | 10.99↑ | 4.96↓ | 5.19↓ | 4.36↓ |
| | | 15 min | 6.31↑ | 7.68↑ | 9.43↑ | 11.12↑ | 4.71↓ | 5.01↓ | 4.21↓ |
| | | 30 min | 6.59↑ | 7.73↑ | 9.69↑ | 11.35↑ | 4.49↓ | 4.89↓ | 4.01↓ |
| | | 1 h | 6.87↑ | 8.01↑ | 9.93↑ | 11.76↑ | 3.21↓ | 3.56↓ | 3.01↓ |
| | 5.0 µM | 5 min | 7.52↑ | 7.98↑ | 9.98↑ | 11.43↑ | 4.19↓ | 4.67↓ | 3.45↓ |
| | | 15 min | 7.69↑ | 8.01↑ | 10.07↑ | 11.56↑ | 4.01↓ | 4.62↓ | 3.18↓ |
| | | 30 min | 7.89↓ | 8.23↑ | 10.46↑ | 11.71↑ | 3.83↓ | 3.49↓ | 3.01↓ |
| | | 1 h | 8.04↑ | 8.46↑ | 10.63↑ | 11.93↑ | 2.14↓ | 2.03↓ | 2.89↓ |

The level of expression of the genes examined was 3- to 6-folds higher in the anti-sense lines that have about a 4-fold higher endogenous concentration of cytokinins. Hence, HOG1 expression was shown to correlate to cytokinin response in these plants. This is similar to earlier reports that both STM and KNAT1 expressions were significantly elevated in *Arabidopsis* plants with elevated cytokinin biosynthesis caused by over-expressing the bacterial ipt gene (Rupp et al. *Plant J* 18:557-563, 1999). These observations indicate the direct involvement of HOG1 in regulating cytokinin responses during plant development.

Additionally, to determine whether the phenotypes of the HOG1 transgenic lines were associated with cytokinin signal transduction, the best known class of immediate-early genes induced by cytokinins, namely, type-A ARR genes—ARR4, ARR5 and ARR6 were studied (FIG. 4B). The present data showed that these genes were up-regulated within minutes after a single cytokinin pulse treatment, which is consistent with earlier observations in *Arabidopsis* (Brandstatter and Kieber *Plant Cell* 10:1009-1020, 1998; D'Agostino at el *Plant Physiol* 124:1706-1717, 2000; Taniguchi et al. *FEBS Lett.* 429:259-262, 1998; To et al. *Plant Cell* 16:658-671, 2004).

It was found that the HOG1 over-expression lines (e.g., OE12), which have a significant reduction in endogenous cytokinin levels (FIG. 3G), showed a 3- to 9-fold decrease in the expression levels of the three type-A ARR genes studied. This could be overcome to a large extent by BA treatment (FIG. 4B), which is consistent with reduced flux through the primary cytokinin signal transduction pathway. Similarly, the anti-sense HOG1 lines (e.g., AS8) with higher endogenous cytokinin levels had a correspondingly higher level (a 4- to 9-fold increase) of ARR expression (FIG. 4B and Table 4). These data show that the type-A ARR genes are downstream of the novel cytokinin receptor HOG1. Similarly, ARR6 was previously shown to be induced in response to exogenous cytokinins in over-expression lines of CRE1, which confirmed ARR6 to be a cytokinin receptor (Hwang and Sheen *Nature* 413:383-389, 2001).

Furthermore, the transcript levels of two type-B ARRs (ARR1 and ARR2) in these transgenic lines were studied to ensure that the observations on the type-A ARRs are specific responses. ARR1 and ARR2 were not significantly affected by the BA treatment under the present experimental conditions (Table 4), which is consistent with previous results (Imamura et al. *Proc. Natl. Acad. Sci. USA* 95:2691-2696, 1998; Kiba et al. *Plant Cell Physiol.* 40:767-771, 1999; Hutchison et al. *Plant Cell* 18:3073-3087, 2006).

In order to rule out the involvement of AHK-type cytokinin receptors, namely, AHK2, AHK3 and CRE1/AHK4, their transcript levels in the different transgenic lines were determined. No significant differences was seen in the HOG1 over-expression and anti-sense suppression lines compared to that of the wild type (data not shown), showing that HOG1 acts independently of these three known cytokinin receptors.

(g) TAP-HOG1 Interacts with AHP1

To determine the signaling complex formed by the HOG1 protein and further support its role as a cytokinin receptor, proteins interacting with HOG1 were isolated and identified.

Six independent transgenic *Arabidopsis* lines expressing HOG1 with an N-terminal TAP tag (TAP-HOG1) were generated. These plants had the same phenotype as the HOG1 over-expression lines, showing that the fusion protein is functional in the plants. Pull-down assays were performed with total protein extract from 3-week-old TAP-HOG1 transgenic plants. A protein band of 71 kDa was detected when an immunoblot analysis was performed using PAP antibody to detect the presence of the TAP-HOG1 fusion protein in these plants (FIG. 4C). The predicted molecular weight of HOG1 is 56 kDa and the tag is 15 kDa, thus accounting for the 71 kDa fusion protein band. The protein complex with TAP-HOG1 was eluted from total protein extract using the tags and IgG beads using the method of Forler et al. (supra). The protein complex was subjected to SDS-PAGE and N-terminal sequencing of the prominent protein band revealed that it was AHP1. Subsequently, the cDNA for AHP1 was cloned by PCR from *Arabidopsis* and recombinant AHP1 was expressed in *E. coli* (FIG. 4D). It was shown, using ITC, that AHP1 interacts directly with purified TAP-HOG1 protein (FIG. 4E). The dissociation constant KD value for the complex formed by the two purified proteins in ITC was 23.8 nM.

*Arabidopsis* Histidine Phosphotransfer proteins (AHP1, AHP2, AHP3, AHP4 and AHP5) are the key intermediates of cytokinin signaling, because they function as cytoplasmic nuclear shuttles between the membrane receptors and the nuclear response regulators. The demonstration that HOG1 interacts with AHP1, which is a key intermediate of cytokinin signal transduction, further confirmed the receptor function of the HOG1 protein.

The present data show that HOG1 is a novel cytokinin receptor in addition to the earlier described AHK-family receptors. Several homologs were isolated from *Brassica alboglabra, chrysanthemum, amaranthus* and rice. This shows that HOG1 is present in diverse plant species and is important in regulating plant development. The cytokinin signal transduction pathway described above is a phosphorelay pathway similar to the bacterial two component response systems. This is consistent with the fact that cytokinins play several roles in the regulation of plant development and the presence of more than one type of cytokinin receptors could facilitate such pleiotropic functions. Such a phenomenon has also been observed in ethylene signal transduction where more than one receptor (e.g., ETR1, ERS2, ETR2 and EIN4) is involved. Furthermore, the constitutive expression of HOG1 in all plant parts suggests a critical role for the protein in plant development.

The possibility that other receptors may exist for cytokinins was highlighted based on the observation that the triple mutant of histidine kinase cytokinin receptors (cre1-12ahk3-3ahk2-2(Col)) produced plants, albeit having severely dwarf and sterile phenotypes. Loss-of-function mutants in the three AHK-type cytokinin receptors caused opposite phenotypes compared to those observed with the present anti-sense suppression of the HOG1 gene. The contradictory phenotypes observed in the present study appears to be the result of altered endogenous cytokinin levels in the shoots. The high affinity binding of cytokinin molecules by the HOG1 protein was indicated by low KD values. When the gene was significantly over-expressed by two copies of the strong promoter (cauliflower mosaic virus 35S promoter) used in the present study, the resultant increase in the protein as well as ectopic expression led to a significant reduction in available free cytokinins (FIG. 3G). This is possibly due to the protein acting as an impediment to transport cytokinin across the plasma membrane. This is important because the shoot apex has to receive cytokinins from the root apex (which is the primary site of cytokinin biosynthesis). This led to an apparent loss-of-function phenotype, namely, reduced plant stature and lack of vegetative biomass.

In contrast, in the anti-sense plants, there is a significant increase in available free cytokinin molecules at the shoot apical meristem, leading to the opposite phenotype of profuse branching and significant gain of biomass (FIG. 3G).

Application of the TAP tag protein purification in plants has allowed the characterization of several protein complexes including the resistance protein Cf9 in tobacco and CTR1 protein in *Arabidopsis*. The present study identified *Arabidopsis* histidine phosphotransfer (AHP1) as a protein that interacts with HOG1, showing that AHP1 is a downstream signaling intermediate for HOG1. Recombinant AHP1 was expressed and shown to interact directly with purified TAP-HOG1 protein. The dissociation constant value for the complex formed by the two pure proteins in ITC was 23.8 nM, which provides important support for the receptor function of HOG1.

(h) HOG1 as a New Receptor for Cytokinin Signal Transduction Pathway

To better understand the role of the new cytokinin receptor HOG1 in mediating cytokinin response, the primary-response genes induced by cytokinins namely, type-A ARR genes (i.e. ARR4, ARR5 and ARR6) were analyzed. Changes in the expression levels of the ARRs were seen in FIG. 4B and Table 4, which in addition to the measured cytokinin content in HOG1 anti-sense and over-expression lines suggests that the response to endogenous cytokinin is affected by HOG1. This confirms the HOG1 protein as a new receptor and the ARRs as the downstream signaling cascade members of HOG1 cytokinin signal transduction pathway along with AHP1.

Hence, the present data provide a cytokinin signal transduction pathway via HOG1 in *Arabidopsis* in addition to the previously described two-component system (FIG. 5). It is important to note that genetic modification of the earlier reported histidine kinase receptors were not shown to affect vegetative and reproductive growth unlike the anti-sense suppression of HOG1. The present data show that this receptor will serve as a key target for biotechnological improvement of crop plants for increased yield of biomass and grain.

Example 2

Biomass and Grain Yield Increase in Rice by Anti-Sense Suppression of a Gene for a Putative Cytokinin Receptor Materials and Methods
Plant Materials For rice *Oryza sativa L. japonica*, cultivar Nipponbare was used. This is a commercial cultivar which originates from Japan. Similar work can also be carried out with other rice cultivars (indica subspecies). Wild type *Arabidopsis thaliana* seeds were obtained from LEHLE SEEDS (1102 South Industrial Blvd., Suite D, Round Rock Tex. 78681 USA).
Bacterial Strains The bacterial strain used for DNA cloning in this study was *Escherichia coli* DH5α, which was grown in liquid LB medium (Sambrook et al., 1989) at 37° C. except when indicated otherwise. The *Agrobacterium tumefaciens* strains used were GV3101 (Koncz and Schell, 1986).
PCR with Degenerate Primers for Cloning the Gene After RNA extraction, reverse transcription (RT) was performed using AMV (avian myeloblastosis virus) reverse transcriptase (AMV-RT, Promega). The cDNA products were used for PCR using the degenerate primers PET1: 5'-A(AG)ATGCC(CT)GG(ACT)CT(ACT)ATG(GT)C(ACT)T-3' (SEQ ID NO: 24) and PET2: 5'-TC(AG)AACTTGCTCT-TGGT(AG)AC(AG)-3' (SEQ ID NO: 25) to isolate the partial fragment from *Arabidopsis thaliana* and rice. The PCR fragment was cloned and sequenced.
Rapid Amplification of 5'- and 3'-cDNA Ends The SMART™ RACE cDNA Amplification Kit (Clontech Laboratories) was used to identify the 5'- and 3'-cDNA (5'/3'-

RACE) end sequences of cDNA. These PCR products were sequenced. The partial sequence and RACE PCR products were aligned together to obtain the full length cDNA sequence for *Arabidopsis thaliana* (HOG1) and rice (Os-CBP).

The gene construct used for *Agrobacterium*-mediated plant transformation was the anti-sense gene suppression (35S:asHOG1) construct. The promoter used was the Cauliflower Mosaic Virus (CaMV) 35S promoter.

Agrobacterium-Mediated Plant Transformation of Rice

The method of Hiei et al. (*Plant Journal* UK Vol. 6, pages 271-282, 1994) was used.

1. Rice Callus Induction

Mature rice seeds were surface sterilized with 70% ethanol for 1.5 min. Bleach (20%) was added with a drop of Tween-20, in a 100 ml sterile flask on a shaker at 120 rpm for 45 min. This was followed by rinsing the treated seeds thoroughly with sterile distilled water.

The sterilized seeds were placed on the surface of 30 ml solidified NB0 medium with 2.0 mg/l 2,4-D (callus induction medium) in sterile 9 cm deep plastic petri dishes. The plates were wrapped with tape and placed into a box in a tissue culture room and the rice seeds were allowed to germinate at 25° C. in darkness.

After 10 days, calluses derived from the scutellum were excised and sub-cultured on fresh callus induction medium. The subculture was carried out every 4 weeks until vigorously growing, light-yellow, embryogenic calluses were obtained.

2. Co-Cultivation of *Agrobacterium* with Rice Callus

Binary plasmids containing an anti-sense construct (based on pCAMBIA1301, R. Jefferson, CAMBIA, Australia) were introduced into *A. tumefaciens* strain AGL1. The *A. tumefaciens* was grown in storage on solidified YEP medium with 10 mg/L rifampicin, 50 mg/L kanamycin and 50 mg/L hygromycin at 28° C. for 48-73 hours. 1 ml of the bacterial culture was added to 100 ml of AB medium containing the same selective antibiotics in a 250 ml flask at 28° C. The bacteria were grown to achieve a density of OD595 at 0.8-1.0. The bacteria were collected by centrifugation at 4,000 rpm for 10 mins at room temperature. The supernatant was then removed and the bacteria were washed once by re-suspending the pellet in the same volume at AMM medium, and centrifuged again at 4,000 pm for 10 minutes at room temperature. The supernatant was discarded.

The bacteria were diluted with AMM medium to a density of OD595 at 0.4 (about: 109 cells per ml). About 20-25 ml of the diluted bacteria was used for *Agrobacterium* inoculation in sterile 9 cm plastic petri dishes. Vigorously growing, light-yellow, embryogenic calluses with the size of about 5 mm in diameter were selected and placed into the bacterial suspension and immersed for 30 minutes, with occasional shaking, in a sterile laminar flow hood. Excess bacterial suspension from the calluses was removed by placing the calluses on a pad of dry sterile tissue paper. The inoculated calluses were transferred (without rinsing) on to 2N6-AS medium in sterile 9 cm plastic petri dishes, and incubated at 25° C. in darkness for 2-3 days.

3. Selection and Regeneration of Transformants

The co-cultivated calluses in a 100 ml sterile flask were collected and washed with gentle shaking using 50-75 ml of sterile distilled water at least 10 times. The calluses were dried on a pad of sterile tissue paper to remove excess surface water. The callus pieces were transferred into 100 ml sterile distilled water with 500 mg/l cefotaxime and 200 mg/l ampicillin, and shaken for two hours at 120 rpm at 25° C. The water was removed and the callus pieces were blotted dry on a pad of sterile paper. The callus pieces were transferred on to NB0 medium with 2 mg/L 2,4-D, 250 mg/l cefotaxime, 200 mg/l ampicillin, and 50 mg/l hygromycin (selective medium) in sterile 9 cm petri dishes for the selection of transformed cells. The sealed dishes were incubated at 25° C. in darkness.

After a 4-week selection, the putative hygromycin-resistant microcalluses were extracted from co-cultivated calluses, transferred to the same fresh selective medium for resistance confirmation and tissue proliferation, and cultured for 3 weeks.

Vigorously growing hygromycin-resistant calluses were transferred to NB0 medium with 1.0 mg/l 6-BA, 2.0 mg/l NAA, 5.0 mg/l ABA and 50 mg/l hygromycin (pre-regeneration medium) and cultured at 25° C. in darkness for 3 weeks. The white compact hygromycin-resistant embryogenic calluses from the pre-regeneration medium were transferred to NB0 medium with 2.0 mg/l 6-BA, 1.0 mg/l IAA, 1.0 mg/l NAA, 1.0 mg/l KT and 50 mg/l hygromycin (regeneration medium), and cultured at 25° C. with 14 hours of light (about 2000 lux) and 8 hours of darkness.

The regenerated hygromycin-resistant plantlets were transferred three weeks later to 100 ml ½ MS medium with 50 mg/l hygromycin (plantlet growth medium) in Phytacon vessels for shoot induction and root elongation. The culture conditions were continued until the plantlets reached the top of the containers. Well-developed hygromycin-resistant plantlets were removed from the culture vessels and immediately put in tap water in a plastic tray to remove the attached medium. The plantlets were transferred to a 54-well (about 5 cm diameter) plastic tray containing ½ MS medium (solution). Each given cluster of plantlets (putative transgenic line) was put into a separate well. The plantlets were trained for 7-10 days in a growth chamber in 90% humidity at 20° C. with 14 hours of light (about 400 lux) and 8 hours of darkness.

The plants were transplanted to soil in pots and grown in a greenhouse as non-transgenic plants for three generations to obtain homozygous transgenic plants.

Supplementary Methods

Plant Materials and Growth Conditions

For *Arabidopsis thaliana*, the ecotype Columbia was used and the plants were grown in 16 hours of light and 8 hours of darkness at 22° C. in growth chambers. *Oryza sativa* L. ssp. *Japonica*, cultivar Nipponbare was used for rice genetic transformation experiments.

Plasmid Construction and Genetic Transformation of *Arabidopsis*

Full length HOG1 cDNA was amplified by 5' and 3' RACE strategy. pGreen 0229 binary vector (Yu et al. supra) was used for all the transgene constructs. For anti-sense suppression, an 850 bp fragment of HOG1 spanning the two SAHH signatures was used (SEQ ID NO: 15). The complete open reading frame of HOG1 cDNA was used for the over-expression construct (SEQ ID NO: 2). TAP-tagged HOG1 was with Prot A and calmodulin binding peptide tags with a TEV cleavage site between the two tags. The constructs were introduced into *Arabidopsis thaliana* by *Agrobacterium tumefaciens*-mediated floral dip method (Clough, S. and Bent, A. *The Plant Journal* 16(6):735-743 (1998)).

Real-Time Quantitative PCR Analysis

Total RNA was extracted from *Arabidopsis* seedlings or rice leaves with the TRIzol method (Invitrogen). Total RNA (0.5 µg) treated with RNase-free DNaseI was used for each quantitative PCR reaction performed with the One-Step RT kit (Qiagen) according to the manufacturer's instructions. Quantitative real-time PCR was performed using SYBR green (Applied Biosystems Inc.). The Ct values were normalized against the Tubulin2 Ct value for calculation of fold-change according to the manufacturer's protocol.

Isothermal Titration Calorimetry (ITC)

Cytokinin binding affinity and thermodynamic analysis of the interaction between HOG1 and cytokinins was examined by ITC (MCSITC, Microcal, Northampton, USA). TAP-HOG1 fusion protein was purified using published protocols (Forler et al. supra) from transgenic *Arabidopsis* plants harboring the 35S:TAP-HOG1 construct. 0.01 µM benzyladenine (a naturally occurring cytokinin) and 0.1 µM of purified TAP-HOG1 protein were used for each ITC assay with 25 injections (each injection of 2 µl at 3 s intervals at 37° C.). Data were analyzed with MICROCAL ORIGIN version 2.9 using the best-fit, nonlinear least-squares method for one binding site. The binding stoichiometry (n), and association constant (KA) were calculated from the fitted curves. Subsequently, KD was calculated as 1/KA.

Cytokinin Content

Cytokinins were extracted from whole plants with 100% methanol and quantified using isopentenyl adenosine detection kit (Sigma) as described in Yang et al. (supra).

Rice Callus Induction

Surface sterilized and dehusked rice seeds were induced for callus production by placing them on NBO medium supplemented with 2 mg/L of 2,4-D (callus induction medium) and then incubating them at 25° C. for 30 days in the dark. After 30 days, further sub-culturing of the emerging calluses was done until friable embryonic calluses were obtained.

Co-Cultivation of *Agrobacterium* with Rice Callus

The binary plasmid pCAMBIA 1300 containing the full length HOG1 (sense or anti-sense orientations for over-expression and anti-sense suppression, respectively) was introduced into *Agrobacterium tumefaciens* AGL1 by electroporation using the GIBCO-BRL Cell-Porator. Transformed plasmids were confirmed by restriction digestion. The *Agrobacterium* harboring the plasmid constructs were cultured in YEP medium with 10 mg/l carbenicillin, 50 mg/l kanamycin and 50 mg/l hygromycin and incubated at 25° C. for 48 h. 1 ml of this small-scale culture was inoculated into 100 ml of AB liquid medium with the same selection antibiotics and incubated at 25° C. until the cultures reached to an OD595 of 0.8 to 0.9. The culture was centrifuged at 4000 rpm for 10 min. The bacterial pellet was suspended with AMM medium to a density of OD595 at 0.4. Twenty to 25 ml of this bacterial suspension was poured into 9 cm deep petri dishes and vigorously growing light-yellow friable embryogenic calluses (about 5 mm in size) were immersed for 30 min with occasional shaking. The excess bacterial suspension was removed from the calluses by placing them on a sterile pad of dry tissue paper. Subsequently, the inoculated calluses were cultured on 2N6-AS medium in sterile 9 cm deep petri dishes and incubated at 25° C. in the dark for 2-3 days.

Selection and Regeneration of Rice Transformants

Co-cultivated calluses were washed at least ten times with gentle shaking using 50-75 ml of sterile water, and dried by placing on sterile tissue paper. Callus pieces were transferred to NBO medium with 2 mg/l 2,4-D, 250 mg/l cefotaxime and 50 mg/l hygromycin in sterile petri dishes for selection. After 4 weeks of selection, hygromycin-resistant micro-calluses were selected as putative transgenic calluses, excised from the co-cultivated callus, transferred to fresh selection medium for further proliferation, and cultured for 3 weeks. Vigorously growing hygromycin resistant calluses were transferred to NBO medium with 1 mg/l BA, 2 mg/l NAA, 5 mg/l ABA and 50 mg/l hygromycin (pre-regeneration medium) and cultured at 25° C. in the dark for 3 weeks. White compact hygromycin resistant calluses from pre-regeneration medium were transferred to NBO medium with 2 mg/l BA, 1 mg/l IAA, 1 mg/l NAA, 1 mg/l kinetin and 50 mg/l hygromycin (regeneration medium) and cultured at 25° C. with a photo period of 14 hour light (25 µmol/m$^2$/s). After 3 weeks, the regenerated hygromycin resistant plantlets, including the attached calluses, were transferred to 100 ml MS medium with 50 mg/l hygromycin (plantlet medium) in Phytacon vessels for shoot growth and root elongation. Plantlets were cultured until they reached the top of the containers. Each cluster of plantlets was transferred to a single well in a 54 well plastic tray containing ½ MS solution. The plantlets were acclimatized for 7-10 days in a growth chamber in 90% relative humidity at 20° C. with a photo period of 14 h light (25 µmol/m$^2$/s). Later the plants were transferred to soil in pots.

The transgenic rice plants obtained from the calluses were designated T0 generation, seeds obtained from individual plants were germinated in the presence of hygromycin and surviving plants were designated T1 generation. Seeds from the T1 plants were again subjected to hygromycin selection and were designated T2 generation in the present study.

Results and Discussion

Quantitative real-time PCR analysis indicated that HOG1 is constitutively expressed in *Arabidopsis*, with relatively higher levels in the leaves and inflorescence stem as described in Example 1(c), suggesting that HOG1 may play a fundamental role in regulating plant development. Purified HOG1 showed high affinity binding to cytokinin molecules (zeatin, benzyladenine and isopentenyl adenine) as described in Example 1(a).

The dissociation constant (KD) for benzyladenine was 20.6 nM (FIG. 11), suggesting high affinity binding with the HOG1 protein.

Various HOG1 *Arabidopsis* OE lines showed a 5- to 8-fold increase (FIG. 8e) in HOG1 transcript levels, while the *Arabidopsis* AS lines showed a 6- to 10-fold suppression (FIG. 8e) when compared to the wild type. Transgene expression significantly affected plant development and exhibited consistent phenotypes in several independent transgenic lines. Phenotypes were recorded from 28 independent OE transgenic lines and 21 AS lines, indicating that the changes were caused by the introduced gene product. Compared to the wild type (WT), seed germination occurred 4 to 5 days earlier in the OE lines, and almost 5 days later in the AS lines (Table 5). However, significant growth retardation was noticeable soon after germination of the OE lines whereas the AS lines showed no retardation of shoot growth despite delayed seed germination.

The formation and expansion of new rosette leaves was delayed and limited throughout vegetative growth in the OE lines. Early onset of flowering was observed in OE plants with bolting at the 4 rosette leaf stage (FIG. 8a and Table 5), when compared to WT and AS lines, which had at least 8 and 14 leaves, respectively, at the time of bolting (FIG. 8b and Table 5).

TABLE 5

Seed germination, onset of flowering and senescence: Five independent lines were used for each observation. For each line, the data represent the mean from three independent replicates. The anti-sense lines showed late germination, late bolting and delayed senescence.

| Plant genotype | Seed germination (Number of days) | Onset of flowering/ Bolting (Number of rosette leaves) | Senescence (Number of days) |
|---|---|---|---|
| Wild-type (WT) *Arabidopsis* | | | |
| 1 | 8 | 8 | 40 |
| 2 | 7 | 8 | 40 |
| 3 | 8 | 8 | 38 |
| 4 | 9 | 7 | 40 |
| 5 | 8 | 8 | 40 |
| Mean | 8 | 8 | 40 |
| Antisense lines | | | |
| AS1 | 13 | 14 | 55 |
| AS8 | 12 | 15 | 53 |
| AS14 | 13 | 14 | 54 |

TABLE 5-continued

Seed germination, onset of flowering and senescence: Five independent lines were used for each observation. For each line, the data represent the mean from three independent replicates. The anti-sense lines showed late germination, late bolting and delayed senescence.

| Plant genotype | Seed germination (Number of days) | Onset of flowering/ Bolting (Number of rosette leaves) | Senescence (Number of days) |
|---|---|---|---|
| AS21 | 14 | 14 | 54 |
| AS19 | 13 | 15 | 53 |
| Mean | 13 | 14 | 54 |
| Overexpression lines | | | |
| OE1 | 4 | 4 | 30 |
| OE8 | 4 | 3 | 32 |
| OE12 | 4 | 3 | 30 |
| OE18 | 5 | 4 | 28 |
| OE14 | 4 | 4 | 30 |
| Mean | 4 | 4 | 30 |

After initiation of flowering, the OE lines did not show any further increase in leaf biomass and no axillary inflorescence branches were formed even after 30 days of growth when senescence set in for these lines (FIG. 8b). However, the AS lines showed profuse branching of inflorescence stems (FIG. 8b) and delayed senescence. The AS lines had the highest leaf area (2.9±0.1 cm$^2$ per leaf) and it was significantly lower in the OE lines (0.4±0.1 cm$^2$) and the WT (1.0±0.1 cm$^2$) (FIG. 8c and Table 7). The overall plant biomass, silique size and as a result, the number and weight of seeds per silique (FIG. 8c, 8d, 8f and Table 6) were reduced drastically in the OE lines, while they were significantly higher in the AS lines compared to WT (FIG. 8c, 8d, 8f). The OE lines senesced about 10 days earlier, while the AS lines senesced two weeks later than the WT (FIG. 8a, 8b and Table 6).

TABLE 6

Leaf area, seed weight and number of seeds per silique: The data represent the mean ± SD from three independent replicates. Five independent lines were used in each case. The anti-sense lines showed a three-fold increase in leaf biomass and a two-fold increase in seed yield compared to the wild type.

| Plant genotype | Leaf area (cm$^2$) | Seed weight per silique (mg) | Number of seeds per silique |
|---|---|---|---|
| Wild-type (WT) *Arabidopsis* | | | |
| 1 | 1.04 ± 0.02 | 1.13 ± 0.01 | 35 ± 0.01 |
| 2 | 1.01 ± 0.01 | 1.01 ± 0.02 | 30 ± 0.02 |
| 3 | 0.90 ± 0.02 | 0.90 ± 0.02 | 26 ± 0.01 |
| 4 | 1.07 ± 0.02 | 1.18 ± 0.01 | 32 ± 0.01 |
| 5 | 0.98 ± 0.01 | 1.10 ± 0.01 | 29 ± 0.01 |
| Mean ± SD | 1.00 ± 0.07 | 1.06 ± 0.11 | 30.40 ± 0.36 |
| Antisense lines | | | |
| AS1 | 2.86 ± 0.01 | 1.79 ± 0.01 | 54 ± 0.02 |
| AS8 | 3.12 ± 0.01 | 2.40 ± 0.02 | 63 ± 0.02 |
| AS14 | 3.01 ± 0.01 | 1.96 ± 0.01 | 59 ± 0.02 |
| AS21 | 2.79 ± 0.02 | 1.96 ± 0.01 | 57 ± 0.01 |
| AS19 | 2.99 ± 0.02 | 2.00 ± 0.02 | 60 ± 0.01 |
| Mean ± SD | 2.95 ± 0.13 | 2.02 ± 0.22 | 58.60 ± 0.37 |
| Overexpression lines | | | |
| OE1 | 0.33 ± 0.02 | 0.68 ± 0.02 | 15 ± 0.01 |
| OE8 | 0.40 ± 0.02 | 0.72 ± 0.01 | 17 ± 0.01 |
| OE12 | 0.49 ± 0.02 | 0.81 ± 0.01 | 19 ± 0.02 |
| OE18 | 0.33 ± 0.02 | 0.70 ± 0.02 | 14 ± 0.02 |

TABLE 6-continued

Leaf area, seed weight and number of seeds per silique: The data represent the mean ± SD from three independent replicates. Five independent lines were used in each case. The anti-sense lines showed a three-fold increase in leaf biomass and a two-fold increase in seed yield compared to the wild type.

| Plant genotype | Leaf area (cm$^2$) | Seed weight per silique (mg) | Number of seeds per silique |
|---|---|---|---|
| OE14 | 0.40 ± 0.01 | 0.83 ± 0.01 | 17 ± 0.02 |
| Mean ± SD | 0.39 ± 0.06 | 0.75 ± 0.07 | 16.40 ± 0.14 |

The endogenous cytokinin content was determined for three independent lines each of WT, OE and AS lines, because of the established link between branching and senescence with cytokinin levels in plants. Isopentenyl adenine was the predominant cytokinin and its concentration was reduced by about 60% in the OE lines compared to WT (FIG. 8f). This could be the main reason for the reduced plant stature and biomass in the OE lines seen in FIGS. 8b and 8a. In contrast, in the AS lines, the concentration of isopentenyl adenine was increased by over 60% compared to the WT, or about a four-fold increase over the OE lines (FIG. 8f). This led to the opposite phenotype, namely, profuse branching and significant gain of biomass.

The results from the present *Arabidopsis* work suggest that the genetic manipulation of HOG1 or its orthologs in crop species can provide a means for enhancing yield. Screening for HOG1 orthologs in several other species was carried out. cDNAs were successfully identified and obtained from rice, *Brassica alboglabra*, *chrysanthemum* and *amaranthus*. Full-length cDNA of OsCBP (*Oryza sativa* Cytokinin Binding Protein; Os11g0455500) was isolated from rice (*Oryza sativa* L. ssp. *japonica*, cultivar Nipponbare) by reverse transcription-PCR. The derived amino acid sequence of OsCBP (SEQ ID NO: 5) showed 90% sequence identity to HOG1 (SEQ ID NO: 1) and there appears to be only one copy of the gene in rice (FIG. 10). Due to the high sequence similarity between HOG1 (SEQ ID NO: 1) and OsCBP (SEQ ID NO: 5), transgenic rice lines were generated using HOG1 cDNA in order to test if the yield enhancing trait can be achieved in rice. By *Agrobacterium*-mediated transformation, several independent rice lines were obtained and confirmed to be transgenic by quantitative real-time PCR and genomic Southern blots at the T1 generation (FIGS. 9, 12d and 12e). The phenotypes in OE lines and AS lines at the T2 generation were consistently segregating with the transgene (segregating lines did not survive hygromycin selection). Germination of T3 seeds in the selection medium showed that several of the selected lines were homozygous for the transgene (data not shown). The expression analysis of OsCBP was carried out in OE and AS lines and the hybrid parent (WT) line. Over-expression lines showed (FIG. 9f) almost a 5-fold increase in the expression levels of HOG1 when compared to the endogenous OsCBP expression levels in the WT. Additionally, the expression of OsCBP was reduced by six folds in some of the OE lines (FIG. 9f), confirming these to be co-suppression lines. The phenomenon of co-suppression of genes is well known in plants. Therefore, the phenotypes observed are due to the function of the introduced gene and not any non-specific effects of transformation. The phenotypes of the transgenic plants were consistent with the results from *Arabidopsis*.

In OE lines, there was no significant change in the number of tillers per plant when compared to the WT (Table 8), but many of the OE lines were significantly reduced in height and overall biomass gain (FIG. 9a, 9b, 9c and Table 8). The rice OE lines showed early flowering when compared to the WT by 7-10 days. In contrast, the AS lines showed up to a 6-fold reduction in the expression levels of endogenous OsCBP and exhibited a significant increase in the number of tillers per plant compared to the hybrid parent line (FIGS. 9b, 9c and 12b). The WT had 7 to 9 tillers, while the AS lines showed between 18 to 28 tillers per plant (Table 8). The phenotypes of the co-suppression lines were the same as those of the AS lines (FIGS. 9c, 9e, 12a, 12b and Table 8). Additionally, the co-suppression and AS lines showed branching from the above-ground nodes of the major tillers (FIG. 12d), leading to a significant overall increase in the number of panicles per plant (Table 8). The average number of seeds and plant biomass increased by 2- to over 3-folds in the AS and co-suppression lines when compared to the WT (Table 8). There were no other major changes in phenotypes of the AS and co-suppression lines compared to the WT plants. The maximum increase in grain yield per plant was over two folds (ranging from 1.5- to 2.7-fold) higher than that of the WT under the greenhouse growth conditions. Generally, the yield data from greenhouse growth conditions for rice were lower than that from ideal field conditions. Therefore, it is clear that if the strategy described here is used, it can lead to a significant increase in yield under field conditions.

TABLE 7

Pearson's Correlation coefficient (r) of the parameters contributing to biomass and seed yield: Correlation coefficient was tested between: Leaf area ($cm^2$) × Seed weight (mg) per silique (A); Leaf area ($cm^2$) × Number of seeds per silique (B); and Seed weight per silique (mg) × Number of seeds per silique (C). After the correlation analysis, Student's t-test was performed. The t-test values are given in brackets. The 'r' values show positive correlation in all the tests. Based on this, it can be predicted that anti-sense suppression of HOG1 leads to an increase in the key parameters contributing towards leaf biomass and seed yield.

| Plant genotype | A | B | C |
| --- | --- | --- | --- |
| Wild type | 0.898 (t = 2.043) | 0.857 (t = 2.755) | 0.795 (t = 3.84) |
| HOG1 antisense lines | 0.763 (t = 2.043) | 0.847 (t = 2.755) | 0.912 (t = 3.84) |
| HOG1 overexpression lines | 0.769 (t = 2.078) | 0.979 (t = 2.878) | 0.767 (t = 2.269) |

TABLE 8

Quantification of yield parameters in the T2 generation transgenic rice plants harboring full length Arabidopsis HOG1 cDNA in sense (over-expression and co-suppression) or anti-sense orientation (driven by rice ubiquitin promoter) leading to manipulation of the expression of endogenous OsCBP gene.

| Genotype | Tillers/ plant | Panicles/ plant | Leaf area ($cm^2$) | Fresh Weight/ plant (g) | Seeds/ plant |
| --- | --- | --- | --- | --- | --- |
| Wild type (*Oryza sativa* ssp. *japonica* cv Nipponbare) | | | | | |
| Plant #1 | 7 | 8 | 28 | 25 | 139 |
| Plant #3 | 9 | 9 | | | 143 |
| Plant #4 | 9 | 9 | | | 139 |
| Mean ± SD | 8.3 ± 1.0 | 8.6 ± 0.5 | — | — | 140 ± 2 |
| Antisense lines | | | | | |
| Line # 1S-2 High | | | | | |
| Plant #3 | 19 | 21 | 32 | 85 | 278 |
| Plant #12 | 26 | 24 | | | 151 |
| Plant #15 | 20 | 31 | | | 155 |
| Mean ± SD | 21.6 ± 4.0 | 25.0 ± 5.0 | — | — | 194 ± 72 |
| Medium | | | | | |
| Plant #1 | 18 | 36 | | | 378 |
| Plant #5 | 14 | 28 | | | 253 |
| Plant #9 | 15 | 31 | | | 155 |
| Mean ± SD | 15.6 ± 2.0 | 31.6 ± 4.0 | nd | nd | 262 ± 112 |
| Low | | | | | |
| Plant #6 | 11 | 29 | | | 191 |
| Plant #8 | 11 | 22 | | | 251 |
| Plant #10 | 9 | 16 | | | 127 |
| Mean ± SD | 10.3 ± 1.0 | 22.3 ± 6.5 | nd | nd | 189.6 ± 62 |
| Line # 1S-3 High | | | | | |
| Plant #1 | 21 | 32 | | | 158 |
| Plant #12 | 23 | 37 | 35 | 89 | 200 |
| Plant #13 | 28 | 40 | | | 203 |
| Mean ± SD | 24 ± 3.6 | 36.3 ± 4.0 | — | — | 187 ± 25 |
| Medium | | | | | |
| Plant #9 | 17 | 28 | | | 156 |
| Plant #10 | 18 | 25 | | | 178 |
| Plant #15 | 18 | 23 | | | 258 |
| Mean ± SD | 17.6 ± 0.5 | 25.3 ± 2.5 | nd | nd | 197 ± 54 |
| Low | | | | | |
| Plant #2 | 14 | 20 | | | 209 |
| Plant #3 | 15 | 20 | | | 114 |
| Plant #14 | 14 | 25 | | | 56 |
| Mean ± SD | 14.3 ± 0.5 | 21.6 ± 3.0 | nd | nd | 126 ± 77 |
| Over expression Lines | | | | | |
| Line # 6-3 | | | | | |
| Plant #5 | 19 | 25 | | | 0 |
| Plant #6 | 13 | 9 | 7 | 20 | 0 |
| Plant # 10 | 18 | 21 | | | 0 |
| Mean ± SD | 16.6 ± 3.2 | 18.3 ± 8.3 | — | — | 0 |
| Line # 3T1 | | | | | |
| Plant # 1 | 14 | 15 | | | 22 |
| Plant #2 | 16 | 24 | | | 32 |
| Plant #3 | 16 | 19 | | | 0 |
| Mean ± SD | 15.3 ± 1.0 | 19.3 ± 4.5 | nd | nd | 18 ± 16 |
| Co suppression Lines | | | | | |
| Line #1-3 High | | | | | |
| Plant #2 | 19 | 27 | 40 | 90 | 370 |
| Medium | | | | | |
| Plant #1 | 15 | 23 | | | 256 |
| Plant #4 | 14 | 32 | | | 184 |
| Plant #5 | 14 | 26 | | | 190 |
| Mean ± SD | 14.3 ± 0.5 | 27 ± 4.5 | nd | nd | 210 ± 40 |

TABLE 8-continued

Quantification of yield parameters in the T2 generation transgenic rice plants harboring full length Arabidopsis HOG1 cDNA in sense (over-expression and co-suppression) or anti-sense orientation (driven by rice ubiquitin promoter) leading to manipulation of the expression of endogenous OsCBP gene.

| Genotype | Tillers/ plant | Panicles/ plant | Leaf area (cm²) | Fresh Weight/ plant (g) | Seeds/ plant |
|---|---|---|---|---|---|
| Low | | | | | |
| Plant #8 | 10 | 17 | | | 281 |
| Plant #6 | 12 | 25 | | | 171 |
| Plant #3 | 18 | 29 | | | 64 |
| Mean ± SD | 15 ± 4.2 | 23.6 ± 6.0 | nd | nd | 172 ± 109 |
| Line #4T-3 | | | | | |
| High | | | | | |
| Plant #1 | 15 | 22 | | | 153 |
| Plant #4 | 18 | 25 | 39 | 89 | 147 |
| Mean ± SD | 16.5 ± 2.0 | 23.5 ± 2.0 | — | — | 150 ± 4 |
| Medium | | | | | |
| Plant #5 | 17 | 23 | | | 113 |
| Plant #3 | 13 | 20 | | | 130 |
| Mean ± SD | 15.0 ± 3.0 | 21.5 ± 2.0 | nd | nd | 122 ± 12 |
| Low | | | | | |
| Plant #2 | 12 | 23 | nd | nd | 131 |

The plants were grouped as 'High', 'Medium' and 'Low' within each transgenic line based on the number of tillers per plant. The total number of tillers, panicles and seeds per plant are presented as mean ± SD. Only the fully filled grains in each plant were counted. The leaf area values represent the area of a single leaf. The fully expanded second leaf of the second tiller of each plant was measured as an indicative parameter. Fresh weight determination was for the whole uprooted plant and only selected plants were measured for the different lines.

The present results from *Arabidopsis* and rice suggest that orthologs of HOG1 can be used for improvement of a variety of crop plants. The number of tillers per plant is a key factor that determines yield in the major cereal crops. Therefore, using this approach, there is a potential for increasing the yield of major cereal crops like rice, wheat, maize and barley.

Increase in biomass is also a highly desirable feature for plants used for cellulosic ethanol production and leafy vegetables as well as fodder crops. Additionally, over-expressing HOG1 or its orthologs in ornamental species may help to induce dwarfing and early flowering.

Applications

The present inventors have identified a method that has the potential to modulate traits in plants, using the isolated polynucleotide of SEQ ID NO: 2. The methods disclosed herein are able to enhance agricultural productivity and grain yield per unit area under cultivation. The methods disclosed herein are useful for enhancing biomass production in fodder grass, and increasing branching in leafy vegetables and foliage plants. The isolated polynucleotides disclosed herein can be administered to both monocotyledonous and dicotyledonous plants to produce plants with modulated traits useful for crop improvement and other commercial and scientific uses.

In particular, production of biomass is a growing industry as interest in sustainable fuel sources is growing. Without being bound by theory, it is speculated that the abundance of biomass produced by the methods disclosed herein can be converted into biofuel such as woodgas, bio-methanol or bio-ethanol fuel. For example, alcohol can be produced from cellulosic material by known hydrolysis, fermentation and distillation methods. Therefore, the use of biomass fuel is seen as a renewable energy source considered by some as a means of reducing greenhouse gas emissions and providing an alternative to fossil fuels.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of modulating the expression of at least one trait in a rice plant, the method comprising:
  decreasing the expression of a polypeptide in a rice plant, wherein the polypeptide comprises the amino acid sequence of SEQ ID NO: 5, wherein decreasing the expression of the polypeptide comprises
  introducing into one or more cells of the rice plant a polynucleotide which decreases the expression of the polypeptide to produce a transformed rice plant, wherein the introduced polynucleotide is selected from the group consisting of:
  i) an antisense polynucleotide which comprises the nucleic acid sequence of SEQ ID NO: 15, and
  ii) an antisense polynucleotide which consists of the nucleic acid sequence of SEQ ID NO: 15; and
  selecting for decreased expression of the polypeptide and for modulated expression of at least one trait in the rice plant,
  wherein the modulated expression of at least one trait in the rice plant is selected from the group consisting of increased number of panicles, increased seed yield, increased plant biomass, increased number of tillers, and increased leaf area, relative to the expression of the same trait in a non-transformed rice plant.

2. The method according to claim 1, wherein the increased number of panicles is up to 5-fold, the increased number of seeds per plant is up to 2.7-fold, the increase in plant biomass is up to 3.6-fold, the increased number of tillers is up to 4-fold, and the increased leaf area is up to 1.25 fold, relative to a non-transformed rice plant.

3. A method of producing a transgenic rice plant with at least one modulated trait comprising:
  transforming a rice plant, rice plant part or rice plant cell with a polynucleotide comprising
  i) an antisense polynucleotide which comprises the nucleic acid sequence of SEQ ID NO: 15, or
  ii) an antisense polynucleotide which consists of the nucleic acid sequence of SEQ ID NO: 15;
  growing the transformed rice plant, rice plant part or rice plant cell to produce a transgenic rice plant; and
  selecting the transgenic rice plant for at least one trait selected from the group consisting of increased plant biomass, increased number of panicles, increased leaf area, increased seed yield, and increased tiller number, relative to the same trait in a non-transformed rice plant.

4. The method according to claim 3, wherein the growing comprises culturing the transformed rice plant, rice plant part or rice plant cell under conditions which permit growth of the transformed rice plant, rice plant part or rice plant cell.

5. The method according to claim 3, wherein the rice plant part is selected from the group consisting of root, stem, leaf, bud, flower, shoot, seed and branch.

6. The method of claim 3, wherein said transgenic plant is capable of producing fertile plants.

7. A method of producing a rice plant with increased biomass, the method comprising
  transforming a rice plant with an isolated polynucleotide selected from the group consisting of:
  i) an antisense polynucleotide comprising the nucleic acid sequence of SEQ ID NO: 15 and
  ii) an antisense polynucleotide which consists of the nucleic acid sequence of SEQ ID NO: 15; and
  selecting the transformed plant for the expression of said polynucleotide and increased biomass.

8. The method of claim 3, wherein the antisense polynucleotide decreases expression of a rice polypeptide comprising the amino acid of SEQ ID NO: 5.

* * * * *

SEQUENCE LISTING

```
<160> NUMBER OF SEQ ID NOS: 30

<210> SEQ ID NO 1
<211> LENGTH: 485
<212> TYPE: PRT
<213> ORGANISM: Arabidopsis thaliana
<220> FEATURE:
<223> OTHER INFORMATION: HOG1 Arabidopsis thaliana

<400> SEQUENCE: 1

Met Ala Leu Ile Val Glu Lys Thr Ser Gly Gly Arg Glu Tyr Lys Val
1               5                   10                  15

Lys Asp Met Ser Gln Ala Asp Phe Gly Arg Leu Glu Leu Glu Leu Ala
            20                  25                  30

Glu Val Glu Met Pro Gly Leu Met Ala Cys Arg Thr Glu Phe Gly Pro
        35                  40                  45

Ala Gln Pro Phe Lys Gly Ala Arg Ile Thr Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
```

```
                       100                 105                 110
Thr Leu Gln Glu Tyr Trp Trp Cys Thr Glu Arg Ala Leu Asp Trp Gly
            115                 120                 125

Pro Gly Gly Gly Pro Asp Leu Ile Val Asp Asp Gly Gly Asp Ala Thr
        130                 135                 140

Leu Leu Ile His Glu Gly Val Lys Ala Glu Ile Phe Glu Lys Thr
145                 150                 155                 160

Gly Gln Val Pro Asp Pro Thr Ser Thr Asp Asn Pro Glu Phe Gln Ile
                165                 170                 175

Val Leu Ser Ile Ile Lys Glu Gly Leu Gln Val Asp Pro Lys Lys Tyr
            180                 185                 190

His Lys Met Lys Gly Arg Leu Val Gly Val Ser Glu Glu Thr Thr Thr
        195                 200                 205

Gly Val Lys Arg Leu Tyr Gln Met Gln Glu Ser Gly Ala Leu Leu Phe
    210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Val Ile Cys Gly Tyr Gly Asp
            260                 265                 270

Val Gly Lys Gly Cys Ala Ala Ala Met Lys Thr Ala Gly Ala Arg Val
        275                 280                 285

Ile Val Thr Glu Ile Asp Pro Ile Cys Ala Leu Gln Ala Met Met Glu
    290                 295                 300

Gly Leu Gln Val Leu Thr Leu Glu Asp Val Val Ser Glu Ala Asp Ile
305                 310                 315                 320

Phe Val Thr Thr Thr Gly Asn Lys Asp Ile Ile Met Val Asp His Met
                325                 330                 335

Arg Lys Met Lys Asn Asn Ala Ile Val Cys Asn Ile Gly His Phe Asp
            340                 345                 350

Asn Glu Ile Asp Met Gln Gly Leu Glu Thr Phe Pro Gly Val Lys Arg
        355                 360                 365

Ile Thr Ile Lys Pro Gln Thr Asp Arg Trp Val Phe Pro Asp Thr Lys
    370                 375                 380

Ser Gly Ile Ile Val Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Asn Glu Lys Ser Ser Gly Lys Tyr
            420                 425                 430

Glu Lys Lys Val Tyr Val Leu Pro Lys His Leu Asp Glu Lys Val Ala
        435                 440                 445

Ala Leu His Leu Gly Lys Leu Gly Ala Lys Leu Thr Lys Leu Thr Lys
    450                 455                 460

Asp Gln Ser Asp Tyr Val Ser Ile Pro Ile Glu Gly Pro Tyr Lys Pro
465                 470                 475                 480

Pro His Tyr Arg Tyr
                485

<210> SEQ ID NO 2
<211> LENGTH: 1775
<212> TYPE: DNA
<213> ORGANISM: Arabidopsis thaliana
```

<220> FEATURE:
<223> OTHER INFORMATION: HOG1 Arabidopsis thaliana cDNA

<400> SEQUENCE: 2

| | | | | | |
|---|---|---|---|---|---|
| ggccgcggga | attcgatttc | tacccccct | gccccaatct | tagatccgaa | aaaatggcgt | 60 |
| tgatcgttga | gaagacgtcg | ggtggccgtg | agtacaaggt | caaggacatg | tctcaggccg | 120 |
| acttcggtcg | tctcgagctc | gagctcgccg | aagttgagat | gccaggactc | atggcttgcc | 180 |
| gtaccgagtt | cggcccagct | cagcccttca | aggcgctag | aatcaccgga | tctctccaca | 240 |
| tgacgatcca | gaccgccgtc | ctcatcgaaa | ccctaaccgc | cctcggcgcg | aagtcagat | 300 |
| ggtgctcctg | caacatcttc | tcaacccaag | accacgccgc | cgccgcaatc | gcccgtgact | 360 |
| ccgccgccgt | tttcgcctgg | aaaggtgaga | cgcttcagga | gtactggtgg | tgcacggagc | 420 |
| gtgctctcga | ctgggcccca | ggtggtggtc | cagatctgat | cgtcgatgac | ggtggcgacg | 480 |
| ccacgctttt | gatccacgag | ggagtgaagg | ccgaggagat | ctttgagaag | acgggtcagg | 540 |
| ttcctgatcc | cacttccact | gacaaccctg | agttccagat | cgtgctttcg | atcatcaagg | 600 |
| aaggtctcca | ggttgatcct | aagaagtacc | acaagatgaa | ggggagactc | gtcggtgtct | 660 |
| ctgaggagac | caccaccggt | gtcaagaggc | tttaccagat | gcaggaaagt | ggagccttt | 720 |
| tgttcccagc | cattaacgtc | aacgactccg | tcaccaagag | caagttcgac | aacttgtacg | 780 |
| gttgccgtca | ctctctacct | gatggtctca | tgagggccac | tgatgtcatg | atcgccggaa | 840 |
| aggttgcggt | tatctgtggt | tatggtgatg | tcggtaaggg | ttgtgccgct | gccatgaaaa | 900 |
| ccgctggtgc | tagagtcatt | gtgaccgaga | tcgaccccat | ctgtgcccta | caagctatga | 960 |
| tggaagggct | tcaagttctg | accttgagg | atgtcgtctc | tgaagctgac | atctttgtca | 1020 |
| ccaccaccgg | taacaaagac | atcatcatgg | ttgaccacat | gaggaagatg | aagaacaacg | 1080 |
| ctatcgtctg | caacattggt | cactttgaca | acgagattga | catgcaagga | cttgagacct | 1140 |
| tccctggagt | gaagcgtatc | accatcaagc | cccagaccga | caggtgggtg | ttcccagaca | 1200 |
| ccaagtccgg | aatcattgtt | ttggccgagg | tcgtctcat | gaacttgggt | tgtgccactg | 1260 |
| gtcacccaag | tttcgtgatg | tcttgctctt | tcaccaacca | ggtgattgcc | cagcttgagc | 1320 |
| tttggaacga | gaagtcgagc | ggtaagtacg | agaagaaggt | gtacgttcta | cccaagcatt | 1380 |
| tggatgagaa | ggttgcggca | cttcacttgg | gcaagcttgg | agctaagctc | actaagctga | 1440 |
| caaaggacca | atctgactac | gtcagcattc | caattgaggg | accatacaag | cctcctcact | 1500 |
| acaggtactg | agagagagag | agagtcgaca | aagcggttca | ggttcggatc | tacttgtggt | 1560 |
| tttgtgttgg | gttgtggtgg | gagagtggaa | cagtttgaga | tattggtctt | ctgatgaagt | 1620 |
| tgaccaaata | tcagtattaa | taagggttat | tggcttttga | aggttgtgct | tggtttctcc | 1680 |
| attttcatg | aaacttaaat | tagtttttgg | tttagtttcc | ctcttgattt | tattttgtgt | 1740 |
| gttctgttta | gcgttgtact | cttcaaacaa | atgag | | | 1775 |

<210> SEQ ID NO 3
<211> LENGTH: 485
<212> TYPE: PRT
<213> ORGANISM: Nicotiana tabacum
<220> FEATURE:
<223> OTHER INFORMATION: Nicotiana tabacum, cv. Xanthi homolog (amino acid sequence)

<400> SEQUENCE: 3

Met Ala Leu Leu Val Glu Lys Thr Thr Ser Gly Arg Glu Tyr Lys Val
1               5                   10                  15

```
Lys Asp Met Ser Gln Ala Asp Phe Gly Arg Leu Glu Ile Glu Leu Ala
            20                  25                  30

Glu Val Glu Met Pro Gly Leu Met Ala Cys Arg Thr Glu Phe Gly Pro
        35                  40                  45

Ser Gln Pro Phe Lys Gly Ala Lys Ile Thr Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Gln Glu Tyr Trp Trp Cys Thr Glu Arg Ala Leu Asp Trp Gly
        115                 120                 125

Pro Gly Gly Pro Asp Leu Ile Val Asp Asp Gly Gly Asp Ala Thr
    130                 135                 140

Leu Leu Ile His Glu Gly Val Lys Ala Glu Glu Phe Ala Lys Asn
145                 150                 155                 160

Gly Thr Ile Pro Asp Pro Asn Ser Thr Asp Asn Ala Glu Phe Gln Leu
                165                 170                 175

Val Leu Thr Ile Ile Lys Glu Ser Leu Lys Thr Asp Pro Leu Lys Tyr
            180                 185                 190

Thr Lys Met Lys Glu Arg Leu Val Gly Val Ser Glu Glu Thr Thr Thr
        195                 200                 205

Gly Val Lys Arg Leu Tyr Gln Met Gln Ala Asn Gly Thr Leu Leu Phe
    210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Leu Val Ala Gly Tyr Gly Asp
            260                 265                 270

Val Gly Lys Gly Cys Ala Ala Ala Leu Lys Gln Ala Gly Ala Arg Val
        275                 280                 285

Ile Val Thr Glu Ile Asp Pro Ile Cys Ala Leu Gln Ala Thr Met Glu
    290                 295                 300

Gly Leu Gln Val Leu Thr Leu Glu Asp Val Val Ser Asp Val Asp Ile
305                 310                 315                 320

Phe Val Thr Thr Thr Gly Asn Lys Asp Ile Ile Met Val Asp His Met
                325                 330                 335

Arg Lys Met Lys Asn Asn Ala Ile Val Cys Asn Ile Gly His Phe Asp
            340                 345                 350

Asn Glu Ile Asp Met Leu Gly Leu Glu Thr Tyr Pro Gly Val Lys Arg
        355                 360                 365

Ile Thr Ile Lys Pro Gln Thr Asp Arg Trp Val Phe Pro Asp Thr Asn
    370                 375                 380

Ser Gly Ile Ile Val Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Asn Glu Lys Ser Ser Gly Lys Tyr
            420                 425                 430

Glu Lys Lys Val Tyr Val Leu Pro Lys His Leu Asp Glu Lys Val Ala
```

```
           435                 440                 445
Ala Leu His Leu Gly Lys Leu Gly Ala Lys Leu Thr Lys Leu Ser Lys
    450                 455                 460

Asp Gln Ala Asp Tyr Ile Ser Val Pro Val Glu Gly Pro Tyr Lys Pro
465                 470                 475                 480

Ala His Tyr Arg Tyr
            485

<210> SEQ ID NO 4
<211> LENGTH: 1812
<212> TYPE: DNA
<213> ORGANISM: Nicotiana tabacum
<220> FEATURE:
<223> OTHER INFORMATION: Nicotiana tabacum, cv. Xanthi homolog
      (nucleotide sequence)

<400> SEQUENCE: 4
gaagagaaaa aagcctctca aatctcatct ctaaccaccc aatttctcat actcgctcta      60
cccatggctc tattagtcga gaagaccacc tctggccgcg agtacaaggt caaggacatg     120
tctcaggccg atttcggccg gcttgaaatc gagctggccg aagttgaaat gcctggtctc     180
atggcttgtc gtactgaatt tggcccttca cagccattta aggtgctaa  gattactgga     240 tctttacata tgaccattca aactgcagtt ttgattgaaa cccttactgc tttgggtgct     300
gaagttagat ggtgttcttg caacatcttc tccactcaag atcacgccgc tgctgccatt     360
gcacgtgaca gcgccgccgt gttcgcgtgg aagggtgaga ctctgcagga gtattggtgg     420
tgtactgaga gggcacttga ctggggtcca ggtggtgggc ccgacttgat cgtcgacgat     480
ggtggtgatg ctacactctt gattcatgag ggtgttaagg cagaagaaga gtttgctaag     540
aatgggacaa tcccagatcc taactctacc gataatgctg agtttcagct tgtacttact     600
attattaagg aaagtttgaa gactgatcct ttaaaatata ccaagatgaa ggaaagactc     660
gtcggtgttt ctgaggaaac taccactgga gttaagaggc tttatcagat gcaggctaat     720
ggaactttgc ttttccctgc tattaatgtt aatgattctg ttaccaagag caagttcgac     780
aacttgtacg gatgccgcca ctcactgccc gatggtctca tgagggctac tgatgttatg     840
attgccggaa aggttgccct tgttgctggt tatggagatg tcggcaaggg ttgtgctgct     900
gccttgaaac aagccggtgc ccgtgtgatt gtgaccgaga ttgaccctat ctgtgctctc     960
caggctacca tggaaggcct ccaggtcctt actctagagg atgtcgtttc tgatgttgat    1020
atctttgtca ccacgaccgg taacaaggac attatcatgg ttgaccacat gaggaagatg    1080
aagaacaatg ccattgtttg caacattggt cactttgaca cgaaatcga  catgcttggt    1140 ctcgagacct accctggtgt caagaggatc acaattaagc ctcaaaccga cagatgggtc    1200
ttccctgaca ccaacagtgg catcattgtc ttggctgagg gtcgtctcat gaacttggga    1260
tgtgccacag acaccctag  ttttgtgatg tcgtgctcgt tcactaacca agtcattgcc    1320
caactcgagt tgtggaatga aaagagcagt gggaagtatg agaagaaagt gtatgtcttg    1380
ccaaaacacc tcgacgagaa ggttgctgca cttcatctcg gaaagctcgg agccaagctt    1440
accaaacttt cgaaggatca agctgactac attagcgttc cagttgaggg tccttacaag    1500
cctgctcact acaggtactg agcgaaaaca aatcgacaga ggagaacagc attgtcgcgg    1560
catgattgtt ttgcatttaa tactttgatt ttgtttagga tactagtatt ttgaatattg    1620
gtggtgatat atttgggagg aagtggcatg ttttgctgga aaagaaatgg gtcttatttg    1680
aaagtaagac caaaatgtgt tgaataagat tatggttggt ggtgtgatat gatattgtag    1740
```

```
taagttagaa ccatttgctt tttggtgtat ggttttttgtt tcaagaaatc aaagcaacac    1800 tttaccttt tc                                                         1812
```

<210> SEQ ID NO 5
<211> LENGTH: 485
<212> TYPE: PRT
<213> ORGANISM: Oryza sativa
<220> FEATURE:
<223> OTHER INFORMATION: Oryza sativa homolog (amino acid sequence),
      OsCBP

<400> SEQUENCE: 5

```
Met Ala Leu Ser Val Glu Lys Thr Ser Ser Gly Arg Glu Tyr Lys Val
1               5                   10                  15

Lys Asp Leu Ser Gln Ala Asp Phe Gly Arg Leu Glu Ile Glu Leu Ala
            20                  25                  30

Glu Val Glu Met Pro Gly Leu Met Ala Cys Arg Ala Glu Phe Gly Pro
        35                  40                  45

Ser Gln Pro Phe Lys Gly Ala Arg Ile Ser Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Glu Glu Tyr Trp Trp Cys Thr Glu Arg Cys Leu Asp Trp Gly
        115                 120                 125

Val Gly Gly Gly Pro Asp Leu Ile Val Asp Asp Gly Gly Asp Ala Thr
    130                 135                 140

Leu Leu Ile His Glu Gly Val Lys Ala Glu Glu Phe Glu Lys Ser
145                 150                 155                 160

Gly Lys Val Pro Asp Pro Glu Ser Thr Asp Asn Ala Glu Phe Lys Ile
                165                 170                 175

Val Leu Thr Ile Ile Arg Asp Gly Leu Lys Ser Asp Pro Ser Lys Tyr
            180                 185                 190

Arg Lys Met Lys Glu Arg Leu Val Gly Val Ser Glu Glu Thr Thr Thr
        195                 200                 205

Gly Val Lys Arg Leu Tyr Gln Met Gln Glu Thr Gly Ala Leu Leu Phe
    210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Val Cys Gly Tyr Gly Asp
            260                 265                 270

Val Gly Lys Gly Cys Ala Ala Ala Leu Lys Gln Ala Gly Ala Arg Val
        275                 280                 285

Ile Val Thr Glu Ile Asp Pro Ile Cys Ala Leu Gln Ala Leu Met Glu
    290                 295                 300

Gly Leu Gln Val Leu Thr Leu Glu Asp Val Val Ser Glu Ala Asp Ile
305                 310                 315                 320

Phe Val Thr Thr Thr Gly Asn Lys Asp Ile Ile Met Val Asp His Met
                325                 330                 335
```

| | | | | | | | | | | | | |
|---|---|---|---|---|---|---|---|---|---|---|---|---|
|Arg|Lys|Met|Lys|Asn|Ala|Ile|Val|Cys|Asn|Ile|Gly|His|Phe|Asp|
| | |340| | | |345| | | |350| | |

Asn Glu Ile Asp Met Leu Gly Leu Glu Thr Tyr Pro Gly Val Lys Arg
            355                 360                 365

Ile Thr Ile Lys Pro Gln Thr Asp Arg Trp Val Phe Pro Glu Thr Asn
        370                 375                 380

Thr Gly Ile Ile Val Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Lys Glu Lys Ser Thr Gly Lys Tyr
            420                 425                 430

Glu Lys Lys Val Tyr Val Leu Pro Lys His Leu Asp Glu Lys Val Ala
            435                 440                 445

Ala Leu His Leu Gly Lys Gly Ala Arg Leu Thr Lys Leu Ser Lys
            450                 455                 460

Ser Gln Ala Asp Tyr Ile Ser Val Pro Val Glu Gly Pro Tyr Lys Pro
465                 470                 475                 480

Ala His Tyr Arg Tyr
            485

<210> SEQ ID NO 6
<211> LENGTH: 1458
<212> TYPE: DNA
<213> ORGANISM: Oryza sativa
<220> FEATURE:
<223> OTHER INFORMATION: Oryza sativa homolog (nucleotide sequence),
      OsCPB

<400> SEQUENCE: 6
atggcgctct ccgtggagaa gacctcgtcg gggagggagt acaaggtgaa ggacctctcc      60
caggcggact tcggccgcct cgagatcgag ctcgccgagg tcgagatgcc ggggctcatg     120
gcgtgccgcg ccgagttcgg ccccctcccag ccgttcaagg gcgcccggat ctccgggtcc    180
ctccacatga ccatccagac cgccgtcctc atcgagaccc tcaccgccct ggcgccgag     240 gtccgctggt gctcctgcaa catcttctcc acgcaggacc acgccgccgc cgccatcgcc    300
agggactccg ccgccgtgtt cgcctggaag gggagaccc tcgaggagta ctggtggtgc     360
accgagcgct gcctcgactg gggcgtcggc ggcggcccg acctcatcgt cgacgacggc    420
ggcgacgcca gctgctcat ccacgagggc gtcaaggccg aggaggagtt cgagaagtca   480
ggcaaggtcc ccgaccccga gtccaccgac aacgccgagt tcaagatcgt gctcaccatc    540
atccgcgacg cctcaagtc cgaccccagc aagtaccgca agatgaagga gaggctcgtc    600
ggagtctccg aggagaccac caccggtgtc aagaggctct accagatgca ggagaccggc    660
gccctcctct ccccgccat caacgtcaac gactccgtca ccaagagcaa gtttgacaac     720
ctgtatggtt gccgccactc tctccctgat ggtctcatga gggctaccga tgttatgatc    780
gctggcaagg ttgccgtggt ctgcggttat ggtgatgttg caagggctg tgctgctgct    840 ctcaagcagg ctggtgcccg tgtcattgtt actgagattg accccatctg tgccctccag    900
gcccttatgg agggtctcca ggtcctcacc ttggaggatg ttgtctcgga ggctgacatc    960
tttgtgacca ccactggcaa caaggacatc ataatggttg accacatgag gaagatgaag    1020
aacaatgcca tcgtttgcaa cattggtcac tttgacaatg agattgacat gctcggcctt    1080
gagacctacc ctggtgtcaa gcgcatcacc atcaagcctc agaccgaccg ctgggtcttc    1140

-continued

```
cctgagacca acactggcat cattgtcctt gctgagggtc gtctcatgaa ccttgggtgc    1200
gctactggcc accccagttt tgtcatgtcc tgctcattca ctaaccaggt cattgctcag    1260
cttgagctgt ggaaggagaa gagcactggc aagtacgaga agaaggtgta cgttcttccc    1320
aagcacctcg acgagaaggt ggccgccctc cacttgggca agcttggtgc caggctgacc    1380
aagctctcca gtcgcaggc tgactacatc agcgttccag ttgagggtcc ctacaagccc    1440
gcgcactacc ggtactag                                                  1458
```

<210> SEQ ID NO 7
<211> LENGTH: 485
<212> TYPE: PRT
<213> ORGANISM: Triticum aestivum
<220> FEATURE:
<223> OTHER INFORMATION: Triticum aestivum homolog (amino acid sequence)

<400> SEQUENCE: 7

| Met | Ala | Leu | Ser | Val | Glu | Lys | Thr | Ser | Ser | Gly | Arg | Glu | Tyr | Lys | Val |
|---|---|---|---|---|---|---|---|---|---|---|---|---|---|---|---|
| 1 | | | | 5 | | | | | 10 | | | | | 15 | |

Lys Asp Leu Phe Gln Ala Asp Phe Gly Arg Leu Glu Leu Glu Leu Ala
            20                  25                  30

Glu Val Glu Met Pro Gly Leu Met Ala Cys Arg Thr Glu Phe Gly Pro
        35                  40                  45

Ser Gln Pro Phe Lys Gly Ala Arg Ile Ser Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Ser Gln Asp His Ala Ala
                85                  90                  95

Ala Ala Ile Ala Arg Asp Ser Ala Ala Val Phe Ala Trp Lys Gly Glu
            100                 105                 110

Thr Leu Glu Glu Tyr Trp Trp Cys Thr Glu Arg Cys Leu Asp Trp Gly
        115                 120                 125

Val Gly Gly Gly Pro Asp Leu Ile Val Asp Asp Gly Gly Asp Ala Thr
    130                 135                 140

Leu Leu Ile His Glu Gly Val Lys Ala Glu Glu Phe Glu Lys Ser
145                 150                 155                 160

Gly Lys Val Pro Asp Pro Glu Ser Thr Asp Asn Pro Glu Phe Lys Ile
                165                 170                 175

Val Leu Thr Ile Ile Arg Asp Gly Leu Lys Thr Asp Ala Ser Lys Tyr
            180                 185                 190

Arg Lys Met Lys Glu Arg Leu Val Gly Val Ser Glu Glu Thr Thr Thr
        195                 200                 205

Gly Val Lys Arg Leu Tyr Gln Met Gln Glu Ser Gly Thr Leu Leu Phe
    210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Val Cys Gly Tyr Gly Asp
            260                 265                 270

Val Gly Lys Gly Cys Ala Ala Ala Leu Lys Gln Ala Gly Ala Arg Val
        275                 280                 285

Ile Val Thr Glu Ile Asp Pro Ile Cys Ala Leu Gln Ala Leu Met Glu
    290                 295                 300

```
Gly Ile Gln Ile Leu Thr Leu Glu Asp Val Ser Glu Ala Asp Ile
305                 310                 315                 320

Phe Val Thr Thr Thr Gly Asn Lys Asp Ile Ile Met Val Asp His Met
                325                 330                 335

Arg Lys Met Lys Asn Asn Ala Ile Val Cys Asn Ile Gly His Phe Asp
                340                 345                 350

Asn Glu Ile Asp Met Asn Gly Leu Glu Thr Tyr Pro Gly Val Lys Arg
            355                 360                 365

Ile Thr Ile Lys Pro Gln Thr Asp Arg Trp Val Phe Pro Glu Thr Lys
        370                 375                 380

Thr Gly Ile Ile Val Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Asn Glu Lys Ala Ser Gly Lys Tyr
            420                 425                 430

Glu Lys Lys Val Tyr Val Leu Pro Lys His Leu Asp Glu Lys Val Ala
        435                 440                 445

Ala Leu His Leu Gly Lys Leu Gly Ala Arg Leu Thr Lys Leu Thr Lys
    450                 455                 460

Ser Gln Ser Asp Tyr Ile Ser Ile Pro Ile Glu Gly Pro Tyr Lys Leu
465                 470                 475                 480

Arg Leu Tyr Arg Tyr
                485

<210> SEQ ID NO 8
<211> LENGTH: 1708
<212> TYPE: DNA
<213> ORGANISM: Triticum aestivum
<220> FEATURE:
<223> OTHER INFORMATION: Triticum aestivum homolog (nucleotide sequence)

<400> SEQUENCE: 8
aatccaccaa ccttctccat ggcgctctcc gtggagaaga cctcgtcggg ccgggagtac      60
aaggtcaagg acctcttcca ggccgacttc ggccgcctcg agctcgagct cgccgaggtc     120
gagatgcccg gcctcatggc ctgccgcacc gagttcggcc cctcgcagcc cttcaagggc     180
gcccggatct ccggctccct ccacatgacc atccagaccg ccgtcctcat cgagaccctc     240
accgccctcg gcgccgaggt ccgctggtgc tcctgcaaca tcttctccag ccaggaccac     300
gccgccgccg ccatcgcccg cgactccgcg ccgtcttcg cctggaaggg cgagaccctc     360
gaggagtact ggtggtgcac cgagcgctgc ctcgactggg gcgtcggcgg cggccccgac     420
ctcatcgtcg acgacggcgg tgacgccacg ctgctcatcc acgagggcgt caaggccgag     480
gaggagttcg agaaatccgg caaggttccc gacccggagt ccaccgacaa ccccgagttc     540
aagatcgtcc tcaccatcat ccgcgacggg ctcaagaccg acgccagcaa gtaccgcaag     600
atgaaggaga ggctcgtcgg tgtctccgag agaccacca ccggcgtcaa gaggctctac     660
cagatgcagg agtccggcac cctcctcttc cccgccatca cgtcaacga ctccgtcacc     720 aagagcaagt tgacaacct ttacggttgc cgtcactcgc tccctgatgg tcttatgagg     780
gccactgatg ttatgatcgc cggcaaggtc gccgtggtct gcggttacgg tgatgttggc     840
aagggctgtg ccgccgcact caagcaggct ggtgcccgtg tgatcgtgac agagattgac     900
cccatctgtg cccttcaggc cctgatggag ggtatccaga tcctcacctt ggaggatgtt     960
gtctctgagg ctgacatctt tgtgaccacc accggaaaca aggacatcat catggtcgac    1020
```

-continued

```
cacatgagga agatgaagaa caacgccatt gtctgcaaca ttggtcactt tgacaatgag   1080
atcgacatga acggccttga gacctaccct ggtgtcaagc gcatcaccat caagccccag   1140
actgaccgtt gggtcttccc cgagaccaag actggcatca ttgttcttgc tgagggtcgt   1200
ctgatgaacc ttggatgtgc cactggccac cccagctttg tcatgtcctg ctcattcacc   1260
aaccaggtta ttgctcagct tgagttgtgg aacgagaagg ccagtggcaa gtatgagaag   1320
aaggtgtacg ttctccccaa gcacctcgac gagaaggtcg cggccctcca cttgggcaag   1380
ctcggcgcca ggctgaccaa gctcaccaag tcccagtctg actacattag catcccaatt   1440
gagggtcctt acaagctgcg gctttaccgg tactagtgtg tccagcatga ctagcggctg   1500
gcctgagcct gagtcggagc agcggcacca acgggaactc tatcaactat cctgtttccc   1560
ttctattatc ttacatgctg tctcttaggc ggaggatttg ttattatggt tatgttttga   1620
gccttgtgag ggttgggaga ggcggcgttt gcttttgccc agaaataatg gcattattat   1680
tggtttaagt gaggaggtgt gctttttcc                                      1708
```

<210> SEQ ID NO 9
<211> LENGTH: 485
<212> TYPE: PRT
<213> ORGANISM: Chrysanthemum indicum
<220> FEATURE:
<223> OTHER INFORMATION: Chrysanthemum homolog (amino acid sequence)

<400> SEQUENCE: 9

```
Met Ser Leu Thr Val Glu Lys Thr Thr Ser Gly Arg Glu Tyr Lys Val
1               5                   10                  15

Lys Asp Met Ser Leu Ala Asp Phe Gly Arg Leu Glu Leu Glu Leu Ala
                20                  25                  30

Glu Val Glu Met Pro Gly Leu Met Ser Cys Arg Thr Glu Phe Gly Pro
            35                  40                  45

Ser Gln Pro Phe Lys Gly Ala Arg Ile Thr Gly Ser Leu His Met Thr
        50                  55                  60

Ile Gln Thr Gly Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Gln Glu Tyr Trp Trp Cys Thr Glu Arg Ala Leu Asp Trp Gly
        115                 120                 125

Pro Gly Gly Gly Pro Asp Leu Ile Val Asp Asp Gly Gly Asp Ala Thr
    130                 135                 140

Leu Leu Ile His Glu Gly Val Lys Ala Glu Glu Phe Ala Lys Ser
145                 150                 155                 160

Gly Lys Leu Pro Asp Pro Thr Ser Thr Asp Asn Ala Glu Phe Gln Ile
                165                 170                 175

Val Leu Ser Ile Ile Lys Glu Gly Leu Ser Thr Asp Pro Leu Lys Tyr
            180                 185                 190

His Lys Met Lys Glu Arg Leu Val Gly Val Ser Glu Glu Thr Thr Thr
        195                 200                 205

Gly Val Lys Arg Leu Tyr Gln Met Gln Ala Asn Gly Thr Leu Leu Phe
    210                 215                 220

Pro Ala Ile Asn Val Asn Asp Ser Val Thr Lys Ser Lys Phe Asp Asn
225                 230                 235                 240
```

```
Leu Tyr Gly Cys Arg His Ser Leu Pro Asp Gly Leu Met Arg Ala Thr
                245                 250                 255

Asp Val Met Ile Ala Gly Lys Val Ala Val Val Cys Gly Tyr Gly Asp
            260                 265                 270

Val Gly Lys Gly Cys Ala Ser Ala Met Lys Gln Ala Gly Ala Arg Val
        275                 280                 285

Ile Val Thr Glu Ile Asp Pro Ile Cys Ala Leu Gln Ala Thr Met Glu
    290                 295                 300

Gly Leu Gln Val Leu Thr Leu Glu Asp Val Val Ser Glu Ala Asp Ile
305                 310                 315                 320

Phe Val Thr Thr Thr Gly Asn Lys Asp Ile Ile Met Val Asp Asp Met
                325                 330                 335

Arg Lys Met Lys Asn Asn Ala Ile Val Cys Asn Ile Gly His Phe Asp
            340                 345                 350

Asn Glu Ile Asp Met Leu Gly Leu Glu Thr Tyr Pro Gly Val Lys Arg
        355                 360                 365

Ile Thr Ile Lys Pro Gln Thr Asp Arg Trp Val Phe Pro Glu Thr Lys
    370                 375                 380

Ser Gly Val Ile Ile Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Asn Glu Lys Gly Thr Gly Lys Tyr
            420                 425                 430

Lys Lys Glu Val Tyr Val Leu Pro Lys His Leu Asp Glu Lys Val Ala
        435                 440                 445

Ala Leu His Leu Gly Lys Leu Gly Ala Lys Leu Thr Lys Leu Thr Lys
    450                 455                 460

Asp Gln Ser Asp Tyr Leu Ser Ile Pro Ile Glu Gly Pro Tyr Lys Pro
465                 470                 475                 480

Ala Ala Tyr Arg Tyr
                485

<210> SEQ ID NO 10
<211> LENGTH: 1535
<212> TYPE: DNA
<213> ORGANISM: Chrysanthemum indicum
<220> FEATURE:
<223> OTHER INFORMATION: Chrysanthemum homolog (nucleotide sequence)

<400> SEQUENCE: 10
gatcagatct caaaacccaa accttaaacc atgtctctta ctgtagagaa aaccacctct      60
ggccgtgaat acaaggtcaa ggacatgtcc ttggctgact cggccgtct cgaactcgag     120 ttagccgagg tcgagatgcc cgggcttatg tcctgcagga ccgaattcgg cccttctcag     180
ccttttaagg gagccagaat cactggatcc cttcacatga ccatccagac cggtgttctt     240
attgaaactt tgactgcttt gggtgctgag gttagatggt gctcttgcaa catcttttcg     300
acccaagacc atgctgctgc agccattgct cgtgactctg ctgcggtttt cgcctggaag     360
ggggagactc ttcaggagta ctggtggtgt actgagcgag cacttgactg ggtccaggt     420 ggtggtcctg atttgattgt ggatgatggt ggtgatgcta cgcttttgat ccatgaggga     480
gtgaaggccg aggaggagtt cgccaagagc ggtaaattgc ctgacccac ttccactgac     540 aatgctgagt ccagattgt gttgtcgatt attaaggaag gactttcgac cgacccattg     600
```

```
aagtaccaca agatgaagga aagactagtt ggtgtctctg aggaaaccac cactggtgtc    660
aagaggttgt accaaatgca agccaacggt actttgttgt tccctgccat caatgttaac    720
gattccgtca ccaagagcaa gtttgacaac ttgtatggat gccgtcactc actccctgat    780
ggtttgatga gagctactga tgtcatgatc gccggaaagg ttgcagtcgt ctgtggttac    840
ggagatgttg gaaagggttg tgcttcagcc atgaagcaag ctggtgctcg tgtcattgtg    900
acagaaattg atcccatctg tgctcttcag gctaccatgg aaggtctcca agtgctaact    960
ttggaagatg tcgtatccga agctgatatt tttgttacca ccaccggtaa caaggacatc   1020
atcatggttg atgacatgag gaagatgaag aacaatgcca tcgtctgcaa cattggtcac   1080
tttgacaatg aaatcgacat gcttggtctt gagacttacc ctggtgtcaa gagaatcacc   1140
atcaagcccc aaaccgacag gtgggtgttc cccgagacca agagtggcgt cattatcttg   1200
gctgagggta ggctcatgaa cttgggttgt gctactggtc accctagttt cgtgatgtct   1260
tgctctttca ctaaccaagt gattgctcaa cttgagttgt ggaatgagaa gggaaccggc   1320
aagtacaaga aggaggtgta tgtgttgccc aagcacttg acgagaaggt ggctgcactt    1380
catcttggaa agcttggagc caagctcact aagctcacca aggaccagtc tgactacctc   1440
agcattccta ttgaaggtcc ttacaagcct gctgcctaca ggtactgatc aaagaggata   1500
tctgctgttc agcaagactt tgaagaacct atggg                              1535
```

<210> SEQ ID NO 11
<211> LENGTH: 466
<212> TYPE: PRT
<213> ORGANISM: Brassica alboglabra
<220> FEATURE:
<223> OTHER INFORMATION: Brassica alboglabra homolog (amino acid sequence)

<400> SEQUENCE: 11

```
Met Ala Leu Ile Val Glu Lys Thr Ser Ser Gly Arg Glu Tyr Lys Val
1               5                   10                  15

Lys Asp Met Ser Gln Ala Asp Phe Gly Arg Leu Glu Leu Glu Leu Ala
            20                  25                  30

Glu Val Glu Met Pro Gly Leu Met Ala Cys Arg Thr Glu Phe Gly Pro
        35                  40                  45

Ala Gln Pro Phe Lys Gly Ala Arg Ile Thr Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Val Phe Ala Trp Lys Gly Glu
            100                 105                 110

Thr Leu Gln Glu Tyr Trp Trp Cys Thr Glu Arg Ala Leu Asp Trp Gly
        115                 120                 125

Pro Gly Gly Gly Pro Asp Leu Ile Val Asp Asp Gly Gly Asp Ala Thr
    130                 135                 140

Leu Leu Ile His Glu Gly Val Lys Ala Glu Glu Ile Phe Glu Lys Thr
145                 150                 155                 160

Gly Gln Val Pro Asp Pro Thr Ser Thr Asp Asn Pro Glu Phe Gln Ile
                165                 170                 175

Val Leu Ser Ile Ile Lys Glu Gly Leu Gln Val Asp Pro Lys Lys Tyr
            180                 185                 190
```

```
His Lys Met Lys Glu Arg Leu Val Gly Val Ser Glu Thr Thr Thr
            195                 200                 205
Gly Val Lys Arg Leu Tyr Gln Met Gln Glu Ser Gly Ala Leu Leu Phe
210                 215                 220
Pro Ala Ile Asn Val Asn Asp Ser Val Thr Lys Ser Lys Phe Asp Asn
225                 230                 235                 240
Leu Tyr Gly Cys Arg His Ser Leu Pro Asp Gly Leu Met Arg Ala Thr
                245                 250                 255
Asp Val Met Ile Ala Gly Lys Val Ala Val Ile Cys Gly Tyr Gly Asp
            260                 265                 270
Val Gly Lys Gly Cys Ala Ala Ala Met Lys Thr Ala Gly Ala Arg Val
            275                 280                 285
Ile Val Thr Glu Ile Asp Pro Ile Cys Ala Leu Gln Ala Met Met Glu
            290                 295                 300
Gly Leu Gln Val Leu Thr Leu Glu Asp Val Val Ser Glu Ala Asp Ile
305                 310                 315                 320
Phe Val Thr Thr Thr Gly Asn Lys Asp Ile Ile Met Val Asp His Met
                325                 330                 335
Arg Lys Met Lys Asn Asn Ala Ile Val Cys Asn Ile Gly His Phe Asp
                340                 345                 350
Asn Glu Ile Asp Met Gln Gly Leu Glu Thr Phe Pro Gly Val Lys Arg
            355                 360                 365
Ile Thr Ile Lys Pro Gln Thr Asp Arg Trp Val Phe Pro Asp Thr Lys
            370                 375                 380
Ser Gly Ile Ile Val Leu Ala Glu Gly Arg Leu Met Asn Leu Gly Cys
385                 390                 395                 400
Ala Thr Gly His Pro Ser Phe Val Met Ser Tyr Pro Phe Thr Asn Gln
                405                 410                 415
Val Ile Ala Gln Leu Glu Leu Trp Asn Glu Lys Ser Ser Gly Lys Tyr
            420                 425                 430
Glu Lys Lys Val Tyr Val Leu Pro Lys His Leu Asp Glu Lys Val Ala
            435                 440                 445
Ala Leu His Leu Gly Lys Leu Gly Ala Lys Leu Thr Lys Leu Thr Lys
450                 455                 460
Asp Ile
465

<210> SEQ ID NO 12
<211> LENGTH: 1752
<212> TYPE: DNA
<213> ORGANISM: Brassica alboglabra
<220> FEATURE:
<223> OTHER INFORMATION: Brassica alboglabra homolog (nucleotide
      sequence)

<400> SEQUENCE: 12
acggggacac acttctctct acccctctct ctgccccaat cttagatccg aaaaaatggc      60
gttgatcgtt gagaagacgt cgagtggccg tgagtacaag gtcaaggaca tgtctcaggc     120
cgacttcggt cgtctcgagc tcgagctcgc cgaagttgag atgccaggac tcatggcttg     180
ccgtaccgag ttcggcccag ctcagccctt caaaggcgct agaatcaccg gatctctcca     240
catgacgatc cagaccgccg tcctcatcga aaccctaacc gccctcggcg cggaagtcag     300
atggtgctcc tgcaacatct tctcaaccca agaccacgcc gccgccgcaa tcgcccgtga     360
ctccgccgcc gttttcgcct ggaaaggtga gacgcttcag gagtactggt ggtgcacgga     420
```

```
gcgtgctctc gactggggcc caggtggtgg tccagatctg atcgtcgatg acggtggcga    480
cgccacgctt ttgatccacg agggagtgaa ggccgaggag atctttgaga agacgggtca    540
ggttcctgat cccacttcca ctgacaaccc tgagttccag atcgtgcttt cgatcatcaa    600
ggaaggtctc caggttgatc ctaagaagta ccacaagatg aaggagagac tcgtcggtgt    660
ctctgaggag accaccaccg gtgtcaagag gctttaccag atgcaggaaa gtggagccct    720
tttgttccca gccattaacg tcaacgactc cgtcaccaag agcaagttcg acaacttgta    780
cggttgccgt cactctctac ctgatggtct catgagggcc actgatgtca tgatcgccgg    840
aaaggttgcg gttatctgtg ttatggtga tgtcggtaag ggttgtgccg ctgccatgaa    900
aaccgctggt gctagagtca ttgtgaccga gatcgacccc atctgtgccc acaagctat    960
gatggaaggg cttcaagttc tgacccttga ggatgtcgtc tctgaagctg acatctttgt   1020
caccaccacc ggtaacaaag acatcatcat ggttgaccac atgaggaaga tgaagaacaa   1080
cgctatcgtc tgcaacattg gtcactttga caacgagatt gacatgcaag acttgagac   1140
cttccctgga gtgaagcgta tcaccatcaa gccccgacc gacaggtggg tgttcccaga   1200
caccaagtcc ggaatcattg ttttggccga gggtcgtctc atgaacttgg gttgtgccac   1260
tggtcaccca agtttcgtga tgtcttaccc tttcaccaac caggtgattg cccagcttga   1320
gctttggaac gagaagtcga gcggtaagta cgagaagaag gtgtacgttc tacccaagca   1380
tttggatgag aaggttgcgg cacttcactt gggcaagctt ggagctaagc tcactaagct   1440
gacaaaggac atctgactag tcagcattcc cattgaagga ccatacaagc tgctcacta   1500
caggtactga gagaagaatg gagagagcgg tttatttcta gtttggtctt ctgatgaagt   1560
tgaccgaata tccttctgaa taaggattct tgtctttga ttgttgtgct tgttcttctt   1620
ttttctgaat ttatcttgaa acttaaatta gcctttggtt atttgatttt tgtgttgtgtt   1680
cattgttcta ctctttaaaa aatagaaaca aaaaagttgg ataaaaaaa aaaaaaaaaa   1740
aaaaaaaaaa aa                                                        1752

<210> SEQ ID NO 13
<211> LENGTH: 485
<212> TYPE: PRT
<213> ORGANISM: Petunia hybrida
<220> FEATURE:
<223> OTHER INFORMATION: Petunia hybrida homolog (amino acid sequence),
      PETCBP

<400> SEQUENCE: 13

Met Ala Leu Leu Val Glu Lys Thr Thr Ser Gly Arg Glu Tyr Lys Val
1               5                   10                  15

Lys Asp Met Ser Gln Ala Asp Phe Gly Arg Leu Glu Ile Glu Leu Ala
            20                  25                  30

Glu Val Glu Met Pro Gly Leu Met Ala Cys Arg Thr Glu Phe Gly Pro
        35                  40                  45

Ser Gln Pro Phe Lys Gly Ala Lys Ile Thr Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Gln Glu Tyr Trp Trp Cys Thr Glu Arg Ala Leu Asp Trp Gly
```

```
            115                 120                 125
Pro Gly Gly Pro Asp Leu Ile Val Asp Gly Gly Asp Ala Thr
    130                 135                 140
Leu Leu Ile His Glu Gly Val Lys Ala Glu Glu Tyr Ala Lys Asp
145                 150                 155                 160
Gly Thr Val Pro Asp Pro Thr Ser Thr Asp Asn Val Glu Phe Gln Leu
                165                 170                 175
Val Leu Gly Ile Ile Lys Glu Ser Leu Lys Thr Asp Pro Thr Lys His
            180                 185                 190
Thr Lys Met Lys Glu Arg Leu Val Gly Val Ser Glu Glu Thr Thr Thr
        195                 200                 205
Gly Val Lys Arg Leu Thr Arg Cys Lys Leu Met Glu Leu Cys Phe Ser
    210                 215                 220
Gln Leu Pro Asn Val Asn Asp Ser Val Thr Lys Ser Lys Phe Asp Asn
225                 230                 235                 240
Leu Tyr Gly Cys Arg His Ser Leu Pro Asp Gly Leu Met Arg Ala Thr
                245                 250                 255
Asp Val Met Ile Ala Gly Lys Val Ala Val Ala Gly Tyr Gly Asp
            260                 265                 270
Val Gly Lys Gly Cys Ala Met Ser Leu Lys Gln Ala Gly Ala Arg Val
        275                 280                 285
Ile Val Thr Glu Ile Asp Pro Ile Cys Ala Leu Gln Ala Leu Met Glu
    290                 295                 300
Gly Leu Gln Val Leu Thr Leu Glu Asp Val Val Ala Asp Ala Asp Ile
305                 310                 315                 320
Phe Val Thr Thr Thr Gly Asn Lys Asp Ile Ile Met Val Asp His Met
                325                 330                 335
Arg Lys Met Lys Asn Asn Ala Ile Val Cys Asn Ile Gly His Phe Asp
            340                 345                 350
Asn Glu Ile Asp Met Leu Gly Leu Glu Thr Phe Pro Gly Val Lys Arg
        355                 360                 365
Ile Thr Ile Lys Pro Gln Thr Asp Arg Trp Val Phe Pro Asp Thr Asn
    370                 375                 380
Ser Gly Ile Ile Val Leu Ala Glu Gly Arg Leu Met Asn Leu Gly Cys
385                 390                 395                 400
Ala Thr Gly His Pro Ser Val Val Met Ser Cys Ser Phe Thr Asn Gln
                405                 410                 415
Val Ile Ala Gln Leu Glu Leu Trp Asn Glu Lys Ser Ser Gly Lys Tyr
            420                 425                 430
Glu Lys Lys Val Tyr Val Leu Pro Lys His Leu Asp Glu Lys Val Ala
        435                 440                 445
Ala Leu His Leu Gly Lys Leu Gly Ala Lys Leu Thr Lys Leu Ser Lys
    450                 455                 460
Asp Gln Ala Asp Tyr Ile Asn Val Pro Val Glu Gly Pro Tyr Lys Pro
465                 470                 475                 480
Val His Tyr Arg Tyr
                485

<210> SEQ ID NO 14
<211> LENGTH: 1855
<212> TYPE: DNA
<213> ORGANISM: Petunia hybrida
<220> FEATURE:
<223> OTHER INFORMATION: Petunia hybrida homolog (nucleotide sequence),
      PETCBP
```

<400> SEQUENCE: 14

```
gcggggtct cactttcttc ttctctacaa aaccccatc aagaagtaga gctaaaaaac     60
tccatttcaa taatggcttt acttgttgaa aaacaacat caggccgtga gtacaaggtt    120
aaagacatgt ctcaggcaga cttcggccgg ctcgaaatcg agttggccga agttgaaatg   180
cctggactca tggcttgtcg tactgaattt ggaccttcac aaccttttaa aggtgccaag   240
attactggat ctttacatat gactattcaa actgctgtct tgattgagac tttgacagca   300
ttaggtgctg aagttagatg tgttcttgt aatatctttt ctactcaaga tcatgctgct    360
gctgctatcg ctcgtgatag cgctgctgtc ttcgcctgga aggcgagac cttgcaggag    420
tactggtggt gtaccgagag ggcactagat tggggtccag gtggaggacc tgatttgatt   480
gttgatgatg gaggtgacgc tacactcttg attcatgaag gagttaaagc tgaagaagag   540
tatgctaagg atgggacagt cccagatcct acctctaccg ataacgttga gtttcagctt   600
gtgctaggta ttattaagga aagtttaaag actgatccta caaagcatac taagatgaag   660
gaaaggcttg ttggtgtttc tgaggaaact accactggtg ttaagagact taccagatgc   720
aagctaatgg aactttgctt ttcccagcta cccaatgtta acgactctgt taccaagagc   780
aagtttgaca acttgtacgg atgccgccac tcactgcccg atggtctcat gagggctact   840
gatgttatga ttgccggaaa ggttgccgtt gttgccggtt acggagatgt tggcaaaggg   900
tgtgctatgt ccttgaagca agctggtgcc cgtgtgatcg tgactgagat tgacccaatc   960
tgtgctctcc aggctctcat ggaaggccta caagttctca ctcttgagga tgttgttgct  1020
gatgctgata tctttgtcac cacaaccggt aacaaggaca tcatcatggt tgaccacatg  1080
aggaagatga agaacaatgc cattgtctgc aacattggcc actttgacaa tgaaatcgac  1140
atgcttggtc ttgagacatt cccaggtgtg aagaggatca caatcaagcc tcaaactgac  1200
aggtgggtct tcccagacac caacagtggc atcattgtct tggccgaggg tcgtctcatg  1260
aacttgggat gtgccactgg acaccccagt gtcgtgatgt cctgttcttt cactaaccaa  1320
gtcattgccc aactcgagtt gtggaatgag aagagctctg gcaagtatga agaagaaggtg  1380
tacgtcttgc caaagcacct cgacgagaag gtcgctgccc ttcaccttgg aaagctcgga  1440
gccaagctta ccaagctctc caaggatcaa gctgactaca ttaacgtacc agttgagggt  1500
ccttacaagc cagttcacta caggtactaa gggaagacaa attgacagtg agatacatt  1560
ctcgcggcat gattgttttg cttttaatac tttgattttg tttaggatac tagtgttttt  1620
attattgttg gggatatatt gagggaagt tgggcatgtt ttgctggaaa gaaatggtct   1680
catttgaaag aaagacctaa atgtgttgaa taagatttga gttatggttg ggtggtgtgg  1740
tatgatattg tagtaagtta gatccttttg cgttttggtc tatgattttt gtttcaagaa  1800
atcagagcta catttctct ttccaaaaaa aaaaaaaaa aaaaaaaaa aaaaa          1855
```

<210> SEQ ID NO 15
<211> LENGTH: 850
<212> TYPE: DNA
<213> ORGANISM: Artificial sequence
<220> FEATURE:
<223> OTHER INFORMATION: 850 bp Anti-sense Construct of HOG1

<400> SEQUENCE: 15

```
gcgctagaat caccggatct ctccacatga cgatccagac cgccgtcctc atcgaaaccc     60
taaccgccct cggcgcggaa gtcagatggt gctcctgcaa catcttctca acccaagacc    120
```

```
acgccgccgc cgcaatcgcc cgtgactccg ccgccgtttt cgcctggaaa ggtgagacgc    180
ttcaggagta ctggtggtgc acggagcgtg ctctcgactg gggcccaggt ggtggtccag    240
atctgatcgt cgatgacggt ggcgacgcca cgcttttgat ccacgaggga gtgaaggccg    300
aggagatctt tgagaagacg ggtcaggttc ctgatcccac ttccactgac aaccctgagt    360
tccagatcgt gctttcgatc atcaaggaag gtctccaggt tgatcctaag aagtaccaca    420
agatgaaggg gagactcgtc ggtgtctctg aggagaccac caccggtgtc aagaggcttt    480
accagatgca ggaaagtgga gccctttgt tcccagccat taacgtcaac gactccgtca     540
ccaagagcaa gttcgacaac ttgtacggtt gccgtcactc tctacctgat ggtctcatga    600
gggccactga tgtcatgatc gccggaaagg ttgcggttat ctgtggttat ggtgatgtcg    660
gtaagggttg tgccgctgcc atgaaaaccg ctggtgctag agtcattgtg accgagatcg    720
accccatctg tgccctacaa gctatgatgg aagggcttca agttctgacc cttgaggatg    780
tcgtctctga agctgacatc tttgtcacca ccaccggtaa caaagacatc atcatggttg    840
accacatgag                                                          850
```

```
<210> SEQ ID NO 16
<211> LENGTH: 15
<212> TYPE: DNA
<213> ORGANISM: Artificial sequence
<220> FEATURE:
<223> OTHER INFORMATION: Anti-sense Fragment 1

<400> SEQUENCE: 16
ctcggcgcgg aagtc                                                     15

<210> SEQ ID NO 17
<211> LENGTH: 15
<212> TYPE: DNA
<213> ORGANISM: Artificial sequence
<220> FEATURE:
<223> OTHER INFORMATION: Anti-sense Fragment 2

<400> SEQUENCE: 17
tcggcgcgga agtca                                                     15

<210> SEQ ID NO 18
<211> LENGTH: 15
<212> TYPE: DNA
<213> ORGANISM: Artificial sequence
<220> FEATURE:
<223> OTHER INFORMATION: Anti-sense Fragment 3

<400> SEQUENCE: 18
cggcgcggaa gtcag                                                     15

<210> SEQ ID NO 19
<211> LENGTH: 15
<212> TYPE: DNA
<213> ORGANISM: Artificial sequence
<220> FEATURE:
<223> OTHER INFORMATION: Anti-sense Fragment 4

<400> SEQUENCE: 19
ggcgcggaag tcaga                                                     15

<210> SEQ ID NO 20
<211> LENGTH: 9
<212> TYPE: DNA
<213> ORGANISM: Artificial sequence
```

```
<220> FEATURE:
<223> OTHER INFORMATION: siRNA Fragment 1

<400> SEQUENCE: 20 agatccgaa                                                              9

<210> SEQ ID NO 21
<211> LENGTH: 9
<212> TYPE: DNA
<213> ORGANISM: Artificial sequence
<220> FEATURE:
<223> OTHER INFORMATION: siRNA Fragment 2

<400> SEQUENCE: 21 gatccgaaa                                                              9

<210> SEQ ID NO 22
<211> LENGTH: 9
<212> TYPE: DNA
<213> ORGANISM: Artificial sequence
<220> FEATURE:
<223> OTHER INFORMATION: siRNA Fragment 3

<400> SEQUENCE: 22 atccgaaaa                                                              9

<210> SEQ ID NO 23
<211> LENGTH: 9
<212> TYPE: DNA
<213> ORGANISM: Artificial sequence
<220> FEATURE:
<223> OTHER INFORMATION: siRNA Fragment 4

<400> SEQUENCE: 23 tccgaaaaa                                                              9

<210> SEQ ID NO 24
<211> LENGTH: 30
<212> TYPE: DNA
<213> ORGANISM: Artificial sequence
<220> FEATURE:
<223> OTHER INFORMATION: Primer PET1

<400> SEQUENCE: 24
aagatgccct ggactctact atggtcactt                                      30

<210> SEQ ID NO 25
<211> LENGTH: 24
<212> TYPE: DNA
<213> ORGANISM: Artificial sequence
<220> FEATURE:
<223> OTHER INFORMATION: Primer PET2

<400> SEQUENCE: 25
tcagaacttg ctcttggtag acag                                            24

<210> SEQ ID NO 26
<211> LENGTH: 432
<212> TYPE: PRT
<213> ORGANISM: Homo sapiens
<220> FEATURE:
<223> OTHER INFORMATION: Homo sapiens (amino acid sequence), SAHH

<400> SEQUENCE: 26

Met Ser Asp Lys Leu Pro Tyr Lys Val Ala Asp Ile Gly Leu Ala Ala
1               5                   10                  15
```

Trp Gly Arg Lys Ala Leu Asp Ile Ala Glu Asn Glu Met Pro Gly Leu
            20                  25                  30

Met Arg Met Arg Glu Arg Tyr Ser Ala Ser Lys Pro Leu Lys Gly Ala
        35                  40                  45

Arg Ile Ala Gly Cys Leu His Met Thr Val Glu Thr Ala Val Leu Ile
    50                  55                  60

Glu Thr Leu Val Thr Leu Gly Ala Glu Val Gln Trp Ser Ser Cys Asn
65                  70                  75                  80

Ile Phe Ser Thr Gln Asp His Ala Ala Ala Ile Ala Lys Ala Gly
                85                  90                  95

Ile Pro Val Tyr Ala Trp Lys Gly Glu Thr Asp Glu Glu Tyr Leu Trp
                100                 105                 110

Cys Ile Glu Gln Thr Leu Tyr Phe Lys Asp Gly Pro Leu Asn Met Ile
            115                 120                 125

Leu Asp Asp Gly Gly Asp Leu Thr Asn Leu Ile His Thr Lys Tyr Pro
130                 135                 140

Gln Leu Leu Pro Gly Ile Arg Gly Ile Ser Glu Glu Thr Thr Thr Gly
145                 150                 155                 160

Val His Asn Leu Tyr Lys Met Met Ala Asn Gly Ile Leu Lys Val Pro
                165                 170                 175

Ala Ile Asn Val Asn Asp Ser Val Thr Lys Ser Lys Phe Asp Asn Leu
                180                 185                 190

Tyr Gly Cys Arg Glu Ser Leu Ile Asp Gly Ile Lys Arg Ala Thr Asp
            195                 200                 205

Val Met Ile Ala Gly Lys Val Ala Val Ala Gly Tyr Gly Asp Val
            210                 215                 220

Gly Lys Gly Cys Ala Gln Ala Leu Arg Gly Phe Gly Ala Arg Val Ile
225                 230                 235                 240

Ile Thr Glu Ile Asp Pro Ile Asn Ala Leu Gln Ala Ala Met Glu Gly
                245                 250                 255

Tyr Glu Val Thr Thr Met Asp Glu Ala Cys Gln Glu Gly Asn Ile Phe
            260                 265                 270

Val Thr Thr Thr Gly Cys Ile Asp Ile Ile Leu Gly Arg His Phe Glu
        275                 280                 285

Gln Met Lys Asp Asp Ala Ile Val Cys Asn Ile Gly His Phe Asp Val
    290                 295                 300

Glu Ile Asp Val Lys Trp Leu Asn Glu Asn Ala Val Glu Lys Val Asn
305                 310                 315                 320

Ile Lys Pro Gln Val Asp Arg Tyr Arg Leu Lys Asn Gly Arg Arg Ile
                325                 330                 335

Ile Leu Leu Ala Glu Gly Arg Leu Val Asn Leu Gly Cys Ala Met Gly
            340                 345                 350

His Pro Ser Phe Val Met Ser Asn Ser Phe Thr Asn Gln Val Met Ala
        355                 360                 365

Gln Ile Glu Leu Trp Thr His Pro Asp Lys Tyr Pro Val Gly Val His
    370                 375                 380

Phe Leu Pro Lys Lys Leu Asp Glu Ala Val Ala Glu Ala His Leu Gly
385                 390                 395                 400

Lys Leu Asn Val Lys Leu Thr Lys Leu Thr Glu Lys Gln Ala Gln Tyr
                405                 410                 415

Leu Gly Met Ser Cys Asp Gly Pro Phe Lys Pro Asp His Tyr Arg Tyr
            420                 425                 430

```
<210> SEQ ID NO 27
<211> LENGTH: 485
<212> TYPE: PRT
<213> ORGANISM: Lycopersicon esculentum
<220> FEATURE:
<223> OTHER INFORMATION: Lycopersicon esculentum homolog (amino acid
      sequence)

<400> SEQUENCE: 27

Met Ala Leu Leu Val Glu Lys Thr Thr Ser Gly Arg Glu Tyr Lys Val
1               5                   10                  15

Lys Asp Met Ser Gln Ala Asp Phe Gly Arg Leu Glu Ile Glu Leu Ala
            20                  25                  30

Glu Val Glu Met Pro Gly Leu Met Ala Ser Arg Ala Glu Phe Gly Pro
        35                  40                  45

Ser Gln Pro Val Lys Gly Ala Lys Ile Thr Cys Ser Leu His Met Thr
    50                  55                  60

Ile Gln Thr Ala Phe Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Gln Glu Tyr Trp Trp Cys Thr Glu Arg Ala Leu Asp Trp Gly
        115                 120                 125

Pro Gly Gly Gly Pro Asp Leu Ile Val Asp Asp Gly Gly Asp Ala Thr
    130                 135                 140

Leu Leu Ile His Glu Gly Val Lys Ala Glu Glu Phe Ala Lys Asn
145                 150                 155                 160

Gly Thr Val Pro Asp Pro Thr Ser Thr Asp Asn Val Glu Phe Gln Leu
                165                 170                 175

Val Leu Thr Ile Ile Lys Glu Ser Leu Lys Thr Asp Pro Leu Arg Tyr
            180                 185                 190

Thr Lys Met Lys Glu Arg Leu Val Gly Val Ser Glu Glu Thr Thr Thr
        195                 200                 205

Gly Val Lys Lys Leu Tyr Gln Met Pro Ala Asn Gly Ser Leu Leu Phe
    210                 215                 220

Leu Pro Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Leu Val Ala Gly Tyr Gly Asp
            260                 265                 270

Val Gly Lys Gly Cys Ala Ala Met Lys Gln Ala Gly Ala Arg Val
        275                 280                 285

Ile Val Thr Glu Ile Asp Pro Ile Cys Ala Leu Gln Ala Thr Met Glu
    290                 295                 300

Gly Leu Gln Val Leu Phe Leu Glu Asp Val Val Ser Glu Val Asp Ile
305                 310                 315                 320

Phe Val Thr Thr Thr Gly Asn Lys Asp Ile Ile Met Val Asp His Met
                325                 330                 335

Arg Lys Met Lys Asn Asn Ala Ile Val Cys Asn Ile Gly His Phe Asp
            340                 345                 350

Asn Glu Ile Asp Met His Gly Leu Glu Thr Phe Pro Gly Val Lys Arg
        355                 360                 365
```

```
Ile Thr Ile Lys Pro Gln Thr Asp Arg Trp Val Phe Pro Asp Thr Asn
        370                 375                 380
Ser Gly Ile Ile Val Leu Ala Glu Gly Arg Leu Met Asn Leu Gly Cys
385                 390                 395                 400
Ala Thr Gly His Pro Ser Phe Val Met Ser Cys Ser Phe Thr Asn Gln
                405                 410                 415
Val Ile Ala Gln Leu Glu Leu Trp Asn Glu Arg Ser Ser Gly Lys Tyr
                420                 425                 430
Glu Lys Lys Val Tyr Val Leu Pro Lys His Leu Asp Glu Lys Val Ala
        435                 440                 445
Ala Leu His Leu Gly Lys Phe Gly Ala Lys Leu Thr Lys Leu Thr Lys
        450                 455                 460
Asp Gln Ala Asp Tyr Ile Tyr Val Pro Val Glu Gly Pro Tyr Lys Pro
465                 470                 475                 480
Ala His Tyr Arg Tyr
                485

<210> SEQ ID NO 28
<211> LENGTH: 1754
<212> TYPE: DNA
<213> ORGANISM: Lycopersicon esculentum
<220> FEATURE:
<223> OTHER INFORMATION: Lycopersicon esculentum homolog (nucleotide
      sequence)

<400> SEQUENCE: 28
tctcagatct catcttaaac cctttttttt ctcttatact cgccttaccc atggctctac      60
tcgttgagaa gaccacctct ggccgcgagt acaaggtgaa ggacatgtct caggctgact     120
tcggcaggct cgaaatcgag cttgctgaag ttgaaatgcc tggtctcatg gcttcacggg     180
ctgaatttgg gccttcacag cccgttaaag gtgcaaagat cacttgttct tgcatatga     240 ctatccaaac tgctttcctg attgaaaccc taactgcttt gggtgctgaa gttagatggt     300
gttcttgcaa catcttctca actcaggacc atgctgcagc agccattgca cgtgacagtg     360
ctgctgtctt tgcctggaaa ggtgagactt gcaggagta ctggtggtgt actgagaggg      420
cacttgactg gggtccaggt ggtggtcctg atctgattgt tgatgatgga ggtgatgcta     480
ctctgttgat tcatgaggga gttaaggctg aagaggagtt tgctaagaat ggaacagtcc     540
cagatcccac ttctactgac aatgttgagt ttcaacttgt gcttactatt attaaggaga     600
gcttaaagac tgatccatta aggtacacta agatgaagga gagacttgtt ggtgtttctg     660
aggaaactac cactggtgtt aagaagcttt accaaatgcc agctaatgga tcttttgcttt    720 tcctgcctat caatgttaat gactctgtta ccaagagcaa gtttgacaac ttgtatggat     780
gccgccactc acttcccgat ggtctcatga gggctactga tgttatgatt gctggaaagg     840
ttgctcttgt tgctggttat ggagatgtcg gcaaggatg tgctgctgcc atgaaacaag      900
ctggtgcccg tgtgattgtg actgagattg acccaatctg tgctctccag gctaccatgg     960
aaggccttca ggttttgttc ttggaggatg ttgtttctga ggttgatatc tttgtgacca    1020
ccaccggtaa caaggacatc atcatggttg accacatgag gaagatgaag acaatgccaa    1080
ttgtctgcaa cattggtcac tttgacaacg aaatcgacat gcatggtctt gaaaccttcc    1140
ctggtgtgaa gaggatcaca atcaagccac aaaccgacag atgggtcttt cccgacacca    1200
acagtggcat cattgtgttg gccgagggtc gtctcatgaa cttgggatgt gccactggac    1260
accccagttt tgtgatgtct tgctctttca ctaaccaagt cattgcccaa ctcgagttgt    1320
```

-continued

```
ggaatgagag gagcagtggc aaatacgaga agaaggtgta cgtcttgcca aagcaccttg    1380
acgagaaggt tgctgcccTT catcttggaa agttcggagc caagcttacc aaactcacca    1440
aggatcaagc tgactacatt tacgtacctg ttgagggtcc ttacaagcct gctcactaca    1500
ggtactgagg aagagacgct cacagtggaa caacgatacg gcggcatgat tgttttgttt    1560
taaacttttA ttttgtttag gtagtgtgtt tttattttgt tgggggatat tttgctggaa    1620
agttgaccta aatgtgtttg aataatattt gaattatggt tggggtggtg tcatatgata    1680
ttgtaccaag ttagattcat ttgctttctt gtttctataa aatttgcttc aaggaaacaa    1740
agcatcatgt tttt                                                      1754
```

<210> SEQ ID NO 29
<211> LENGTH: 484
<212> TYPE: PRT
<213> ORGANISM: Solanum tuberosum
<220> FEATURE:
<223> OTHER INFORMATION: Solanum tuberosum homolog (amino acid sequence)

<400> SEQUENCE: 29

```
Met Ala Leu Leu Val Glu Lys Thr Thr Ser Gly Arg Glu Tyr Lys Val
1               5                   10                  15

Lys Asp Met Ser Gln Ala Asp Phe Gly Arg Leu Glu Ile Glu Leu Ala
            20                  25                  30

Glu Val Glu Met Pro Gly Leu Met Ala Ser Arg Thr Glu Phe Gly Pro
        35                  40                  45

Ser Gln Pro Phe Lys Gly Ala Lys Ile Thr Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Gln Glu Tyr Trp Trp Cys Thr Glu Arg Ala Leu Asp Trp Gly
        115                 120                 125

Pro Gly Gly Gly Pro Asp Leu Ile Val Asp Asp Gly Gly Asp Ala Thr
    130                 135                 140

Leu Leu Ile His Glu Gly Val Lys Ala Glu Glu Phe Ala Lys Asn
145                 150                 155                 160

Gly Thr Ile Pro Asp Pro Thr Ser Thr Asp Asn Val Glu Phe Gln Leu
                165                 170                 175

Val Leu Thr Ile Ile Lys Glu Ser Leu Lys Thr Asp Pro Leu Arg Tyr
            180                 185                 190

Thr Lys Met Lys Glu Arg Leu Val Gly Val Ser Glu Glu Thr Thr Thr
        195                 200                 205

Gly Val Lys Arg Leu Tyr Gln Met Gln Ala Asn Gly Thr Leu Leu Phe
    210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Leu Val Ala Gly Tyr Gly Asp
            260                 265                 270

Val Gly Lys Gly Cys Ala Ala Ala Met Lys Gln Ala Gly Ala Arg Val
```

```
                275                 280                 285
Ile Val Thr Glu Ile Asp Pro Ile Cys Ala Leu Gln Ala Thr Met Glu
            290                 295                 300
Gly Leu Gln Val Leu Pro Leu Glu Asp Val Val Ser Glu Val Asp Ile
305                 310                 315                 320
Phe Val Thr Thr Thr Gly Asn Lys Asp Ile Ile Met Val Asp His Met
                325                 330                 335
Arg Lys Met Lys Asn Asn Ala Ile Val Cys Asn Ile Gly His Phe Asp
            340                 345                 350
Asn Glu Ile Asp Met His Gly Leu Glu Thr Phe Pro Gly Val Lys Arg
                355                 360                 365
Ile Thr Ile Ser Ser Asn Asp Arg Trp Val Phe Pro Asp Thr Asn Ser
370                 375                 380
Gly Ile Ile Val Leu Ala Glu Gly Arg Leu Met Asn Leu Gly Cys Ala
385                 390                 395                 400
Thr Gly His Pro Ser Phe Val Met Ser Cys Ser Phe Thr Asn Gln Val
                405                 410                 415
Ile Ala Gln Leu Glu Leu Trp Asn Glu Arg Ser Ser Gly Lys Tyr Glu
            420                 425                 430
Lys Lys Val Tyr Val Leu Pro Lys His Leu Asp Glu Lys Val Ala Ala
            435                 440                 445
Leu His Leu Gly Lys Leu Gly Ala Lys Leu Thr Lys Leu Thr Lys Asp
            450                 455                 460
Gln Ala Asp Tyr Ile Ser Val Pro Val Glu Gly Pro Tyr Lys Pro Ala
465                 470                 475                 480
His Tyr Arg Tyr

<210> SEQ ID NO 30
<211> LENGTH: 1738
<212> TYPE: DNA
<213> ORGANISM: Solanum tuberosum
<220> FEATURE:
<223> OTHER INFORMATION: Solanum tuberosum homolog (nucleotide sequence)

<400> SEQUENCE: 30
aaggaagaag agaaaagctc tcagatctca tctcaaaccc tttcatttct cttatactcg      60
ccttacccat ggctctactc gttgagaaga ccacctctgg ccgcgagtac aaggtgaagg     120
acatgtccca ggcagacttc ggcaggctcg aaatcgagct tgccgaggtt gaaatgcctg     180
gtctcatggc ttcccgtact gaattcggcc cttcacagcc cttttaaggt gcaaagatca     240
ctggatctct gcatatgact atccaaactg ctgtccttat tgaaaccctta actgctttgg     300
gtgctgaagt tagatggtgt tcttgcaaca tcttctcaac tcaggaccat gctgcagcag     360
ccattgcacg tgatagtgct gctgtttttg cctggaaagg tgagactttg caggagtact     420
ggtggtgtac tgagagggca cttgattggg gtccaggtgg tggtcctgat ctgattgttg     480
atgatggagg tgatgctact ctcttgattc atgagggagt taaggcagag gaagagttttg     540
ctaagaatgg gacaatccca gatcctactt ctactgacaa tgttgagttt caacttgtgc     600
ttactattat taaggagagc ttaaagactg atccttttaag gtacactaag atgaaggaga     660
gacttgttgg tgtttctgag gaaactacca ctggtgttaa gaggctttac caaatgcagg     720
ctaatggaac tttgctattc cctgctatca atgttaatga ctctgttacc aagagcaagt     780
ttgacaactt gtatggatgc cgccactcac tgcctgatgg tctcatgagg gctactgatg     840
ttatgattgc cgggaaggtt gctcttgttg ctggttatgg agatgtcggc aagggatgtg     900
```

-continued

```
ctgctgccat gaaacaagct ggtgcccgtg tgattgtgac tgagattgat ccaatctgtg    960
ctcttcaggc aaccatggaa ggactccagg ttcttcctct tgaggatgtt gtttctgagg   1020
ttgatatctt tgtgaccacc actggtaaca aggacatcat catggttgac cacatgagga   1080
agatgaagaa caatgccatt gtctgcaaca ttggtcactt tgacaatgaa atcgacatgc   1140
atggtcttga gaccttccct ggtgtgaaga ggatcacaat cagctcaaac gacagatggg   1200
tcttcccaga caccaacagt ggcatcattg tcttggccga gggtcgtctc atgaacttgg   1260
gatgtgccac tggacacccc agttttgtga tgtcttgctc tttcactaac caagtcattg   1320
cgcaactcga gttgtggaat gagaggagca gtggcaaata cgagaagaag gtgtacgtct   1380
tgccaaaaca cctcgatgag aaggttgctg cccttcatct tggaaagctc ggagccaagc   1440
tcaccaaact taccaaggat caagctgact acatcagcgt accagttgag ggtccttaca   1500
agcctgctca ctacaggtac tgagggaaga gacactcatg gtggaacaac gatatcacgg   1560
cacgattgtt ttgttttttaa tactttgatt ttgtttaggt agtgtgtttt tattattgtt   1620
gggggcaagt tggcatgttt tgctggcacg ttgcacctaa atgtgtttgc aatcatcatt   1680
cgaattcatg gtgttggggt tgtgtcatct gcatattgta ctcaagcatt catttgca    1738
```